US012605407B2

(12) United States Patent
Egli et al.

(10) Patent No.: US 12,605,407 B2
(45) Date of Patent: Apr. 21, 2026

(54) METHODS TO INDUCE TERMINAL DIFFERENTIATION IN STEM CELLS BY INTERFERING WITH DNA REPLICATION, METHODS OF INDUCING PANCREATIC DIFFERENTIATION, AND DIFFERENTIATED CELLS OBTAINED THEREOF

(71) Applicant: The Trustees of Columbia University in the City of New York, New York, NY (US)

(72) Inventors: Dietrich Egli, New York, NY (US); Lina Sui, Fort Lee, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1278 days.

(21) Appl. No.: 17/081,027

(22) Filed: Oct. 27, 2020

(65) Prior Publication Data

US 2021/0052665 A1 Feb. 25, 2021

Related U.S. Application Data

(63) Continuation of application No. PCT/US2019/030349, filed on May 2, 2019.

(60) Provisional application No. 62/789,725, filed on Jan. 8, 2019, provisional application No. 62/693,629, filed on Jul. 3, 2018, provisional application No. 62/665,705, filed on May 2, 2018.

(51) Int. Cl.
    *A61K 35/39* (2015.01)
    *C12N 5/071* (2010.01)
(52) U.S. Cl.
    CPC ............ *A61K 35/39* (2013.01); *C12N 5/0678* (2013.01); *C12N 2506/02* (2013.01); *C12N 2506/45* (2013.01)
(58) Field of Classification Search
    CPC .. A61K 35/39; C12N 5/0678; C12N 2506/02; C12N 2506/45; C12N 5/0676
    See application file for complete search history.

(56) References Cited

U.S. PATENT DOCUMENTS

| | | | |
|---|---|---|---|
| 6,703,017 | B1 | 3/2004 | Peck et al. |
| 6,841,538 | B1 * | 1/2005 | Joshi .................. A61K 41/0038 |
| | | | 435/320.1 |
| 2002/0168763 | A1 | 11/2002 | Yan et al. |
| 2004/0121460 | A1 | 6/2004 | Lumelsky et al. |
| 2007/0015279 | A1 | 1/2007 | Tsang et al. |
| 2010/0028307 | A1 * | 2/2010 | O'Neil ................. C12N 5/0676 |
| | | | 435/377 |
| 2010/0222283 | A1 | 9/2010 | Susztak et al. |
| 2010/0278789 | A1 | 11/2010 | Efrat et al. |
| 2016/0272944 | A1 | 9/2016 | Ding et al. |
| 2017/0355963 | A1 | 12/2017 | Rezania et al. |

FOREIGN PATENT DOCUMENTS

| | | |
|---|---|---|
| WO | 2017019702 A1 | 2/2017 |
| WO | WO 2017/044488 | 3/2017 |
| WO | WO-2017044488 A1 * | 3/2017 ........... C12N 5/0081 |

OTHER PUBLICATIONS

Pokrywczynska et al. Differentiation of Stem Cells into Insulin-Producing Cells: Current Status and Challenges (2013), Archivum Immunologiae et Therapiae Experimentalis, 61:149-158 (Year: 2013).*

Ameri et al. (Apr. 4, 2017). Efficient Generation of Glucose-Responsive Beta Cells from Isolated GP2(+) Human Pancreatic Progenitors. Cell Rep 19, 36-49.

Cliby et al. (Jan. 11, 2002). S phase and G2 arrests induced by topoisomerase I poisons are dependent on ATR kinase function. J Biol Chem 277, 1599-1606.

Gardner et al. (Aug. 17, 2017). The High-Affinity Interaction between ORC and DNA that Is Required for Replication Licensing Is Inhibited by 2-Arylquinolin-4-Amines. Cell Chem Biol 24, 981-992 e984.

Georgieva and Egli (Apr. 10, 2017)., Tying Genetic Stability to Cell Identity, Cell Cycle 16(12), 1139-40.

Hardwick and Philpott (Jun. 2014). Nervous decision-making: to divide or differentiate. Trends Genet 30, 254-261.

Huang et al. (Aug. 2, 2012). Prolonged early G(1) arrest by selective CDK4/CDK6 inhibition sensitizes myeloma cells to cytotoxic killing through cell cycle-coupled loss of IRF4. Blood 120, 1095-1106.

Jennings et al. (Sep. 15, 2015). Human pancreas development. Development 142, 3126-3137.

Koundrioukoff et al. (Jan. 3, 2013). Stepwise activation of the ATR signaling pathway upon increasing replication stress impacts fragile site integrity. PLoS Genet 9, e1003643.

Kulkarni et al. (Sep. 2012). Human beta-cell proliferation and intracellular signaling: driving in the dark without a road map. Diabetes 61, 2205-2213.

Ma et al. (Aug. 1, 2008). A small-molecule E2F inhibitor blocks growth in a melanoma culture model. Cancer Res 68, 6292-6299.

Moruno-Manchon et al. (May 18, 2017). The G-quadruplex DNA stabilizing drug pyridostatin promotes DNA damage and downregulates transcription of Brca1 in neurons. Aging (Albany NY) 9, 1957-1970.

Nostro et al. (Apr. 14, 2015). Efficient generation of NKX-1+ pancreatic progenitors from multiple human pluripotent stem cell lines. Stem Cell Reports 4, 591-604.

(Continued)

*Primary Examiner* — Valarie E Bertoglio

(74) *Attorney, Agent, or Firm* — FULLER IP LAW LLC; Scott H. Blackman; Rodney J. Fuller

(57) ABSTRACT

The current invention provides for methods and systems of inducing cell cycle exit and terminal differentiation in stem cells undergoing differentiation into various mature cell types in particular pancreatic endocrine cells. The current invention also provides for methods and systems of inducing differentiation of pancreatic endocrine cells from stem cells. The invention also provides for the cells produced by the methods that are suitable for transplantation or grafting into a subject for the prevention and/or treatment of disease, and useful for basic research and drug testing.

15 Claims, 36 Drawing Sheets

Specification includes a Sequence Listing.

(56) References Cited

OTHER PUBLICATIONS

Pardee et al. (Sep. 2004). Regulation in S phase by E2F. Cell Cycle 3, 1091-1094.

Shih et al. (May 6, 2012) A Notch-dependent molecular circuitry initiates pancreatic endocrine and ductal cell differentiation. Development 139, 2488-99.

Rouaud et al. (May 1, 2018). E2F1 inhibition mediates cell death of metastatic melanoma. Cell Death Dis 9, 527.

Schaffer et al. (2013). Nkx6.1 controls a gene regulatory network required for establishing and maintaining pancreatic Beta cell identity. PLoS Genet 9, e1003274. Received Sep. 21, 2012.

Simon et al. (Jul. 24, 2013). Ciprofloxacin is an inhibitor of the Mcm2-7 replicative helicase. Biosci Rep 33.

Smith et al. (Mar. 23, 1994). Etoposide-induced cell cycle delay and arrest-dependent modulation of DNA topoisomerase II in small-cell lung cancer cells. Br J Cancer 70, 914-921.

Wagner and Karnitz (Jul. 2009). Cisplatin-induced DNA damage activates replication checkpoint signaling components that differentially affect tumor cell survival. Mol Pharmacol 76, 208-214.

Zimmer et al. (Feb. 4, 2016). Targeting BRCA1 and BRCA2 Deficiencies with G-Quadruplex-Interacting Compounds. Mol Cell 61, 449-460.

Bhattacharyya, S., et al. "The voyage of stem cell toward terminal differentiation: a brief overview" Acta Biochimica et Biophysica Sinica, vol. 44 / Issue 6, pp. 463-475 Jun. 2012.

Rezania A, et al., "Reversal of diabetes with insulin-producing cells derived in vitro from human pluripotent stem cells", Nature Biotechnology, vol. 32 / Issue 11, pp. 1121-1133, Nov. 2014.

Pagliuca FW et al., "Generation of functional human pancreatic β cells in vitro", Cell vol. 159 / Issue 2, pp. 428-439, Oct. 2014.

Wingert S., et al., "Terminal differentiation induction as DNA damage response in hematopoietic stem cells by GADD45A", Experimental Hematology, vol. 44/ Issue 7, 99. 561-566, Jul. 2016

Neuss S., et al., "Long-term survival and bipotent terminal differentiation of human mesenchymal stem cells (hMSC) in combination with a commercially available three-dimensional collagen scaffold", Cell Transplant, vol. 17 / Issue 8, pp. 977-986 Aug. 1, 2008.

Pall ML, "DNA replication and the stability of cell differentiation", Differentiation vol. 2 / Issue 6, pp. 363-365, Dec. 1974.

Esteafanía MM, et al., "DNA replication fading as proliferating cells advance in their commitment to terminal differentiation," Scientific Reports, vol. 2, p. 279, Jan. 11, 2012.

D'Amour et al. (Oct. 28, 2005). Efficient differentiation of human embryonic stem cells to definitive endoderm, Nature Biotechnology 23, 1534-41.

D'Amour et al. (Nov. 2006). Production of pancreatic hormone-expressing endocrine cells from human embryonic stem cells. Nature Biotechnology 24, 1392-1401.

Laskoet al. (Oct. 2017). Discovery of a selective catalytic p300/CBP inhibitor that targets lineage-specific tumours. Nature 550, 128-132.

Mfopou and Bouwens (Feb. 2008). Hedge-hog signals in pancreatic differentiation from embryonic stem cells: revisiting the neglected. Differentiation 76, 107-17.

Mfopou et al (June 2010). Noggin. Retinoids, and fibroblast growth factor regulate hepatic or pancreatic fate of human embryonic stem cells. Gastroenterology 138, 2233-45.

Qin and Ng (Jan. 2002). Induction of apoptosis by cisplatin and its effect on cell cycle-related proteins and cell cycle changes in hepatoma cells. Cancer Lett 175, 27-38.

Sclafani and Holzen (Dec. 2007). Cell cycle regulation of DNA replication. Annu Rev Genet 41, 237-280.

Sui et al. (Oct. 2018). Pancreatic Beta Cell Differentiation From Human Pluripotent Stem Cells. Curr Protoc Hum Genet 99, e68.

Extended European Search Report for corresponding European Application No. 19797103.9, dated Jan. 31, 2022. 10 pages.

Soufi Abdenour et al: "Cycling through developmental decisions: how cell cycle dynamics control pluripotency, differentiation and reprogramming", Development, vol. 143, No. 23, Dec. 1, 2016. pp. 4301-4311. 11 pages.

Pauklin Siim et al: "The Cell-Cycle State of Stem Cells Determines Cell Fate Propensity", Cell, Elsevier, Amsterdam NL, vol. 155, No. 1, Sep. 26, 2013 (Sep. 26, 2013), pp. 135-147. 13 pages.

Boward Ben et al: "Concise Review: Control of Cell Fate Through Cell Cycle and Pluripotency Networks", Stem Cells, vol. 34, No. 6, Jun. 1, 2016 (Jun. 1, 2016), pp. 1427-1436. pp. 21.

Sclafani R. A. et al: "Cell Cycle Regulation of DNA Replication", Annual Review of Genetics ., vol. 41, No. 1, Dec. 1, 2007 (Dec. 1, 2007), pp. 237-280. 44 pages.

Sui Lina et al: "Reduced replication forkspeed promotes pancreatic endocrine differentiation and controls graft size". JCI Insight, vol. 6, No. 5, Mar. 8, 2021. 50 Pages.

Sui et al. "B-Cell Replacement in Mice Using Human Type 1 Diabetes Nuclear Transfer Embryonic Stem Cells", Diabetes, vol. 67, Jan. 2018; pp. 26-335; Supplementary Data pp. 1-14; abstract; p. 28, col. 1, second paragraph; Supplementary Data, p. 1, first paragraph-seventh paragraph. http://diabetes.diabetesjournals.org/lookup/suppl/doi:10.2337/db17-0120/-/DC1.

* cited by examiner

Control

APH

C-peptide d27 Control d27 APH

Fig. 4A (cont)

day 60

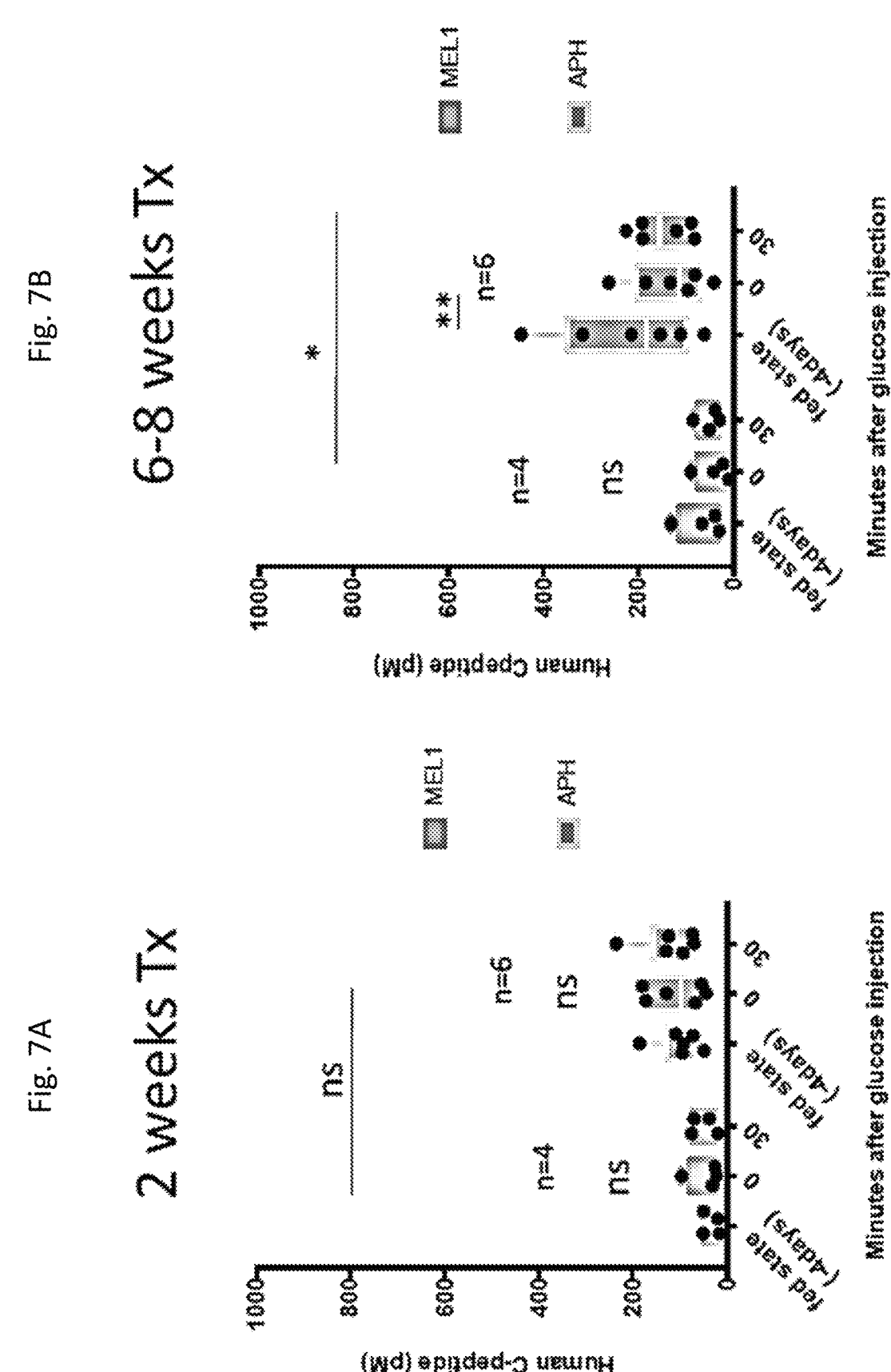

13-15 weeks Tx 9-11 weeks Tx 2 weeks post Tx 13 weeks post Tx

APH

Control

```
                         SEQUENCE LISTING

<160> NUMBER OF SEQ ID NOS: 18

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer

<400> SEQUENCE: 1
tgggctcgag aaggatgtg                                              19

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
gcatagtcgc tgcttgatcg                                             20

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3
ggcgcagcag aatccaga                                               18

<210> SEQ ID NO 4
<211> LENGTH: 18
<212> TYPE: DNA
<213> ORGANISM: Artificial Sequence
<220> FEATURE:
<223> OTHER INFORMATION: Synthetic Primer

<400> SEQUENCE: 4
ccacgacttg cccagcat                                               18

<210> SEQ ID NO 5
<211> LENGTH: 18
<212> TYPE: DNA
<213> ORGANISM: Artificial Sequence
<220> FEATURE:
<223> OTHER INFORMATION: Synthetic Primer

<400> SEQUENCE: 5
gggagcggtg aagatgga                                               18

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer
```

<400> SEQUENCE: 6
tcatgttgct cacggaggag ta                                          22

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
ccctgggtga ccactaaacc                                             20

<210> SEQ ID NO 8
<211> LENGTH: 20
<212> TYPE: DNA
<213> ORGANISM: Artificial Sequence
<220> FEATURE:
<223> OTHER INFORMATION: Synthetic Primer

<400> SEQUENCE: 8
cacagcctct acctcggaac                                             20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
attcgttggg gatgacagag                                             20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
cgagtcctgc ttcttcttgg                                             20

<210> SEQ ID NO 11
<211> LENGTH: 21
<212> TYPE: DNA
<213> ORGANISM: Artificial Sequence
<220> FEATURE:
<223> OTHER INFORMATION: Synthetic Primer

<400> SEQUENCE: 11
tcttttctcc tttggggctg g                                           21

<210> SEQ ID NO 12
<211> LENGTH: 20
<212> TYPE: DNA
<213> ORGANISM: Artificial Sequence
<220> FEATURE:
<223> OTHER INFORMATION: Synthetic Primer

<400> SEQUENCE: 12
tctcacgggt cacttggaca                                             20

<210> SEQ ID NO 13

```
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
gttccagcag aagcttctcg                                                  20

<210> SEQ ID NO 14
<211> LENGTH: 20
<212> TYPE: DNA
<213> ORGANISM: Artificial Sequence
<220> FEATURE:
<223> OTHER INFORMATION: Synthetic Primer

<400> SEQUENCE: 14
gctgaaattc tccccgcctt                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
ttctacacac ccaagacccg                                                  20

<210> SEQ ID NO 16
<211> LENGTH: 17
<212> TYPE: DNA
<213> ORGANISM: Artificial Sequence
<220> FEATURE:
<223> OTHER INFORMATION: Synthetic Primer

<400> SEQUENCE: 16
caatgccacg cttctgc                                                     17

<210> SEQ ID NO 17
<211> LENGTH: 20
<212> TYPE: DNA
<213> ORGANISM: Artificial Sequence
<220> FEATURE:
<223> OTHER INFORMATION: Synthetic Primer

<400> SEQUENCE: 17
aagttcccaa agagggcttg                                                  20

<210> SEQ ID NO 18
<211> LENGTH: 20
<212> TYPE: DNA
<213> ORGANISM: Artificial Sequence
<220> FEATURE:
<223> OTHER INFORMATION: Synthetic Primer

<400> SEQUENCE: 18
agctgccttg taccagcatt                                                  20
```

METHODS TO INDUCE TERMINAL DIFFERENTIATION IN STEM CELLS BY INTERFERING WITH DNA REPLICATION, METHODS OF INDUCING PANCREATIC DIFFERENTIATION, AND DIFFERENTIATED CELLS OBTAINED THEREOF

CROSS REFERENCE TO RELATED APPLICATION

The present application is a continuation of International Patent Application No. PCT/US2019/030349, with an international filing date of May 2, 2019, which claims priority to U.S. patent application serial Nos. 62/665,705 filed May 2, 2018, 62/693,629 filed Jul. 3, 2018, and 62/789,725 filed Jan. 8, 2019, which are all hereby incorporated by reference in its entirety.

STATEMENT OF GOVERNMENTAL INTEREST

This invention was made with government support under DK103585 awarded by National Institutes of Health. The government has certain rights in the invention.

FIELD OF THE INVENTION

The current invention provides for methods and systems of inducing terminal differentiation in stem cells undergoing differentiation into various mature cell types. The invention also provides for the cells produced by the method that are suitable for transplantation or grafting into a subject for the prevention and/or treatment of disease, and useful for basic research and drug testing.

BACKGROUND OF THE INVENTION

Subjects with type 1 diabetes lose most of their beta cell mass and depend on exogenous insulin for control of blood glucose levels. The life-long management of diabetes is imperfect, can result in complications and is a tremendous burden to the affected. Because beta cells are generated very slowly in mature islets, an exogenous source of beta cells could be therapeutically useful, not only for type 1 diabetes, but also for all other forms of diabetes, including type 2 diabetes and monogenetic forms of diabetes. Transplantation of islets from pancreatic organ donors can restore physiological regulation of blood glucose. However, obtaining islets from organ donors is logistically complex, and limited by the number of donors. In general, only a small number of patients with diabetes are treated using this approach.

Human pluripotent stem cells provide a potentially unlimited source of beta cells to replace the missing beta cells and restore glucose homeostasis. In animal models, such proof-of-principle experiments have been successful: human beta cells differentiated from stem cells can protect mice from diabetes upon transplantation. See Sui et al., 2018a. However, there is a need for stable fully functional pancreatic beta cells differentiated from stem cells, as well as other cell types differentiated from stem cells.

A major obstacle in stem cell differentiation of all cell types is the generation of terminally differentiated and fully functional differentiated cells. This is a major obstacle for the generation of cells suitable for basic research, drug testing, and cell replacement suitable for therapeutic use.

Cell cycle plays an active role in developmental decisions. The duplication of the DNA is a fundamental requirement for cell proliferation in both embryonic development and in adult organs. Cell proliferation during development determines the number of cells in the adult organ and is limited by the number of embryonic progenitors in the pancreas. Proliferation of beta cells in the developing human pancreas occurs primarily during embryogenesis, and declines after birth. Indeed proliferation in the adult beta cells is essentially absent (Jennings et al., 2015; Kulkarni et al., 2012). During terminal differentiation, many cell types, including beta cells, neurons and muscle cells undergo cell cycle exit to reach full maturity and adopt full functionality (Ameri et al., 2017; Hardwick and Philpott, 2014; Walsh and Perlman, 1997).

Based upon this knowledge, the inventor published on the concept that cell types use changes in the cell type specific DNA replication program to activate DNA replication checkpoints, and enable cell cycle exit and terminal differentiation (Georgieva and Egli, 2017). Thus, it follows that these changes may be induced to enable terminal differentiation and functional maturation of stem cell derived cells.

The current invention is a novel method for providing mature differentiated cells suitable for transplantation and grafting, wherein the graft function is maintained, as well as cells suitable for basic research and testing.

SUMMARY OF THE INVENTION

The current invention is a method of inducing cell cycle exit and terminal differentiation of cells undergoing differentiation from stem cells comprising contacting or incubating the cells with an agent or agents which interferes with DNA replication.

A further embodiment of the current invention is a method of obtaining a specific differentiated cell or cells from stem cells suitable for administering, grafting or transplanting into a subject, comprising inducing cell cycle exit and terminal differentiation of stem cells undergoing differentiation comprising contacting or incubating the cells with an agent or agents which interferes with DNA replication.

In a further embodiment, the current invention is a method of obtaining a substantially homogenous population of specific differentiated cells from stem cells, comprising inducing cell cycle exit and terminal differentiation of stem cells undergoing differentiation comprising contacting or incubating the cells with an agent or agents which interferes with DNA replication.

In another embodiment, the current invention is a method for inducing differentiation of stem cells into a specific differentiated cell or cells, comprising inducing cell cycle exit and terminal differentiation of stem cells undergoing differentiation comprising contacting or incubating the cells with an agent or agents which interferes with DNA replication.

Further embodiments of the present invention are systems for obtaining a specific differentiated cell or cells from stem cells suitable for administering, grafting or transplanting into a subject, comprising inducing cell cycle exit and terminal differentiation of stem cells undergoing differentiation comprising contacting or incubating the cells with an agent or agents which interferes with DNA replication.

Further embodiments of the present invention are systems for obtaining a substantially homogenous population of specific differentiated cells, comprising inducing cell cycle exit and terminal differentiation of stem cells undergoing differentiation comprising administering an agent which interferes with DNA replication.

Further embodiments of the present invention are systems for inducing differentiation of stem cells into a specific differentiated cell or cells, comprising inducing cell cycle exit and terminal differentiation of stem cells undergoing differentiation comprising administering an agent which interferes with DNA replication.

Stem cells include embryonic stem cells and induced pluripotent stem cells.

In some embodiments, the cells are contacted or incubated with the agents at the stage where the cells have differentiated into progenitor cells. Progenitor cells include but are not limited to endocrine, endothelial, e.g., lung and airway progenitors, satellite cells, intermediate progenitor cells, radial glial cells, bone marrow stromal cells, periosteum cells, and blast cells.

In some embodiments, the cells are contacted or incubated with the agents at about day 15 of the differentiation protocol, for about five days to about one week to about two weeks. In some embodiments, the cells are contacted or incubated with the agents at about day 20 of the differentiation protocol, for about one week to about two weeks. In some embodiments, the cells are contacted or incubated with the agents at early stage of differentiation of progenitor cells to mature differentiated cells which is from about day 15 to about day 20 of the entire differentiation protocol. In some embodiments, the cells are contacted or incubated with the agents at the late stage of differentiation of progenitor cells to mature differentiated cells which is from about day 20 to about day 27 of the entire differentiation protocol. In some embodiment, the cells are contacted or incubated with the agents for the entire duration of differentiation of progenitor cells to mature differentiated cells which is from about day 15 to about day 27 of the entire differentiation protocol. In some embodiments, the cells are contacted or incubated with the agents until about day 60 of the entire differentiation protocol. In some embodiments, the cells are contacted or incubated with the agents until the time of use of the cells, e.g., transplantation or grafting into a subject.

In some embodiments, the contacting or incubating of the cells with the various agents is accomplished by culturing the cells in media comprising the agents.

Agents which can be used in the methods of the invention include but are not limited to the following classes of molecules:

inhibitors of DNA polymerase, such as aphidicolin and gemcitabine;

compounds that stabilize G4 structures and arrest cell cycle, such as pyridostatin and TMPyP4;

inhibitors of the master transcription factors involved in S phase entry, such as E2F inhibitor; DNA helicase inhibitors, such as of WRN including WRN NSC 19630 and WRN NSC 671145, and BLM, including BLM ML216, and DNA2 including DNA2 C5 and DNA2 NSC-105808, and DDX;

topoisomerase inhibitors, such as etoposide, doxorubicin, topotecan and irinotecan;

inhibitors of MCM2-7 replicative helicase, such as ciprofloxacin;

inhibitors of MCM 4/6/7 replicative helicase, such as heliquinomycin;

inhibitors of RecQ helicases, such as RECQL1, RECQL4 and RECQL5;

inhibitors of histone acetylases, such as small molecules A485 and C646 (inhibitor of p300 and Creb-binding protein (CBP)), curcumin, garcinol, and 5-chloro-2-(4-nitrophenyl)-3(2H)-isothiazolone;

inhibitors of replication origin licensing, such as RL5a; and

DNA damaging agents, such as cisplatin or derivatives, chlorambucil, cyclophosphamide, alkylating agents, such as temozolomide (TMZ), 5-fluorouracil, and irradiation.

Specific agents that induce stalling of DNA replication in a site and cell type specific manner also include PNA oligos that stably bind to DNA at specific sites of the genome In some embodiments, the agent is chosen from the group consisting of aphidicolin, cisplatin, ciprofloxacin, pyridostatin, E2Fi, A485, RL5a and etoposide.

In additional embodiments, the invention includes a specific mature differentiated cell or cells obtained by the methods described herein. In some embodiments, the specific mature differentiated cell or cells is chosen from the group consisting of pancreatic endocrine cells, pancreatic cells, endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In some embodiments, these specific mature differentiated cells have markers characteristic of a specific mature differentiated cell. In some embodiments, the cells are positive for cell markers C-peptide and NKX6.1 (mature pancreatic cells). In some embodiments, the cells are positive for cell markers NKX2.1, FOXA2, and SOX2 (mature lung cells). In some embodiments, the cells are positive for cell markers EPCAM and ITGβ4 (mature esophageal cells).

Further embodiment of the current invention is a method of obtaining a pancreatic cell or cells differentiated from stem cells suitable for administering, grafting or transplanting into a subject, comprising the differentiation protocol set forth in Table 1.

An additional embodiment of the current invention is a method of obtaining a substantially homogenous population of pancreatic cells differentiated from stem cells suitable for administering, grafting or transplanting into a subject, comprising the differentiation protocol set forth in Table 1.

Yet an additional embodiment of the current invention is a method of inducing differentiation of stem cells into pancreatic cells suitable for administering, grafting or transplanting into a subject, comprising the differentiation protocol set forth in Table 1.

In additional embodiments, the invention includes a specific mature differentiated cell or cells obtained by the methods described herein. In some embodiments, the specific mature differentiated cell or cells is chosen from the group consisting of pancreatic endocrine cells, pancreatic cells, and endocrine cells. In some embodiments, the cells are positive for cell markers C-peptide and NKX6.1 (mature pancreatic cells).

In certain embodiments, the invention is a composition comprising a specific mature differentiated cell or cells obtained by any of the methods described herein. In some embodiments, the composition is a pharmaceutical composition.

In additional embodiments, the invention includes a population of substantially homogenous specific mature differentiated cells obtained by any of the methods described herein. In some embodiments, the population of cells comprises at least about 90%, 91%, 92%, 93%, 94%, 95%, 96%, 97%, 98%, or 99% specific differentiated cells.

In certain embodiments, the invention is a composition comprising a population of substantially homogenous specific mature differentiated cells obtained by any of the methods described herein. In some embodiments, the composition is a pharmaceutical composition.

A further embodiment of the present invention is a solution comprising a population of substantially homogenous specific mature differentiated cells obtained by any of the methods described herein. These solutions can be injected into a subject. These solutions can be frozen. These solutions can be used for the manufacture of a medicament for a disease that can be treated by the administration of differentiated cells.

This invention also provides methods for producing a solution of substantially homogenous specific mature differentiated cells suitable for injection into a patient comprising the steps of obtaining the cells described herein and placing the cells into solution suitable for injection into a patient. This invention also provides methods of producing a solution of substantially homogenous differentiated cells suitable for freezing comprising the steps of obtaining the cells as described herein and placing into a solution suitable for freezing.

A further embodiment of the present invention is a cell culture comprising substantially homogenous specific differentiated cells.

All of the foregoing embodiments including cells, and solutions, compositions and pharmaceutical compositions comprising the cells can be used to treat and/or prevent disease.

Thus, a further embodiment of the present invention is a method of treating and/or preventing disease in a subject, in need thereof, comprising administering, transplanting or grafting the cells or population of cells obtained by any of the methods and the systems of the invention described herein.

Yet a further embodiment of the present invention is a method of treating and/or preventing disease in a subject, in need thereof, comprising administering a composition or solution comprising the cells or population of cells obtained by any of the methods of the invention described herein. In some embodiments, the composition is a pharmaceutical composition.

In yet additional embodiments, the invention relates to kits for practicing any of the methods of the invention and to obtain the cells and pharmaceutical compositions of the invention. The invention also includes kits comprising the cells and composition of the invention.

As described herein, the methods, systems and kits are suitable for the large-scale, reproducible production of pancreatic endocrine cells and other cells differentiated from iPS cells and work well in control iPS cells as well as in patient-derived iPS cells.

The methods, systems, kits, cells, solutions, compositions and pharmaceutical compositions of the present invention are particularly useful for differentiating pancreatic endocrine cells from stem cells, wherein the differentiated pancreatic endocrine cells are useful for the prevention and treatment of diabetes.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

FIG. 7—Aphdicolin treated cells protected mice from diabetes. FIG. 7A shows a graph of human C-peptide serum concentration in mice at 2 weeks after transplantation with cells treated with APH (APH) and control cells (MEL1) at fed state, fasting and 30 minutes after glucose injection. FIG. 7B shows a graph of human C-peptide serum concentration in mice at 6-8 weeks after transplantation with cells treated with APH (APH) and control cells (MEL1) at fed state, fasting and 30 minutes after glucose injection.

DETAILED DESCRIPTION OF THE INVENTION

Figures 1, 1A:
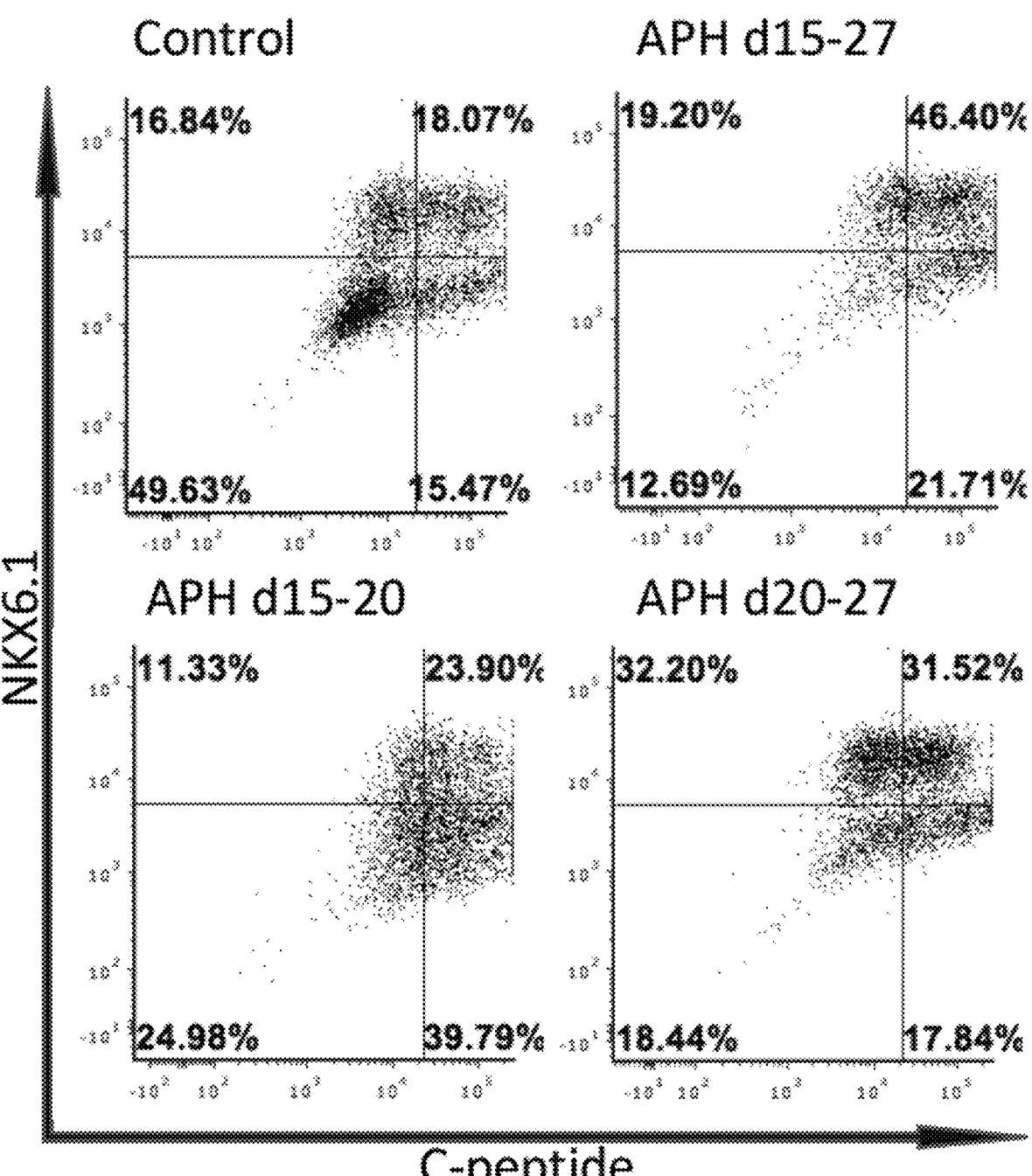
FIG. 1—Inhibition of DNA replication increased beta cell purity.
FIG. 1A are images of flow cytometry analysis of C-peptide positive, and NKX6.1 positive cells derived at the end of differentiation at day 27 where aphidicolin (APH) was added from about days 15-27, from about days 15-20, and from about days 20-27 versus control (no addition of APH).

It is shown herein that genetic instability during DNA replication provides the cellular signals that prevent cell type transitions, and thereby stabilize the differentiated state. Thus, to induce terminal differentiation and obtain stable differentiated cells, interference with DNA replication may be performed at specific sites in the genome, or through unspecific interference with the progression of DNA replication. The current invention utilizes various agents which interfere with DNA replication and induce the terminal differentiation of mature differentiated cells which have improved function and stability.

Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

As used herein, the term "induced pluripotent stem cells" commonly abbreviated as iPS cells or iPSCs, refers to a type of pluripotent stem cell artificially generated from a non-pluripotent cell, typically an adult somatic cell, or terminally differentiated cell, such as fibroblast, a hematopoietic cell, a myocyte, a neuron, an epidermal cell, or the like.

As used herein, the term the terms "differentiation", "cell differentiation" and the like refer to a process by which a less specialized cell (i.e., stem cell) develops or matures or differentiates to possess a more distinct form and/or function into a more specialized cell or differentiated cell, (i.e., pancreatic beta cell).

A cell that results from this process termed herein as a "differentiated cell" and can include pancreatic endocrine cells, pancreatic cells, endocrine cells, as well as neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

As used herein, the expressions "cell," "cell line," and "cell culture" are used interchangeably and all such designations include progeny. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

With respect to cells, the term "isolated" refers to a cell that has been isolated from its natural environment (e.g., from a tissue or subject). The term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as an RNA, has been introduced.

As used herein, the terms "pancreatic endocrine cell", "pancreatic cell" or "endocrine cell" are used interchangeably and denote cells found in the pancreas that secrete hormones. "Pancreatic beta cells" secrete insulin and "pancreatic alpha cells" secrete glucagon.

The term "homogenous" as used herein means of all of the same kind.

The term "substantially" as used herein means almost completely.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject.

The term "in need thereof" would be a subject known or suspected of having or being at risk of developing a disease including but not limited to diabetes including type 1, type 2, and monogenetic.

A subject in need of treatment would be one that has already developed the disease. A subject in need of prevention would be one with risk factors of the disease.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The term "agent" as used herein means a substance that produces or is capable of producing an effect and would include, but is not limited to, chemicals, pharmaceuticals, drugs, biologics, small molecules, antibodies, nucleic acids, peptides, and proteins.

Standard methods in molecular biology are described Sambrook, Fritsch and Maniatis (1982 & 1989 2$^{nd}$ Edition, 2001 3$^{rd}$ Edition, 2012 4$^{th}$ Edition) *Molecular Cloning, A Laboratory Manual*, Cold Spring Harbor Laboratory Press, Cold Spring Harbor, NY; Sambrook and Russell (2001) *Molecular Cloning, 3$^{rd}$ ed.*, Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology*, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Abbreviations d—day

APH—aphidicolin

PDS—pyridostatin

Cis—cisplatin

Eto—etoposide

Cipro—ciprofloxacin

Methods of Obtaining Pancreatic Beta Cells

The current invention is a method interfering with DNA replication to induce cell exit and terminal differentiation and thus obtain differentiated cells which have increased stability and purity, function and homogeneity of the differentiated cells, which in turn increases maturation and functionality, and reduces teratoma formation.

A human pluripotent stem cell is the starting material of the methods of the invention. The human pluripotent stem cell (hPSCs) can be an embryonic stem cells (ESCs) or an induced pluripotent stem cell (iPSCs). As shown herein the method increased the differentiation potential of cells that normally differentiate poorly (see Example 3).

One exemplary method in which the agents which interfere with DNA replication can be used to induce cell exit and terminal differentiation and thus obtain differentiated cells which have increased stability and function is a method for differentiating hPSCs into pancreatic beta cells. This method is exemplified in Example 2 and summarized in Table 1.

TABLE 1

Timeline of a Method for Differentiating Stem Cells to Pancreatic Endocrine Cells using the Methods of the Invention

| STEP | TIMING | GENERAL DESCRIPTION |
|---|---|---|
| 1 | Performed from about day 1 to about day 4 (about 72 hours) | Induce differentiation of hPSCs to definitive endoderm cells |
| 2 | Performed about 74 hours to about 96 hours after the start of step 1, thus starting from about day 4 to about day 5 and performed for about 48 to about 72 hours, ending at about day 6 to day 8 | Induce differentiation of endoderm cells to primitive gut tube cells, using fibroblast growth factor |
| 3 | Performed about 48 hours to about 72 hours after the start of step 2, thus starting from about day 6 to about day 8 and performed for about 2 days to about 4 days ending at about day 6 to about day 12 | Induce differentiation of primitive gut tube cells to posterior foregut cells, using an agent or agents which inhibit sonic hedgehog and BMP4, and activate retinoic acid pathway |
| 4 | Performed for about 2 days to about 4 days after step 3 ending at about day 8 to about day 16 | Induce differentiation of posterior foregut cells to pancreatic progenitor cells, using an agent or agents which activate protein kinase C pathway |
| 5 | Performed for about 6 days to 8 days after step 4 ending at about day 14 to about day 24 | Induce differentiation of pancreatic progenitor cells to endocrine progenitor cells, using an agent or agents which inhibit Notch signaling and TGF-beta signaling, and thyroid hormone |
| 6 | Performed for about a week to 2 weeks after step 5 ending at about day 21 to day 40 and up to day 60 | Induce differentiation of pancreatic progenitor cells to beta cells using an agent or agents which interferes with DNA replication and induces cell exit and terminal differentiation |

In step 2, the cells are contacted or incubated with fibroblast growth factor, in an amount ranging from about 20 ng/ml to about 100 ng/ml, with 50 ng/ml being preferred.

In step 3, the cells are contacted or incubated with an agent or agents which inhibit sonic hedgehog and/or bone morphogenetic protein (BMP4). LDN193189, which inhibits both is exemplified. However, other agents which inhibit either sonic hedgehog or BMP4 or both can be used. These agents include but are not limited to vismodegib, taladegib, jervine, cyclopamine, and sonidegib. In this step, the cells are also contacted or incubated with an agent which activates the retinoic acid pathway. Retinoic acid is exemplified activator of the pathway and can be used in an amount ranging from 1 μM to 3 μM. Other agents which activate the pathway include but are not limited to Isotretinoin, Tazarotene, TTNPB, and AM80.

In step 4, the cells are contacted or incubated with epidermal growth factor (EGF) in an amount ranging from about 20 ng/ml to about 100 ng/ml, with 50 ng/ml being preferred. Other agents which activate the protein kinase C pathway can be used in the method and include but are not limited to Bryostatin 1, 2, 3, FR236924, PEP 005, Phorbol 12,13-dibutyrate, Phorbol 12-myristate 13-acetate, Prostratin, Pseudo RACK1, SC9, and TPPB.

In step 5, the cells are contacted or incubated with thyroid hormone in an amount ranging from about 0.5 μM to about 2 μM, with 1 μM being preferred. The cells are also contacted or incubated with an agent or agents which inhibit Notch signaling. Dibenzazepine (DBZ) is exemplified but other agents can be used in the method including but not limited to Avagacestat, Begacestat, BMS299897, Compound E, Compound W, DAPT, DBZ, Flurizan, JLK6, L-685,458, LY450139, MRK560, and PF 3084014 hydrobromide. The cells are also contacted or incubated with an agent or agents which inhibit TGF-beta signaling. Alk5 is exemplified but other agents can be used including but not limited to A77-01, A 83-01, D 4476, GW 788388, IN 1130, LY 364947, R 268712, Repsox, SB 431542, SB 505124, SB525334, SD 208, and SM 16.

This exemplary protocol of differentiating stem cells to pancreatic endocrine or beta cells includes a step where the cells are contacted or incubated with an agent or agent which interfere with DNA replication to induce cell exit and terminal differentiation (step 6). As discussed below, this step can be used in any differentiation protocol to obtain mature differentiated cells with increased function and stability.

In some embodiments, the contacting or incubating of the cells with the various agents is accomplished by culturing the cells in media comprising the agents. Any media that is used for differentiating and culturing the cells of choice can be used in the methods of the invention.

The present invention also includes systems for practicing the methods of the invention for obtaining stable pancreatic endocrine or beta calls. These systems can include subsystems wherein the subsystems include differentiation medium and agents as outlined above for use at each stage of differentiation.

Methods of Obtaining Mature Differentiated Cells with Increased Function and Stability As discussed, cell cycle exit is required and potentially sufficient for commitment to a specific cell lineage and also promotes functional maturation. To test this, the progression of the cell cycle was inhibited using compounds which interfere with DNA replication. The progression to S-phase can be inhibited at different stages of the cell cycle. DNA replication is licensed in the G1 phase of the cell cycle by binding to DNA with origin recognition complex and followed by recruitment of Cdc6, Cdt1 and MCM2-7 sequentially to form pre-replication complex at origins. At the G1/S transition, the MCM complex with helicase activity is activated and unwinds the double strands with assistance of topoisomerase. DNA replication forks are established. After initiation, replication proceeds bi-directionally away from origins (Sclafani and Holzen, 2007). Inhibition of DNA replication can be achieved by blocking any of these sequential events occurring before and during replication, and by DNA damage.

As shown herein DNA replication inhibition in G1 halted cell cycle progression of pancreatic progenitors, leading to an increase in differentiation efficiency of beta cells and to greater functionality in vitro measured by glucose stimulated insulin secretion. Agents which inhibit cell cycle progression in the late G1 and inhibit entry into S-phase were the most effective in promoting beta cell differentiation, while agents that affect early G1 phase were effective but less so. See Example 6.

Upon transplantation, DNA replication inhibitor treated beta cells demonstrated higher human C-peptide secretion, greater responsiveness to glucose level changes, and protected mice from diabetes without the formation of teratomas or cystic structures. See Examples 9 and 10. Therefore, inhibition of DNA replication during stem cell differentiation toward beta cells is an efficient method to ensure consistency in the generation of beta cells, useful for cell replacement to treat diabetes.

The method of the invention has been applied to beta cells, but is not unique to beta cells, as the same cellular principles apply to other terminally differentiated cell types, including but not limited to neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

Thus, the method can be used with any differentiation protocol to obtain any mature differentiated cell.

The methods and systems set forth herein generate a defined and reproducible cell population that is fully functional upon transplantation. Furthermore, the methods and systems set forth herein provide a substantially homogenous population of differentiated cells.

Generally agents which inhibit cell cycle progression in the G1 phase can be used in embodiments of the present invention. Agent which inhibit the cell cycle progression in the early G1 phase can be used in the embodiments of the present invention. Agents which inhibit the cell cycle progression in the late G1 and inhibit entry into the S-phase can be used in embodiments of the present invention.

It is within the skill of the art to recognize that any agent which interferes with DNA replication can be used in embodiments of the methods of the invention, in particular DNA replication inhibition in G1, and more particular inhibition in the late G1. Several agents representing many types agents of interference with DNA replication are exemplified herein and showed to an increase in differentiation efficiency of cells and to greater functionality in vitro and in vivo. These included the following:

Pyridostatin (PDS) stabilizes G-quadruplexes and arrests cell cycle (Moruno-Manchon et al., 2017; Zimmer et al., 2016); Cisplatin (Cis) induces DNA damage via DNA cross link and low dose arrests cells at S phase (Qin and Ng, 2002; Wagner and Karnitz, 2009); E2F inhibitor (E2Fi) inhibits the master transcription factors involved in S phase entry (Ma et al., 2008; Pardee et al., 2004; Rouaud et al., 2018); Etoposide (Eto) is a topoisomerase inhibitor and stops the unwind of the DNA helix during replication (Cliby et al., 2002; Korwek et al., 2012; Nam et al., 2010; Smith et al., 1994); Ciprofloxacin (Cipro) inhibits MCM2-7 replicative helicase at replication origin (Simon et al., 2013); A485 inhibits p300, a histone acetylase, and arrests the cell cycle and inhibits p300 dependent transcription (Lasko et al., 2017). RL5a arrests the cell cycle by inhibiting replication origin licensing (Gardner et al., 2017).

Agents which can be used in the methods of the invention include but are not limited to the following classes of molecules:

inhibitors of DNA polymerase, such as aphidicolin and gemcitabine;

compounds that stabilize G4 structures and arrest cell cycle, such as pyridostatin and TMPyP4;

inhibitors of the master transcription factors involved in S phase entry, such as E2F inhibitor; DNA helicase inhibitors, such as of WRN including WRN NSC 19630 and WRN NSC 671145, and BLM, including BLM ML216, and DNA2 including DNA2 C5 and DNA2 NSC-105808, and DDX;

topoisomerase inhibitors, such as etoposide, doxorubicin, topotecan and irinotecan;

a CDK2 inhibitor with arrests cells at early G1 phase origin;

inhibitors of MCM2-7 replicative helicase, such as ciprofloxacin;

inhibitors of MCM 4/6/7 replicative helicase, such as heliquinomycin;

inhibitors of RecQ helicases, such as RECQL1, RECQL4 and RECQL5;

inhibitors of histone acetylases, such as small molecules A485 and C646 (inhibitor of p300 and Creb-binding protein (CBP)), curcumin, garcinol, and 5-chloro-2-(4-nitrophenyl)-3(2H)-isothiazolone;

inhibitors of replication origin licensing, such as RL5a; and

DNA damaging agents, such as cisplatin or derivatives, chlorambucil, cyclophosphamide, alkylating agents, such as temozolomide (TMZ), 5-fluorouracil, and irradiation.

Specific agents that induce stalling of DNA replication in a site and cell type specific manner also include PNA oligos that stably bind to DNA at specific sites of the genome It is also within the skill of the art to determine the amount of agent to be used in the methods of the invention. By way of example, aphidicolin was used in amounts of about 0.1 μM, 0.5 μM and 1 μM. However, amounts ranging from about 0.05 μM to about 3 μM can be used. Cisplatin was used in an amount of about 2.5 μM, however, a range of about 1 μM to about 5 μM can be used. Ciprofloxacin was used in an amount of about 100 μM, however, a range of about 50 μM to about 150 μM can be used. Pyridostatin was used in an amount of about 10 μM, however, a range of about 5 μM to about 20 μM can be used. E2F inhibitor was used in an amount of about 10 μM, however, a range of about 5 μM to about 20 μM can be used. A485 was used in an amount of about 0.05 μM, however, a range of about 0.02 μM to about 0.1 μM can be used. RL5a was used in an amount of about 2 μM, however a range of about 1 μM to about 4 μM can be used. Etoposide was used in an amount of about 2 μM, however a range of about 1 μM to about 4 μM can be used.

In some embodiments, the cells are contacted or incubated with the agent or agents at the stage where the cells have differentiated into progenitor cells and are ready to differentiate into mature cells (e.g., step 6 in Table 1), such as endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes, e.g., the last step of the differentiation protocol or method. Progenitor cells include but are not limited to endocrine, endothelial, satellite cells, intermediate progenitor cells, radial glial cells, bone marrow stromal cells, periosteum cells, and blast cells. This step can be from about day 10 to about day 30 up to about day 60 of a differentiation protocol.

In some embodiments, the cells are contacted or incubated with the agents at about day 15 of the differentiation protocol, for about five days to about one week to about two weeks. In some embodiments, the cells are contacted or incubated with the agents at about day 20 of the differentiation protocol, for about one week to about two weeks. In some embodiments, the cells are contacted or incubated with the agents at early stage of differentiation of progenitor cell to mature differentiated cell which can be from about day 15 to about day 20. In some embodiments, the cells are contacted or incubated with the agents at the late stage of differentiation of progenitor cell to mature differentiated cell which can from about day 20 to about day 27. In some embodiment, the cells are contacted or incubated with the agents for the entire duration of differentiation of progenitor cell to mature differentiated cell which can be from about day 15 to about day 27 up to about day 60.

In some embodiments, the contacting or incubating of the cells with the various agents is accomplished by culturing the cells in media comprising the agents. Any media that is used for differentiating and culturing the cells of choice can be used in the methods of the invention.

The present invention also includes systems for practicing the methods of the invention for obtaining stable differentiated cells from hPSCs. These systems can include subsystems wherein the subsystems include differentiation medium and agents which interfere with DNA replication to induce cell exit.

Cells

Embodiments of the present invention include cells. These cells are unique and have a variety of therapeutic and other uses. Thus, the present invention included various solutions, compositions and/or preparations, including pharmaceutical compositions comprising the cells of the invention.

In some embodiments, the invention includes a specific mature differentiated cell or cells obtained by the any of methods described herein. In some embodiments, the specific mature cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In some embodiments, these cells have markers characteristic of a specific mature differentiated cell. In some embodiments, the cells are positive for cell markers C-peptide and NKX6.1 (mature pancreatic cells). In some embodiments, the cells are positive for cell markers NKX2.1, FOXA2, and SOX2 (mature lung cells). In some embodiments, the cells are positive for cell markers EPCAM and ITGβ4 (mature esophageal cells).

The cells of the present invention include specific mature cells differentiated from a pluripotent stem cell, a substantially homogenous population of specific mature cells differentiated from a pluripotent stem cell, and compositions comprising any of these cells of the invention, including pharmaceutical compositions and cryopreserved compositions. The invention also includes in some embodiments, cell culture comprising any of the cells of the invention. In some embodiments, the specific mature cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

Thus, one aspect of the present invention are the specific mature cells differentiated from a pluripotent stem cell suitable for administration, transplantation and grafting into a subject produced by any of the methods of the invention as described herein. In some embodiments, the specific mature cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In another aspect, provided herein is a composition comprising the specific mature cells differentiated from a pluripotent stem cell suitable for administration, transplantation and grafting into a subject produced by any of the methods of the invention as described herein. In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes. In some embodiments, the composition is a pharmaceutical composition further comprising any pharmaceutically acceptable carrier or excipient.

In certain embodiments, the composition or pharmaceutical composition comprises at least 10,000, at least 50,000, at least 100,000, at least 500,000, at least $1\times10^6$, at least $5\times10^6$, at least $1\times10^7$, at least $5\times10^7$, at least $1\times10^8$, at least $5\times10^8$, at least $1\times10^9$, at least $5\times10^9$, or at least $1\times10^{10}$ specific mature cells differentiated from a pluripotent stem cell suitable for administration, transplantation and grafting into a subject produced by any of the methods of the invention as described herein. In some embodiments, the specific mature cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In certain embodiments, the invention provides a cryopreserved composition of the specific mature cells differentiated from a pluripotent stem cell suitable for administration, transplantation and grafting into a subject produced by any of the methods of the invention as described herein. In some embodiments, the cryopreserved composition comprises at least 10,000, at least 50,000, at least 100,000, at least 500,000, at least $1\times10^6$, at least $5\times10^6$, at least $1\times10^7$, at least $5\times10^7$, at least $1\times10^8$, at least $5\times10^8$, at least $1\times10^9$, at least $5\times10^9$, or at least $1\times10^{10}$ cells differentiated from a pluripotent stem cell suitable for transplantation and grafting into a subject produced by the methods of the invention as described herein. In some embodiments, the specific mature cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In certain embodiments, the invention provides for cell culture comprising the specific mature cells differentiated from a pluripotent stem cell produced by any of the methods of the invention as described herein. In some embodiments, the cell culture comprises at least $1\times10^7$, at least $5\times10^7$, at least $1\times10^8$, at least $5\times10^8$, at least $1\times10^9$, at least $5\times10^9$, or at least $1\times10^{10}$ specific mature cells differentiated from a pluripotent stem cell suitable for administration, transplantation and grafting into a subject produced by the methods of the invention as described herein. In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In certain embodiments, the invention provides the therapeutic use of the specific mature cells differentiated from a pluripotent stem cell suitable for administration, transplantation and grafting into a subject produced by any of the methods of the invention as described herein, and compositions, solutions and cell cultures comprising such cells. In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In other embodiments, the invention provides for a population of substantially homogenous specific mature cells differentiated from a pluripotent stem cell suitable for administration, transplantation and grafting into a subject produced by any of the methods of the invention as described herein. In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes. In some embodiments, the population of cells comprises at least about 90%, 91%, 92%, 93%, 94%, 95%, 96%, 97%, 98%, or 99% differentiated cells.

In another aspect, provided herein is a composition comprising the population of substantially homogenous specific mature cells differentiated from a pluripotent stem cell suitable for administration, transplantation and grafting into a subject produced by any of the methods of the invention as described herein. In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes. In some embodiments, the composition is a pharmaceutical composition further comprising any pharmaceutically acceptable carrier or excipient.

In certain embodiments, the composition or pharmaceutical composition comprises at least 10,000, at least 50,000, at least 100,000, at least 500,000, at least $1 \times 10^6$, at least $5 \times 10^6$, at least $1 \times 10^7$, at least $5 \times 10^7$, at least $1 \times 10^8$, at least $5 \times 10^8$, at least $1 \times 10^9$, at least $5 \times 10^9$, or at least $1 \times 10^{10}$ specific mature cells differentiated from a pluripotent stem cell suitable for administration, transplantation and grafting into a subject produced by any of the methods of the invention as described herein.

In certain embodiments, the invention provides a cryopreserved composition of the population of substantially homogenous specific mature cells differentiated from a pluripotent stem cell suitable for transplantation and grafting into a subject produced by any of the methods of the invention as described herein. In certain embodiments, the cryopreserved composition comprises at least 10,000, at least 50,000, at least 100,000, at least 500,000, at least $1 \times 10^6$, at least $5 \times 10^6$, at least $1 \times 10^7$, at least $5 \times 10^7$, at least $1 \times 10^8$, at least $5 \times 10^8$, at least $1 \times 10^9$, at least $5 \times 10^9$, or at least $1 \times 10^{10}$ specific mature cells differentiated from a pluripotent stem cell suitable for administration, transplantation and grafting into a subject produced by the methods of the invention as described herein. In some embodiments, the specific mature cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In certain embodiments, the invention provides for cell culture comprising population of substantially homogenous specific mature cells differentiated from a pluripotent stem cell produced by any of the methods of the invention as described herein. In some embodiments, the cell culture comprises at least $1 \times 10^7$, at least $5 \times 10^7$, at least $1 \times 10^8$, at least $5 \times 10^8$, at least $1 \times 10^9$, at least $5 \times 10^9$, or at least $1 \times 10^{10}$ cells differentiated from a pluripotent stem cell suitable for administration, transplantation and grafting into a subject produced by the methods of the invention as described herein. In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

In certain embodiments, the invention provides the therapeutic use of the population of substantially homogenous specific mature cells differentiated from a pluripotent stem cell suitable for transplantation and grafting into a subject produced by any of the methods of the invention as described herein, and compositions, solutions and cell cultures comprising such cells. In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteocytes.

The cells disclosed herein can be preserved, for example, cryopreserved for later use. Methods for cryopreservation of cells are well known in the art. For example, the pancreatic endocrine cells can be prepared in a form that is easily administrable to an individual. For example, provided herein are cells that are contained within a container that is suitable for medical use. Such a container can be, for example, a sterile plastic bag, flask, jar, or other container from which the cells can be easily dispensed.

The various cells of the invention can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 5-10% (v/v). Cryopreservation medium may comprise additional agents, for example, methylcellulose and/or glycerol. HES-MSC are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

Pancreatic endocrine cells are exemplified herein and are particularly useful in treating and preventing diabetes. These cells can be positive for cell markers C-peptide and NKX6.1.

Pharmaceutical Compositions

As discussed above, one embodiment of the present invention is a pharmaceutical composition comprising a therapeutically effective amount of a cell, cells or population of cells of the invention and a pharmaceutically acceptable carrier. The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

These compositions can take the form of solutions, suspensions, emulsions, tablets, pills, capsules, powders, sustained-release formulations, cachets, troches, lozenges, dispersions, suppositories, ointments, cataplasms (poultices), pastes, powders, dressings, creams, plasters, patches, aerosols, gels, liquid dosage forms suitable for parenteral administration to a patient, and sterile solids (e.g., crystalline or amorphous solids) that can be reconstituted to provide liquid dosage forms suitable for parenteral administration to a patient. Such compositions will contain a therapeutically effective amount of the compound, preferably in purified form, together with a suitable form of carrier so as to provide the form for proper administration to the patient. The formulation should suit the mode of administration.

Pharmaceutical compositions adapted for nasal and pulmonary administration may comprise solid carriers such as powders which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for parenteral administration include aqueous and non-aqueous sterile injectable solutions or suspensions, which may contain anti-oxidants, buffers, baceriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Selection of a therapeutically effective amount will be determined by the skilled artisan considering several factors which will be known to one of ordinary skill in the art. Such factors include the particular form of the cells and other parameters such as bioavailability, which will have been established during the usual development procedures typically employed in obtaining regulatory approval for a pharmaceutical composition. Further factors in considering the amount include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise amount should be decided according to the judgment of the person of skill in the art, and each patient's circumstances, and according to standard clinical techniques.

A standard therapeutically effective amount of cells to be administered, transplanted or grafted into a subject is about $1 \times 10^9$. More specifically for pancreatic cells, about 250,000 to about $1 \times 10^6$ stem cell derived islet clusters which contain about several million cells can be administered, transplanted or grafted into a subject.

Therapeutic Uses

The novel method described herein for the generation of mature stable differentiated cells from stem cells, and the cells and substantially homogenous population of cells generated from any method of the invention, provide new therapies for many diseases.

In particular, the novel methods described herein for the generation of pancreatic endocrine cells from stem cells, and the cells and substantially homogenous population of cells generated from this method, provide new therapies for diabetes.

Thus, one embodiment of the present invention is a method of treating or preventing diabetes comprising the steps of administering, transplanting or grafting a therapeutically effective amount of the cells of the present invention, a solution comprising the cells of the invention, a composition comprising the cells of the invention, cell culture comprising the cells of the invention or a pharmaceutical composition comprising the cells of the invention as described herein, to the subject in need thereof. Diabetes would include type 1, type 2 and monogenetic forms. The subject is preferably a mammal or avian, and most preferably human. The cells, compositions, cell culture or pharmaceutical compositions can comprise pancreatic endocrine cells made by the methods of the invention, or a population of substantially homogenous pancreatic endocrine cells made by the methods of the invention.

A further embodiment of the present invention is a method of treating or preventing disease comprising the steps of administering, transplanting or grafting a therapeutically effective amount of the cells of the present invention, a solution comprising the cells of the invention, a composition comprising the cells of the invention, cell culture comprising the cells of the invention or a pharmaceutical composition comprising the cells of the invention as described herein, to the subject in need thereof. The cells, compositions, cell culture or pharmaceutical compositions can comprise specific mature differentiated cells made by the methods of the invention, or a population of substantially homogenous specific mature differentiated cells made by the methods of the invention.

In some embodiments, the specific cells differentiated from a pluripotent stem cell are chosen from the group consisting of pancreatic endocrine cells, pancreatic cells, and endocrine cells, neurons, astrocytes, oligodendrocytes, retinal epithelial cells (RPE), epidermal cells, hair cells, keratinocytes, hepatocytes, intestinal epithelial cells, lung alveolar cells, hematopoietic cells, endothelial cells, cardio-myocytes, smooth muscle cells, skeletal muscle cells, car-tilage cells, bone cells, renal cells, adipocytes, chondrocytes, and osteocytes.

Kits

The present invention also provides kits comprising the components of the combinations of the invention in kit form.

In one embodiment, the kit includes reagents for practic-ing any of the methods of the invention for obtaining stable differentiated cells from hPSCs including differentiation medium and agents which interfere with DNA replication to induce cell exit.

In further embodiments, a kit can include the pancreatic cells obtained by the current methods and systems of the invention. The kit can also comprise reagents for culturing the cells.

In further embodiments, a kit can include a pharmaceu-tical composition comprising the pancreatic cells obtained by the current methods and systems of the invention.

In further embodiments, a kit can include a cryopreserved composition the pancreatic cells obtained by the current methods and systems of the invention.

In further embodiments, a kit can include the specific mature differentiated cells obtained by the current methods and systems of the invention. The kit can also comprise reagents for culturing the cells.

In further embodiments, a kit can include a pharmaceu-tical composition comprising the specific mature differenti-ated cells obtained by the current methods and systems of the invention.

In further embodiments, a kit can include a cryopreserved composition comprising the specific mature differentiated cells obtained by the current methods and systems of the invention.

In some embodiments, the specific mature cells differen-tiated from a pluripotent stem cell are chosen from the group consisting of neurons, astrocytes, oligodendrocytes, retinal epithelial cells (RPE), epidermal cells, hair cells, keratino-cytes, hepatocytes, intestinal epithelial cells, lung alveolar cells, hematopoietic cells, endothelial cells, cardiomyocytes, smooth muscle cells, skeletal muscle cells, cartilage cells, bone cells, renal cells, adipocytes, chondrocytes, and osteo-cytes.

The kits can further include a package insert including information concerning the pharmaceutical compositions and dosage forms in the kit. For example, the following information regarding a combination of the invention may be supplied in the insert: how supplied, proper storage conditions, references, manufacturer/distributor information and patent information.

EXAMPLES

The present invention may be better understood by ref-erence to the following non-limiting examples, which are presented in order to more fully illustrate the preferred embodiments of the invention. They should in no way be construed to limit the broad scope of the invention.

Example 1—Materials and Methods for Examples 2-10

Human Pluripotent Stem Cell Culture

Human pluripotent stem cells were cultured and main-tained in feeder-free plates with stemflex medium as described. Three cell lines were involved in this study as shown in Table 2: MEL1 is human embryonic stem cell line; 1023A is a human induced pluripotent stem cell line repro-grammed from a skin fibroblast biopsied of a healthy control; and 1018E is a human induced pluripotent stem cell line reprogrammed from a skin fibroblast biopsied from a female type 1 diabetes patient. All human subjects research was reviewed and approved by the Columbia University Institutional Review Board, and the Columbia University Embryonic Stem Cell Committee.

Beta Cell Differentiation from Human Pluripotent Stem Cells

Beta cells differentiated from human pluripotent stem cell lines as described in Example 2 (Sui et al., 2018b). Indicated compounds that function as cell cycle inhibitors were added individually from day 15 to day 27 with concentration listed below:

The DNA replication inhibitors used in this study: 0.1 µM, 0.5 µM and 1 µM Aphidicolin (A0781, Sigma-Aldrich); 2.5 µM Cisplatin (232120, EMD Millipore); 100 µM Cipro-floxacin (S2027, Selleck Chemicals); 10 µM Pyridostatin (S7444, Selleck Chemicals); 10 µM E2F Inhibitor (324461, EMD Millipore); 0.05 µM A485 (6387, Tocris); 2 µM RL5a (SML2187, Sigma-Aldrich); and 2 µM Etoposide (E55500, Research Products International). Indicated compounds were added individually from day 15 to day 27 with indi-cated concentration.

Gene Expression

Total RNA was extracted from the cells at beta cell stage (d27) from different conditions using a RNeasy Mini Kit (Cat. No. 74106, QIAGEN). The total RNA was reverse transcribed into cDNA using iScript™ Reverse Transcrip-tion Supermix (Cat. No. 170-8841, Bio-Rad), and the cDNA were sequentially used as template with SsoFast™ EvaGreen® Supermix (Cat. No. 172-5202, Bio-Rad) for quantitative realtime PCR. The primers used in PCR are listed in Table 3.

Immunocytochemistry

Clusters at d27 were collected and fixed with 4% paraformaldehyde (PFA). The following steps were per-formed according to published method (Sui et al., 2018b). Primary antibodies are listed in Table 4 and secondary antibodies are listed in Table 5. Pictures were taken under OLYMPUS 1×73 fluorescent microscope or ZEISS LSM 710 confocal microscope.

Flow Cytometry

The beta cell clusters were dissociated using TrypLE™ Express into single cells. Cells were fixed with 4% PFA for 10 min and followed by permeabilization at −20° C. with cold methanol for 10 min. Primary antibodies were added at a dilution of 1:100 in autoMACs Rinsing Solution (Cat. No. 130-091-222, Miltenyi Biotec) containing 0.5% BSA at 4° C. for 1 hour. Secondary antibodies were added at a dilution of 1:500 at room temperature for 1 hour. The cells were filtered with BD Falcon 12×75 mm tube with cell strainer cap (Cat. No. 352235, BD) and subsequently analyzed by flow cytometer. Data were analyzed using Flowjo software. Negative controls were performed by only adding secondary antibodies.

Static Glucose Stimulated C-Peptide Secretion

Krebs Ringer buffer (KRB) was prepared by addition of 129 mM NaCl, 4.8 mM KCl, 2.5 mM CaCl$_2$), 1.2 mM MgSO$_4$, 1 mM Na$_2$HPO$_4$, 1.2 mM KH$_2$PO$_4$, 5 mM NaHCO$_3$, 10 mM HEPES and 0.1% BSA in deionized water and was sterilized using 0.22 μm filter. 2 mM and 20 mM glucose solution were prepared in KRB for low glucose and high glucose challenge of sc-beta cell clusters. 10-20 sc-beta cell clusters (about 5×105 cells) were collected from control and cells treated with cell cycle inhibitors including APH and treated conditions and pre-incubated in 500 μl low glucose solution for 1 hour. Clusters were then washed once with low glucose solution and sequentially incubated in 200 μl of low glucose and then high glucose solution for 30 minutes. 130 μl supernatant of each condition were collected. Supernatants containing secreted C-peptide stimulated by low and high glucose were processed using Mercodia Ultrasensitive Human C-peptide ELISA kit. Fold changes of C-peptide secretion before and after glucose stimulation were calculated.

Transplantation and In Vivo Assay 8-10 weeks old male immuno-compromised mice (NOD.Cg-Prkdcscid Il2rgtm1Wj1/SzJ (NSG) from Jackson laboratories, Cat. No. 005557) were used for transplantation. For intra leg muscle transplantation, 1-2 million cells were collected and settled in tube with 50 μl Matrigel. All animal protocols were approved by the Institutional Animal Care and Use Committee in Columbia University.

The human C-peptide levels in mouse serum were measured every two weeks in the fed state. Intraperitoneal glucose tolerance test was performed by fasting overnight and injecting 2 g/kg D-glucose solution at 2 weeks after mouse beta cells were ablated with one high dose (150 mg/kg) Streptozocin (Cat. No. S0130-1G, Sigma-Aldrich). Blood was collected in heparin-coated tube at fed state, fasting and 30 min after glucose injection. Plasma were collected by centrifuging tubes at 2000 g for 15 minutes at 4° C. The supernatants were collected for C-peptide and insulin detection with Mercodia M-Plex™ ARRAY Chemiluminescent Mercodia Beta Kit. Blood glucose levels was measured at fed state, fasting and every 30 minutes after glucose injection for 2 hours.

Western Blotting

The sorted GFP positive and negative cells with and without cell cycle inhibitor (e.g., APH) treatment were lysed with RIPA buffer. Protein was quantified with Pierce BCA protein assay kit. 20 ug of protein was loaded on 4-20% Mini-PROTEAN TGS Precast Protein Gels (Cat. No. 4561094, Bio-Rad) from each condition and ran at 100 V for 1 hour followed by transferring protein on PVDF membrane. The membrane was blocked with 3% BSA in TBST for 1 hour at RT, incubate with primary antibodies diluted in TBST with 3% BSA overnight on a shaker. After washing with TBST, the membrane was incubated with secondary antibodies diluted in TBST with 3% non-fat dry milk powder for 1 hour at room temperature. The image was taken using ChemiDoc Imaging Systems (Bio-Rad).

Statistical Analysis

Data were analyzed by unpaired t test and by one-way ANOVA followed by Tukey's multiple comparison test (GraphPad Prism 6, GraphPad Software, Inc., La Jolla, CA) and expressed as mean±standard deviation (SD). The differences observed were considered statistically significant at the 5% level and were displayed on the figures as follows: $*p<0.05$, $p<0.01$, $*p<0.001$, $****p<0.0001$.

TABLE 2

Information of cell lines used

| Stem cell line ID | Repro-gramed method | Origin | Sex | Diagnosis | Reference |
|---|---|---|---|---|---|
| MEL1 (INS$^{GFP/W}$hESC) | n/a | Inner cell mass | Male | n/a | (Micallef et al., 2012) |
| 1023A | mRNA | fibro-blast | Male | Healthy control | |
| 1018E | mRNA | fibro-blast | Female | T1D | (Yamada et al., 2014) |

TABLE 3

Primers used for quantitative realtime PCR at different stage during the differentiation.

| Gene | Forward | Reverse |
|---|---|---|
| OCT4 | TGGGCTCGAGAAGGATGTG (SEQ ID NO: 1) | GCATAGTCGCTGCTTGATCG (SEQ ID NO: 2) |
| SOX17 | GGCGCAGCAGAATCCAGA (SEQ ID NO: 3) | CCACGACTTGCCCAGCAT (SEQ ID NO: 4) |
| FOXA2 | GGGAGCGGTGAAGATGGA (SEQ ID NO: 5) | TCATGTTGCTCACGGAG-GAGTA (SEQ ID NO: 6) |
| PDX1 | CCCTGGGTGACCACTAAACC (SEQ ID NO: 7) | CACAGCCTCTACCTCGGAAC (SEQ ID NO: 8) |
| NKX6.1 | ATTCGTTGGGGATGACAGAG (SEQ ID NO: 9) | CGAGTCCTGCTTCTTCTTGG (SEQ ID NO: 10) |
| NGN3 | TCTTTTCTCCTTTGGGGCTGG (SEQ ID NO: 11) | TCTCACGGGTCACTTGGACA (SEQ ID NO: 12) |
| SUR1 | GTTCCAGCAGAAGCTTCTCG (SEQ ID NO: 13) | GCTGAAATTCTCCCCGCCTT (SEQ ID NO: 14) |
| INS | TTCTACACACCCAAGACCCG (SEQ ID NO: 15) | CAATGCCACGCTTCTGC (SEQ ID NO: 16) |
| GLU | AAGTTCCCAAAGAGGGCTTG (SEQ ID NO: 17) | AGCTGCCTTGTACCAGCATT (SEQ ID NO: 18) |

TABLE 4

Primary antibody list

| Antibody | Species | Dilution | Company | Catalog number |
|---|---|---|---|---|
| SOX17 | Goat | 1:100 | R&D Systems | AF1924 |
| FOXA2 | Rabbit | 1:400 | Cell Signaling Technology | 3143S |
| PDX1 | Goat | 1:100 | R&D Systems | AF2419 |
| NKX6.1 | Mouse | 1:300 | Developmental Studies Hybridoma Bank | F55A10 |
| C-peptide | Rat | 1:100 | Developmental Studies Hybridoma Bank | GN-ID4 |
| Glucagon | Guinea Pig | 1:200 | Takara | M182 |
| MafA | Rabbit | 1:100 | Abcam | ab26405 |
| Somatostatin | Rabbit | 1:1000 | Millipore | AB5494 |
| Chromogranin A | Mouse | 1:100 | Millipore | MAB5268 |

TABLE 4-continued

Primary antibody list

| Antibody | Species | Dilution | Company | Catalog number |
|---|---|---|---|---|
| Synaptophysin | Rabbit | 1:100 | Novus Biologicals | NB300-653 |
| Ki67 | Rabbit | 1:200 | Abcam | ab16667 |
| CK19 | Rabbit | 1:200 | Abcam | ab52625 |

TABLE 5

Secondary antibody list

| Antibody | Dilution | Company | Catalog number |
|---|---|---|---|
| Donkey Anti-Rat Alexa Fluor ® 488 | 1:500 | Jackson ImmunoResearch Laboratories | 712-545-153 |
| Donkey Anti-Rabbit DyLight ™ 405 | 1:500 | Jackson ImmunoResearch Laboratories | 711-475-152 |
| Donkey Anti-Mouse DyLight ™ 405 | 1:500 | Jackson ImmunoResearch Laboratories | 715-475-151 |
| Donkey Anti-Guinea Pig Alexa Fluor ® 647 | 1:500 | Jackson ImmunoResearch Laboratories | 706-605-148 |
| Donkey Anti-Rabbit Alexa Fluor ® 555 | 1:500 | Life Technologies | A-31572 |
| Donkey Anti-Goat Alexa Fluor ® 555 | 1:500 | Life Technologies | A-21432 |
| Donkey Anti-Mouse Alexa Fluor ® 488 | 1:500 | Life Technologies | A-21202 |
| Donkey Anti-Mouse Alexa Fluor ® 555 | 1:500 | Life Technologies | A-31570 |
| Donkey Anti-Goat Alexa Fluor ® 488 | 1:500 | Life Technologies | A-11055 |
| Donkey Anti-Rabbit Alexa Fluor ® 488 | 1:500 | Life Technologies | A-21206 |
| Goat Anti-Rat Alexa Fluor ® 555 | 1:500 | Life Technologies | A-21434 |

Example 2—Stepwise Differentiation of Pancreatic Beta Cells

After 95%-100% confluence of hiPSCs was achieved, beta cell induction was initiated by using combinations of growth factors and small molecules. The differentiation steps are summarized in Table 1 (i.e., definitive endoderm induction, primitive gut tube induction, posterior foregut induction, pancreatic progenitor induction, pancreatic endocrine progenitor induction, and pancreatic beta cell induction), At the pancreatic progenitor stage, cells were cultured as organoids using AggreWell 400 6-well plate to promote cell to cell interaction.

The following steps were followed to obtain the definitive endoderm stage:

Materials

STEMdiff™ Definitive Endoderm Differentiation Kit, supplement A and supplement B (cat. No. 05110, STEMCELL Technologies)

Washing Medium (see recipe)

Primitive Gut Tube Stage Medium (see recipe)

Posterior Foregut Stage Medium (see recipe)

Pancreatic Progenitor Stage Medium (see recipe)

Cluster Medium (see recipe)

AggreWell Rinsing Solution (cat. no. 07010, STEMCELL Technologies)

TrypLE Express Enzyme (cat no. 12605-036, ThermoFisher)

DMEM plus GlutaMax (cat no. 10569-044, Life Technology)

Pancreatic Endocrine Progenitor Stage Medium (see recipe)

Pancreatic Beta Cell Stage Medium (see recipe)

At day 0-day 1

1. Thawed STEMdiff™ Definitive Endoderm Differentiation Kit.

2. Prepared definitive endoderm medium for day 1 by mixing supplement A and supplement B with definitive endoderm basal medium in a 1:100 ratio.

3. Aspirated StemFlex medium from the wells containing the cells ready for differentiation, and washed cells once by gently rocking the plate forward and backward for 5 times after adding 2 ml washing medium in each well.

4. Replaced the washing medium with the first day definitive endoderm medium (2 ml/well for 6-well plates and 0.5 ml/well for 4-well plates), and incubated for 24 hours in 37° C., 5% CO2 humidified incubator.

At day 1-day 2.5

5. Prepared the second day definitive endoderm medium by mixing supplement B with definitive endoderm basal medium in a 1:100 ratio.

6. Replaced the first day definitive endoderm medium with the second day definitive endoderm medium (2 ml/well for 6-well plates and 0.5 ml/well for 4-well plates), and incubated for 36 hours at 37° C.

At day 2.5-day 4

7. Refreshed the cells with the new second day definitive endoderm medium prepared in the last step (2 ml/well for 6-well plates and 0.5 ml/well for 4-well plates), and incubated for 36 hours at 37° C., 5% $CO_2$ humidified incubator.

The following steps were followed to obtain the primitive gut tube stage:

At day 4-day 6

8. Prepared the primitive gut tube medium.

Primitive Gut Tube Stage Medium (d4-d6)

RPMI 1640 plus GlutaMAX (Cat. No. 61870-127, Life Technology)

1% (v/v) Penicillin-Streptomycin (Cat. No. 15070-063, Thermo Fisher Scientific)

1% (v/v) B-27 Serum-Free Supplement (50×) (Cat. No. 17504044, Life Technology)

50 ng/ml FGF7 (Cat. No. 251-KG, R&D System)

Medium should be prepared freshly and used up within 3 days upon storing at 4° C. or 1 month at −20° C.

9. Washed cells with washing medium.

10. Replaced the washing medium with primitive gut tube stage medium (2 ml/well for 6-well plates and 0.5 ml/well for a 4-well plate), and incubated for 48 hours at 37° C.

The following steps were followed to obtain the posterior foregut stage:

At day 6-day 8

11. Prepared posterior foregut stage medium.

Posterior Foregut Stage Medium (d6-d8)

DMEM plus GlutaMAX (Cat. No. 10569-044, Life Technology)

1% (v/v) Penicillin-Streptomycin

1% (v/v) B-27 Serum-Free Supplement (50×)

0.25 μM KAAD-Cyclopamine (Cat. No. 04-0028, Stemgent)

2 μM Retinoic acid (Cat. No. 04-0021, Stemgent)

0.25 μM LDN193189 (Cat. No. 04-0074, Stemgent)

Medium should be prepared freshly and used up within 3 days upon storing at 4° C. or 1 month at −20° C.

12. Replaced the medium with posterior foregut stage medium (2 ml/well for 6-well plates and 0.5 ml/well for a 4-well plate), and incubated for 48 hours at 37° C.

The following steps were followed to obtain the pancreatic progenitor stage

At day 8-day 12

13. Prepared pancreatic progenitor stage medium.

Pancreatic Progenitor Stage Medium (d8-d12)

DMEM plus GlutaMAX

1% (v/v) Penicillin-Streptomycin

1% (v/v) B-27 Serum-Free Supplement (50×)

50 ng/ml EGF (Cat. No. 236-EG, R&D System)

25 ng/ml FGF7

Medium should be prepared freshly and used up within 3 days upon storing at 4° C. or 1 month at −20° C.

14. Replaced the last stage medium with pancreatic progenitor stage medium (2 ml/well for the 6-well plates and 0.5 ml/well for the 4-well plate), and incubated for 48 hours at 37° C.

15. Replaced the medium with new medium left in step 12, and incubated for another 48 hours at 37° C.

The following steps were followed to make 3D cell clusters:

At day 12-day 13

16. Calculated the amount of medium and the number of wells in AggreWell 400 6-well plate according to the experiment scale. For 2 wells of 6-well plate, 5 ml clustering medium and 1 well of AggreWell 400 6-well plate was used.

17. Pre-treated the AggreWell 400 6-well plate by adding 2 ml AggreWell Rinsing Solution in each well and centrifuge the plate at 1300×g for 5 minutes.

18. Prepared the clustering medium.

Cluster Medium (d12-d13)

DMEM plus GlutaMAX

1% (v/v) Penicillin-Streptomycin

1% (v/v) B-27 Serum-Free Supplement (50×)

1 μM ALKS inhibitor (Stemgent cat. no. 04-0015)

10 μg/ml Heparin (Cat. No. H3149, SIGMA-ALDRICH)

25 ng/ml FGF7

10 μM Y-27632, ROCK inhibitor

Medium should be prepared freshly and used up within 3 days upon storing at 4° C. or 1 month at −20° C.

19. Detached the cells at pancreatic progenitor stage using TrypLE express enzyme (0.5 ml/well) for 2 minutes at room temperature.

20. Aspirated dissociation enzyme from the plate, added 1 ml clustering medium to each well, pipeted up and down using a 1000-μl pipet and tip to detach all cells from the plate.

21. Transferred cell suspension to a 50-ml conical tube and washed the well once with 1 ml clustering medium to ensure all cells are collected and transferred to the 50-ml conical tube.

22. Aspirated AggreWell Rinsing Solution from AggreWell 400 6-well plate after centrifugation and rinsed the well with 1 ml DMEM plus GlutaMAX.

23. Aspirated DMEM plus GlutaMAX medium from the well, transferred 4 ml cell suspension to 1 well of AggreWell 400 6-well plate, and incubated the plate for 24 hours at 37° C.

The following steps were followed to obtain the pancreatic endocrine progenitor stage:

At day 13-day 15

24. Calculated the amount of medium and the number of low-attachment 6-well plates used in the following step. For 1 well of AggreWell 400 6-well plate, 7 ml pancreatic endocrine progenitor stage medium and 3 wells of low-attachment 6-well plate were used.

25. Prepared the pancreatic endocrine progenitor stage medium 1.

Pancreatic Endocrine Progenitor Stage Medium 1 (d13-d15)

RPMI plus GlutaMAX

1% (v/v) Penicillin-Streptomycin

1% (v/v) B-27 Serum-Free Supplement (50×)

1 μM thyroid hormone (T3) (Cat. No. T6397, SIGMA)

10 μM ALKS inhibitor

10 μM Zinc sulfate (Cat. No. Z4750, SIGMA-ALDRICH)

10 μg/ml Heparin (Cat. No. H3149, SIGMA-ALDRICH)

100 nM Gamma-secretase inhibitor (DBZ) (Cat. No. 565789, EMD Millipore)

10 μM Y-27632, ROCK inhibitor

Medium should be prepared freshly and used up within 3 days upon storing at 4° C. or 1 month at −20° C.

26. Resuspended the cell clusters in AggreWell 400 6-well plate with the medium in the wells and collected into 50-ml conical tube.

27. Rinsed the well with 1 ml pancreatic endocrine progenitor stage medium and transferred into the same 50-ml conical tube.

28. Pelleted the cell clusters in 50-ml conical tube by gravity for 5 minutes.

29. Aspirated supernatant from the 50-ml conical tube, replaced the medium with 6 ml pancreatic endocrine progenitor stage medium.

30. Resuspended clusters by gently pipetting up and down 2 times and transferred them into low-attachment 6-well plate (2 ml/well).

31. Shook the plate forward and backward and side to side before placing it in the incubator.

At day 15-day 20

32. Prepared the pancreatic endocrine progenitor stage medium 2.

Pancreatic Endocrine Progenitor Stage Medium 2 (d15-d20)

RPMI plus GlutaMAX

1% (v/v) Penicillin-Streptomycin

1% (v/v) B-27 Serum-Free Supplement (50×)

1 μM thyroid hormone (T3) (Cat. No. T6397, SIGMA)

10 μM ALKS inhibitor

10 μM Zinc sulfate (Cat. No. Z4750, SIGMA-ALDRICH)

10 μg/ml Heparin (Cat. No. H3149, SIGMA-ALDRICH)

100 nM Gamma-secretase inhibitor (DBZ) (Cat. No. 565789, EMD Millipore)

10 μM Y-27632, ROCK inhibitor

Agent which inhibits cell cycle e.g., 1 μM Aphidicolin (Cat. No. A0781, Sigma-Aldrich)

Medium should be prepared freshly and used up within 3 days upon storing at 4° C. or 1 month at −20° C.

33. Changed medium every other day.

The following steps were followed to obtain the pancreatic beta cell stage:

At day 20-day 27

34. Prepared the pancreatic beta cell stage medium (see recipe).

Pancreatic Beta Cell Stage Medium (d20-d27)

RPMI plus GlutaMAX

1% (v/v) Penicillin-Streptomycin

1% (v/v) B-27 Serum-Free Supplement (50×)

10% (v/v) Fetal bovine serum (Atlanta Biologicals, cat. no. S11150)

10 μM Y-27632, ROCK inhibitor

Agent which inhibits cell cycle, e.g., 1 µM Aphidicolin (Cat. No. A0781, Sigma-Aldrich)

Medium should be prepared freshly and used up within 3 days upon storing at 4° C. or 1 month at −20° C.

35. Changed medium every other day.

Washing Medium Used Throughout Protocol

RPMI 1640 plus GlutaMAX (Cat. No. 61870-127, Life Technology)

1% (v/v) Penicillin-Streptomycin

Store up to two months at 4° C.

This protocol is based on six key cellular induction steps in hPSCs: 1. A commercial definitive endoderm differentiation kit was used to activate Activin A and Wnt3a signaling pathway to give rise to 95% SOX17 and FOXA2-positive definitive endoderm cells; 2. Further induction of definitive endoderm cells to primitive gut tube with FGF7 was performed (D'Amour et al. 2006); 3. The posterior foregut tube was induced by inhibition of sonic hedgehog and the BMP4 signaling pathway and the activation of the retinoic acid pathway (D'Amour et al. 2006; Mfopou and Bouwens (2008); Mfopou et al. 2010); 4. Further committed cells to pancreatic progenitors expressing PDX1 and NKX6.1 by activation of protein kinase C pathway with EGF (Nostro et al. 2015; Sui et al. 2013); 5. Performed pancreatic endocrine lineage commitment by addition of thyroid hormone and upregulation of NGN3 expression through inhibition of Notch signaling together with blockage of the TGF beta signaling pathway with ALKS inhibitor (Rezania et al. 2014)

Figure 1B:
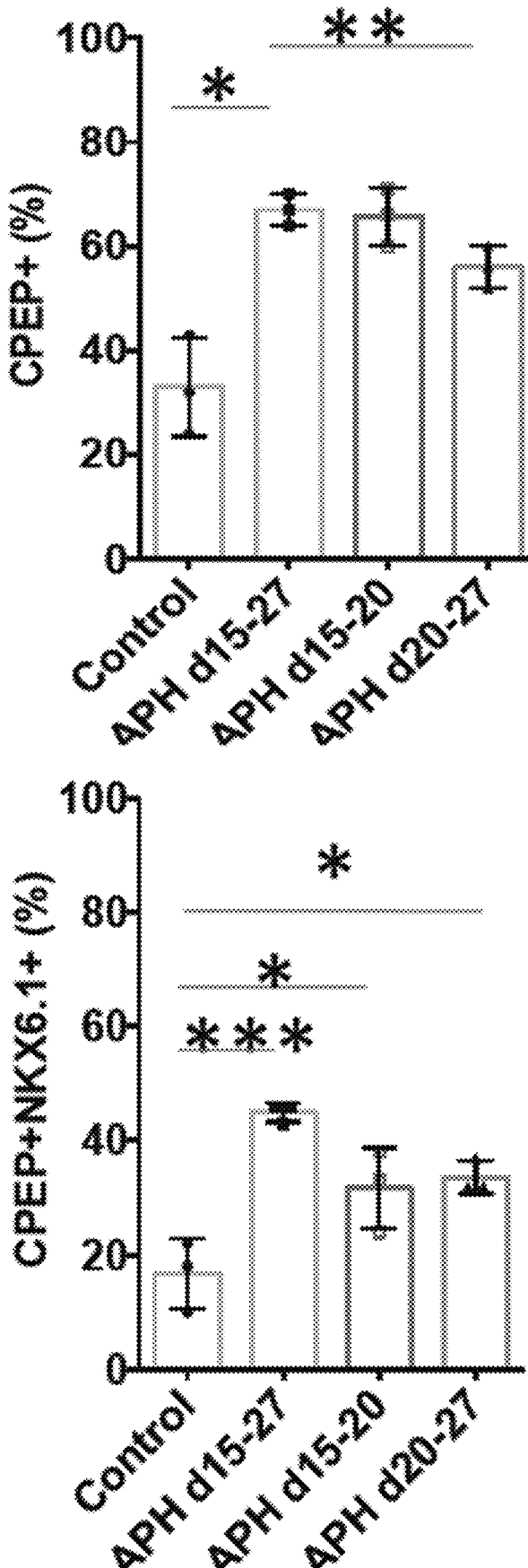
FIG. 1B are graphs quantifying the results of the flow cytometry analysis of the percentage of C-peptide positive, and C-peptide and NKX6.1 double positive cells at day 27 for the indicated conditions.
Figure 1C:
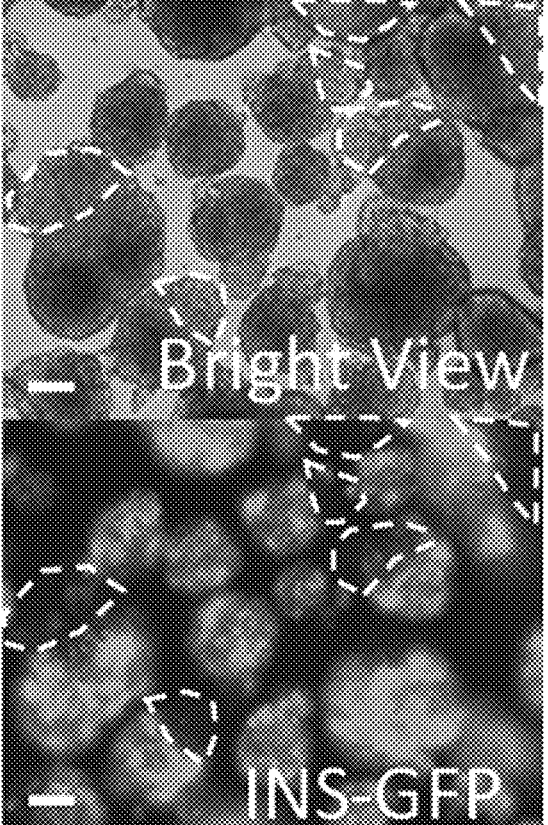
FIG. 1C are images showing the morphology of insulin positive clusters indicated by the expression of GFP, derived from control and APH group at day 27. Scale bar: 100 μm.
Figure 1C:
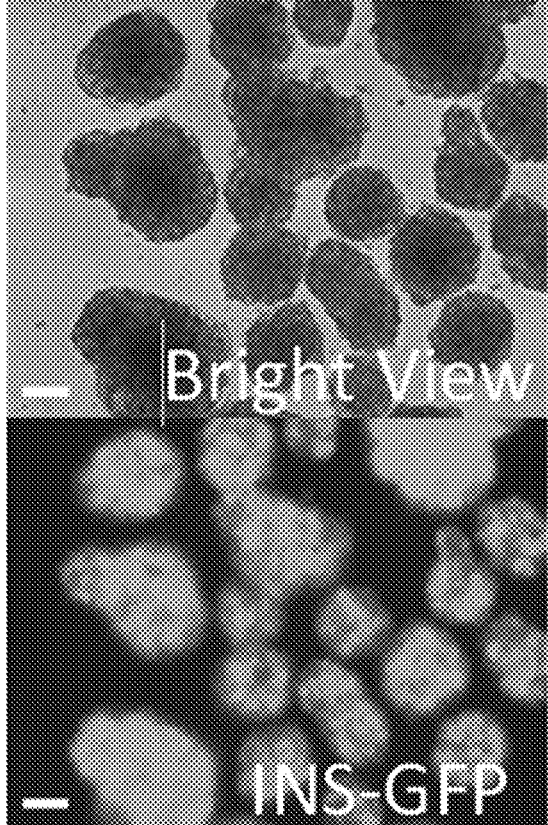
Figure 1D:
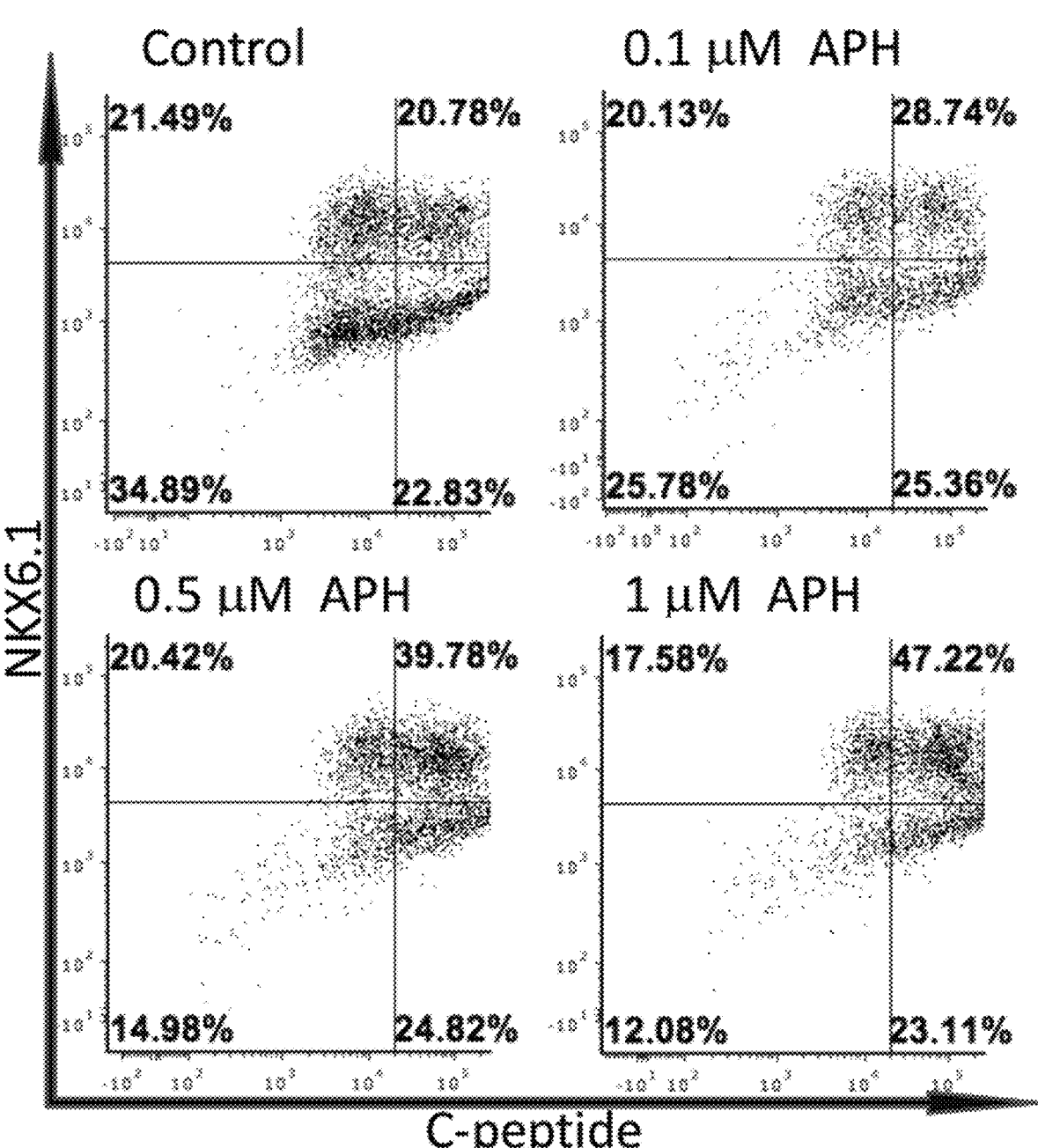
FIG. 1D are images of flow cytometry analysis of C-peptide and NKX6.1 double positive cells derived at the end of differentiation at day 27 where aphidicolin (APH) was added in the indicated amounts versus control.

Example 3—Inhibition of DNA Replication by Aphidicolin Increased the Purity of Stem Cell Derived Beta Cells Aphidicolin (APH), a DNA polymerase inhibitor, was used to inhibit DNA replication (Koundrioukoff et al., 2013). APH was added during the differentiation from day 15 (pancreatic progenitor cell (PPC) stage) until day 27 (pancreatic beta cell (PB). Different time points of treatment at early stage (d15-d20), late stages (d20-d27) and whole duration of differentiation (d15-d27) were evaluated by the percentage of C-peptide positive cells, and C-peptide and NKX6.1 double positive cells derived at the end of differentiation at day 27. Addition of APH at all indicated stages increased the proportion of C-peptide positive cells, and C-peptide and NKX6.1 dual positive cells (FIG. 1A). The most effective differentiation toward C-peptide and NKX6.1 positive cells occurred when APH was added from day 15 to day 27 (FIG. 1B). The insulin expressing cells were evenly distributed in the islet-like clusters with high percentage indicated by the expression of GFP, whereas some parts of the clusters in control remained GFP negative (FIG. 1D).

To determine the most effective concentration, cells were exposed to APH from d15-d27 at increasing concentrations, from 0.1 µM, 0.5 µM to 1 µM. Cells treated with 1 µM APH gave rise to the highest percentage of c-peptide and NKX6.1 positive cells (FIG. 1D).

Figure 1E:
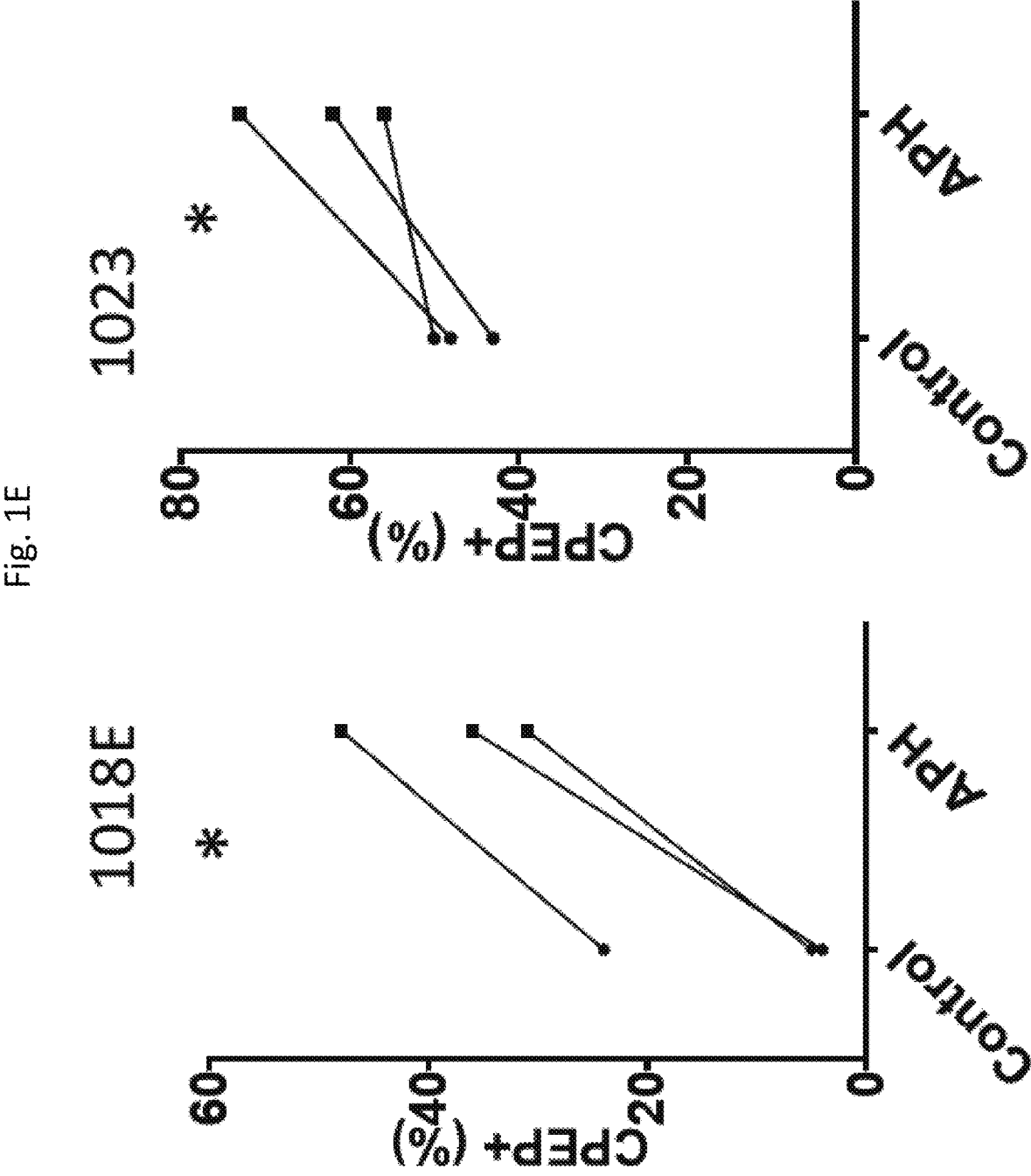
FIG. 1E show graphs of the percent of C-peptide positive cells at the end of differentiation at day 27 where aphidicolin (APH) was added from about days 15-27 versus control using two different iPSC cell lines, 1018E and 1023.

To evaluate if the positive effect of APH on the derivation of insulin expressing cells is generalized across different cell lines, two iPSC lines with different differentiation potentials were included in the study, 1018E and 1023A. 1018E was previously identified as a cell line that differentiates poorly (Sui et al. 2018a). The percentage of C-peptide positive cells was significantly upregulated after APH treatment in both cell lines (FIG. 1E). Remarkably, the poor differentiation potential of 1018E increased to the range of a differentiation competent cell line, from an average of 11% to 38%.

Therefore, APH increased the purity of stem cell derived beta cells after formation of pancreatic progenitors. Significantly, it reduced the variability of beta cell differentiation. All (n=12 independent differentiation experiments) cultures contained more than 50% C-peptide positive cells.

Figures 2, 2A:
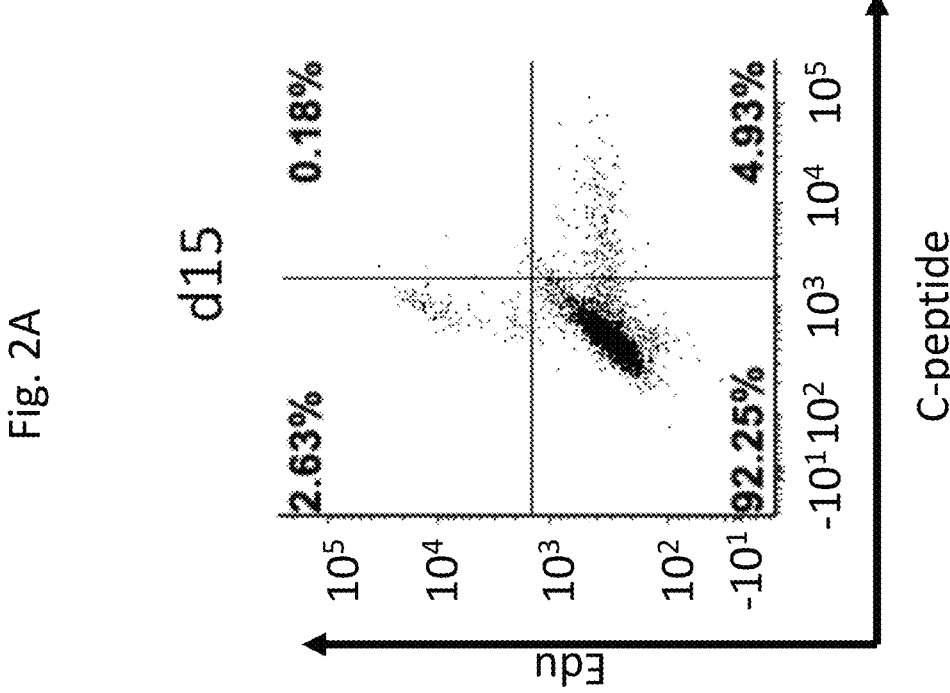
FIG. 2—Aphidicolin arrested cell cycle progression and increased beta cell differentiation efficiency.
FIG. 2A is an image of flow cytometry analysis of cell cycle progression at day 15.
Figure 2B:
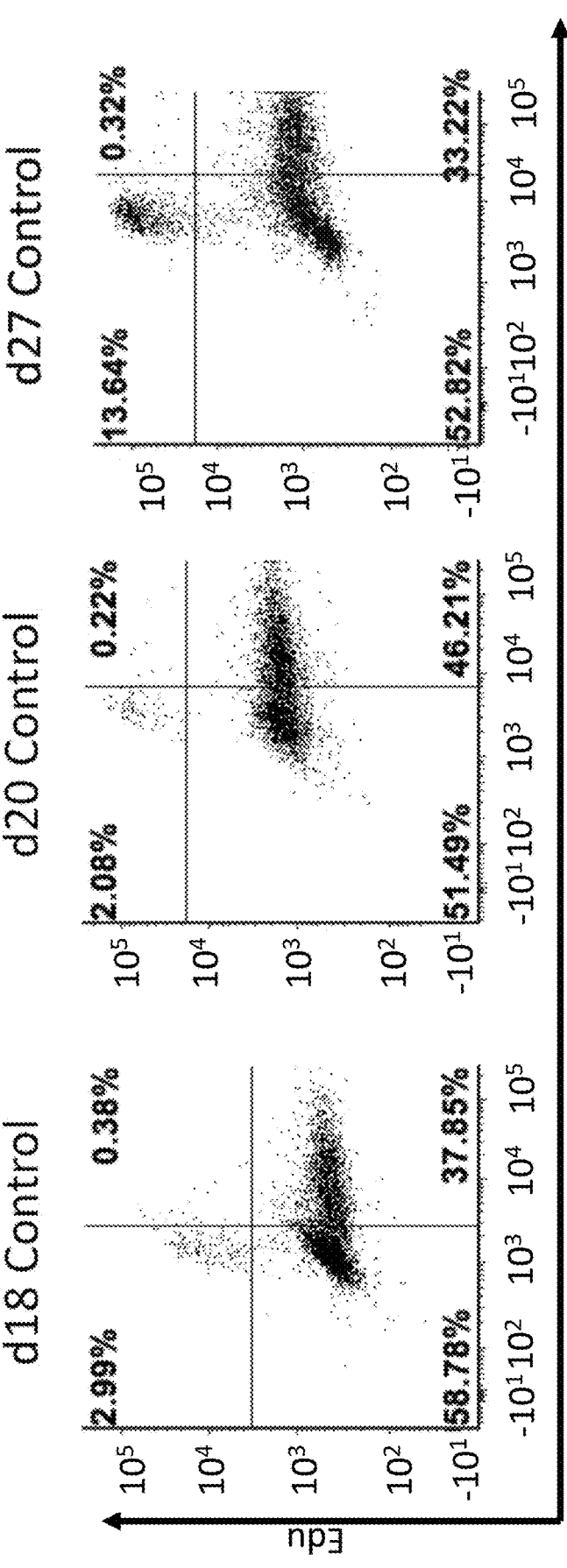
FIG. 2B are images of flow cytometry analysis of cell cycle progression day 18, day 20, and day 27 in a control (no addition of APH).
Figure 2C:
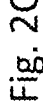
FIG. 2C are images of flow cytometry analysis of cell cycle progression day 18, day 20, and day 27, where aphidicolin (APH) was added from about days 15-27.

Example 4—Cell Cycle Arrest by Aphidicolin Mediated Increased Differentiation Efficiency To investigate the mechanism underlying the increased purity of stem cell-derived C-peptide positive cells induced by APH, cell proliferation, apoptosis and differentiation efficiency were examined during differentiation. The cell cycle progression was profiled at day 15, day 18, day 20 and day 27 of beta cell differentiation. In untreated cells, C-peptide positive cells started to form from day 15 (about 5%) (FIG. 2A) and reached a peak at day 20 (about 46%) (FIG. 2B). About 2% of total cells underwent proliferation during 2 hours of Edu incubation at each stage before day 20 and very few C-peptide positive cells were labeled positive for Edu (FIG. 2B). At day 27, the percentage of proliferating cells increased to about 13% and the percentage of C-peptide positive cells decreased due to proliferation of non-C-peptide cells in the clusters (FIG. 2B). When APH was added from day 15 to day 27, the number of C-peptide positive cells was increased as early as day 18, 3 days after addition of APH (FIG. 2C). At day 20, about 60% cells expressed C-peptide and the high expression of C-peptide was maintained until the day 27. Very few cells, if any, were proliferating through the whole duration of differentiation (FIG. 2C).

Figure 2D:
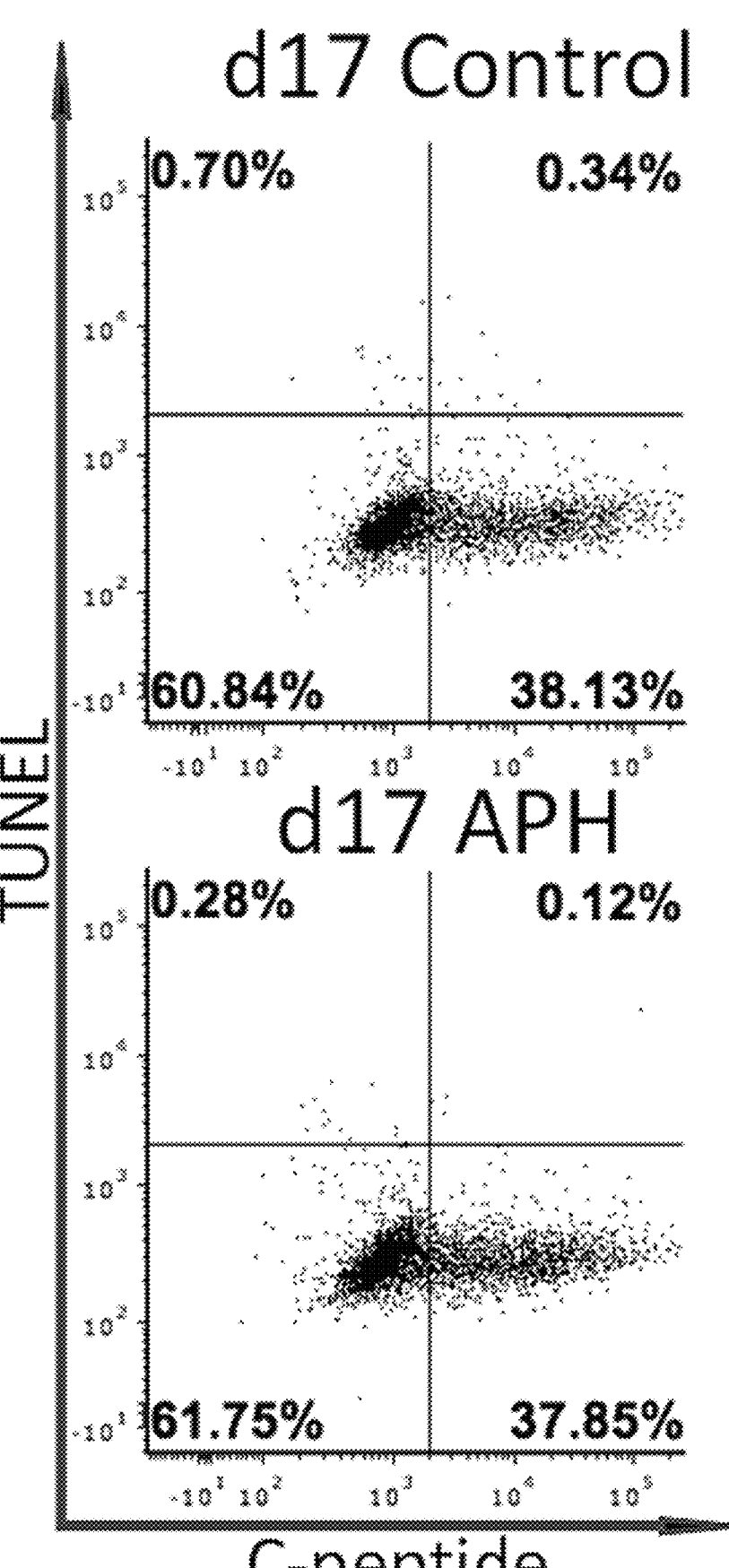
FIG. 2D are images of flow cytometry analysis with TUNEL staining of apoptotic C-peptide positive cells at day 17 where cells were treated with APH from about day 15-20 and controls.
Figure 2E:
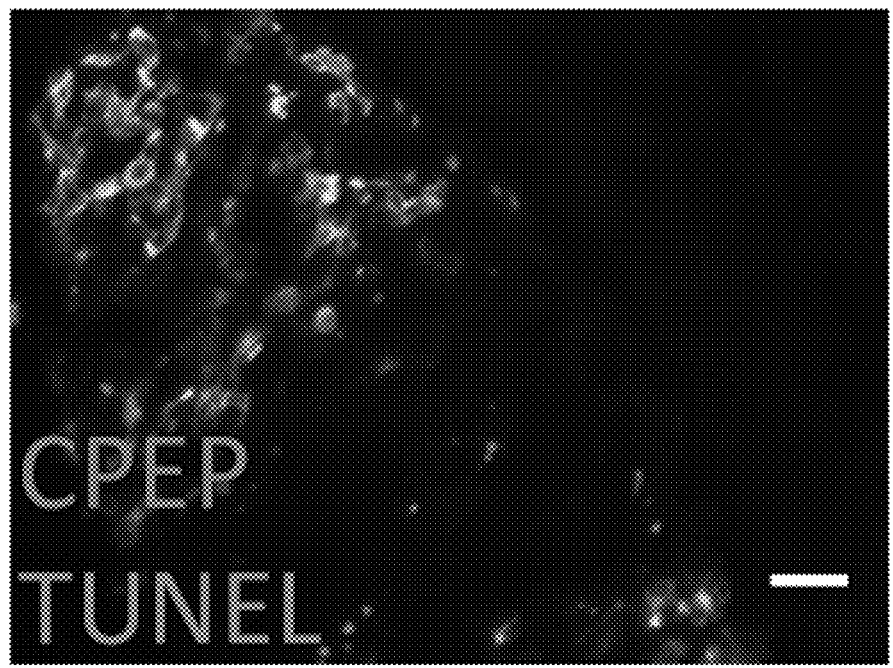
FIG. 2E are images of cells immunostained for TUNEL and C-peptide at day 27 where APH was added from about days 20-27 versus controls. Scale bar: 100 μm.
Figure 2E:
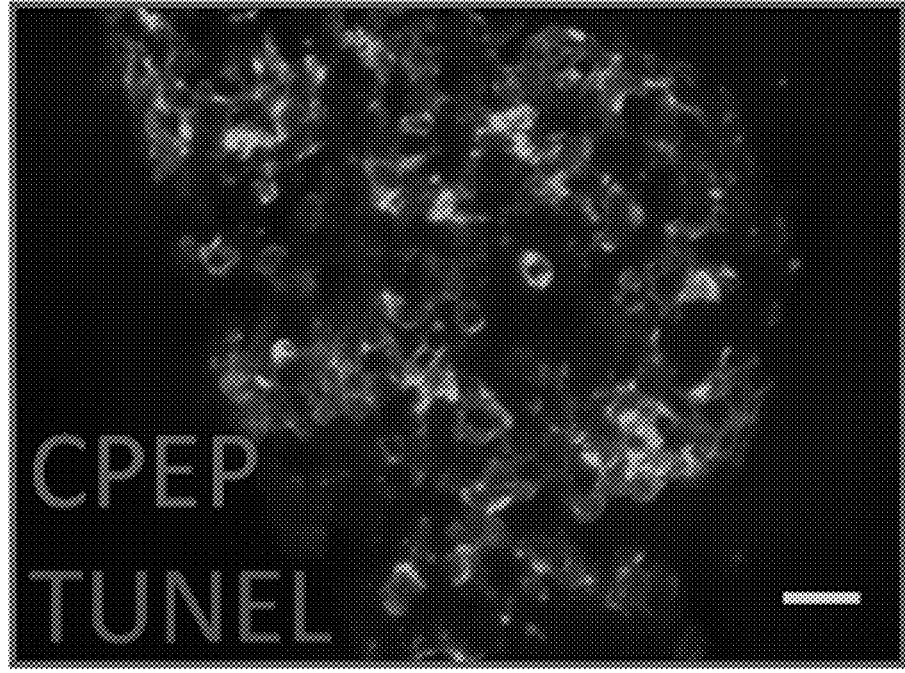
Figure 2G:
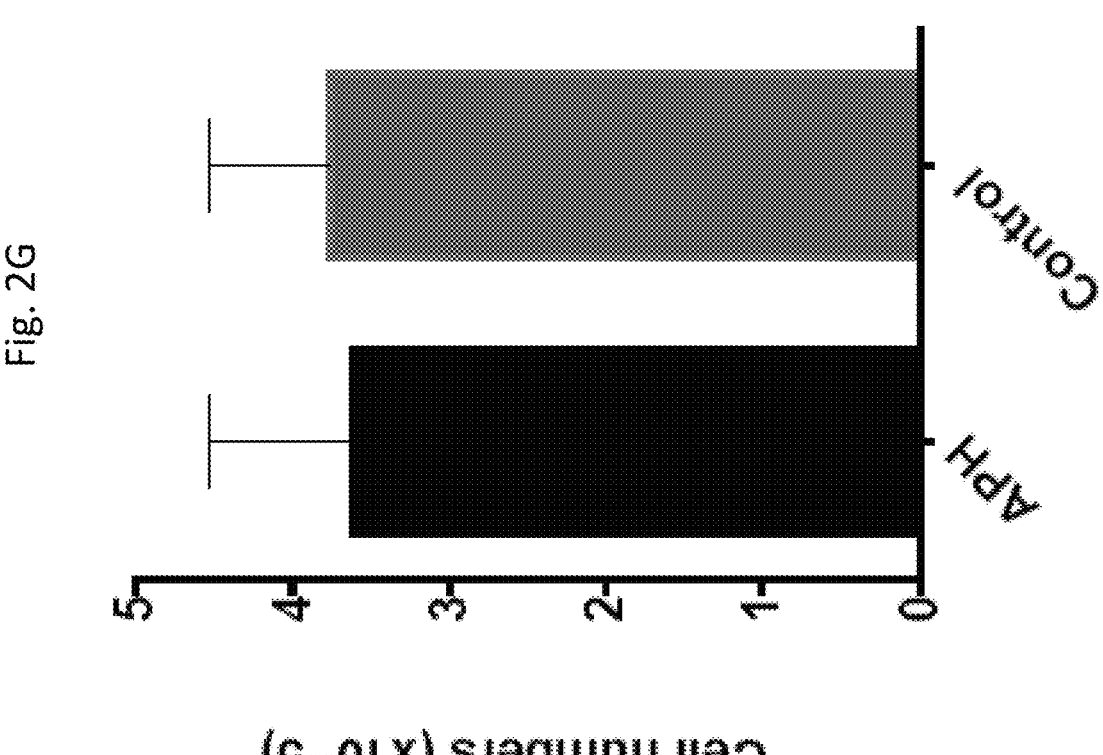
FIG. 2G shows a graph of the total number of cells at day 20 where APH was added from about days 15-20 versus controls.
Figure 2F:
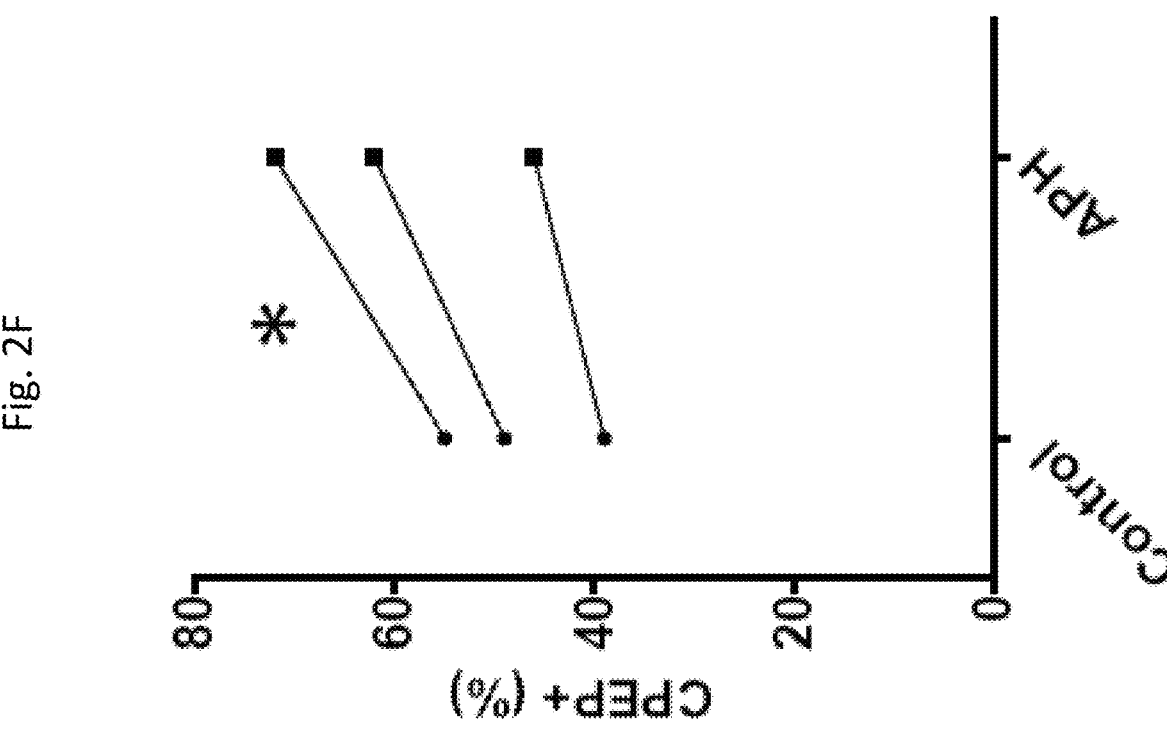
FIG. 2F is a graph of the percentage of C-peptide positive cells at day 20 with APH treatment versus control.

To determine whether the increased percentage of beta cells was due to cell death of proliferating progenitors or due to increased differentiation from pancreatic progenitor cells, absolute cell numbers and cell death were quantified. Cells at day 17 and day 27 with and without APH treatment were stained for TUNEL. No significant increase in cell apoptosis after APH treatment was found indicated by the percentage of TUNEL positive cells both at early (FIG. 2D) and late stage of APH treatment (FIG. 2E). The percentage of C-peptide positive cells was significantly increased at day 20 after APH treatment compared to that of control (FIG. 2F). The number of total cells at day 20 was comparable between APH and control group (FIG. 2G). Therefore, the increased percentage of C-peptide positive cells was due to the increased differentiation, not the elimination of non-C-peptide positive cells from day 15 to day 20. After day 20, APH maintained the purity of beta cell clusters by preventing the growth of non-beta cells.

Example 5—Aphidicolin Induced G1 Arrest by Upregulating Cell Cycle Inhibitors

To determine the cell cycle phase at which aphidicolin arrested pancreatic progenitors and beta cells, flow cytometry combined with Hoechst staining for DNA content and EdU labeling was performed.

Figures 3, 3A:
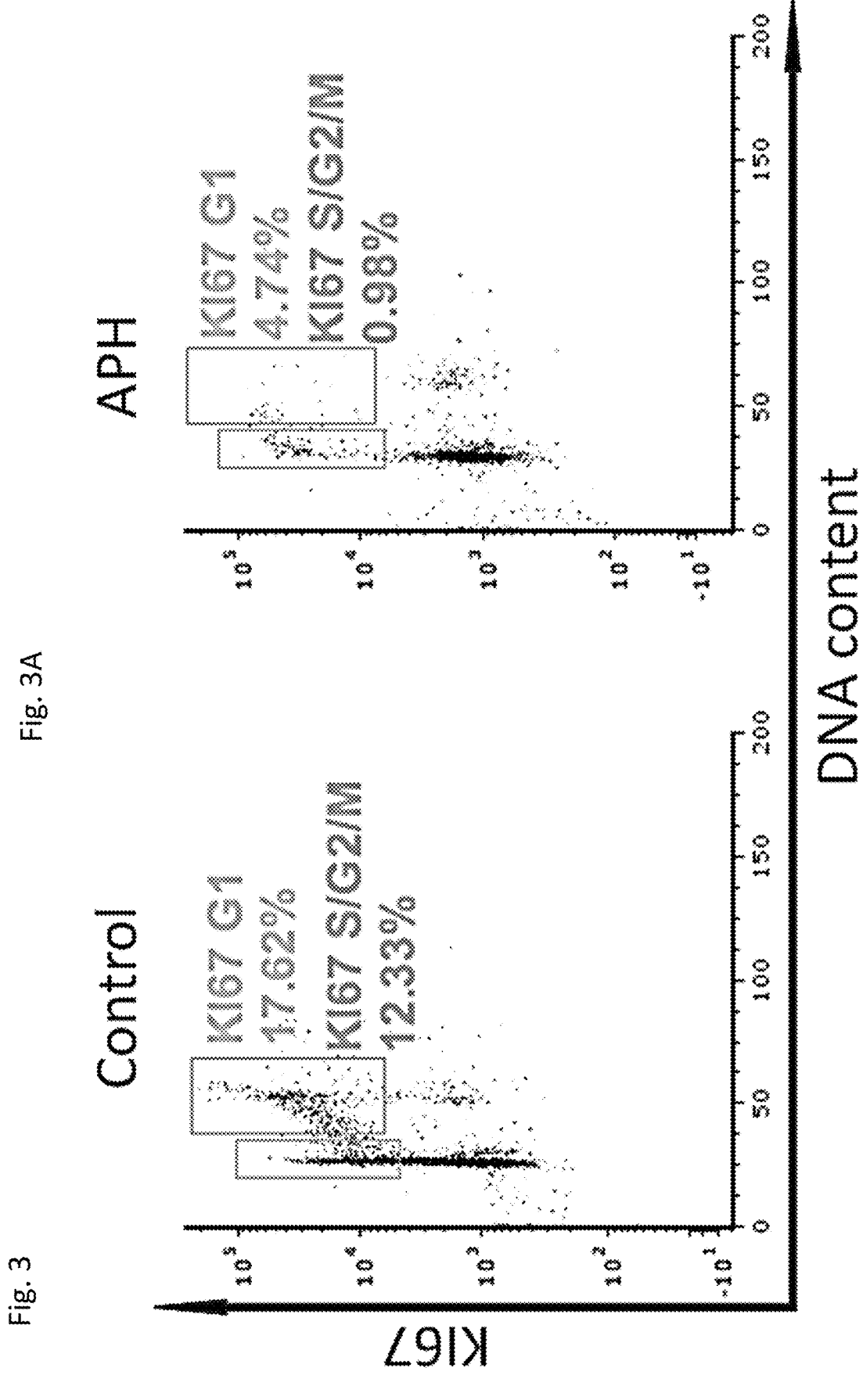
FIG. 3—Aphidicolin induced G1 arrest by upregulating cell cycle inhibitors.
FIG. 3A are images of flow cytometry analysis of cell cycle profile of untreated and APH-treated cells at day 27 indicated by flow cytometry combined with Hoechst staining for DNA content and KI67 labeling.
Figure 3B:
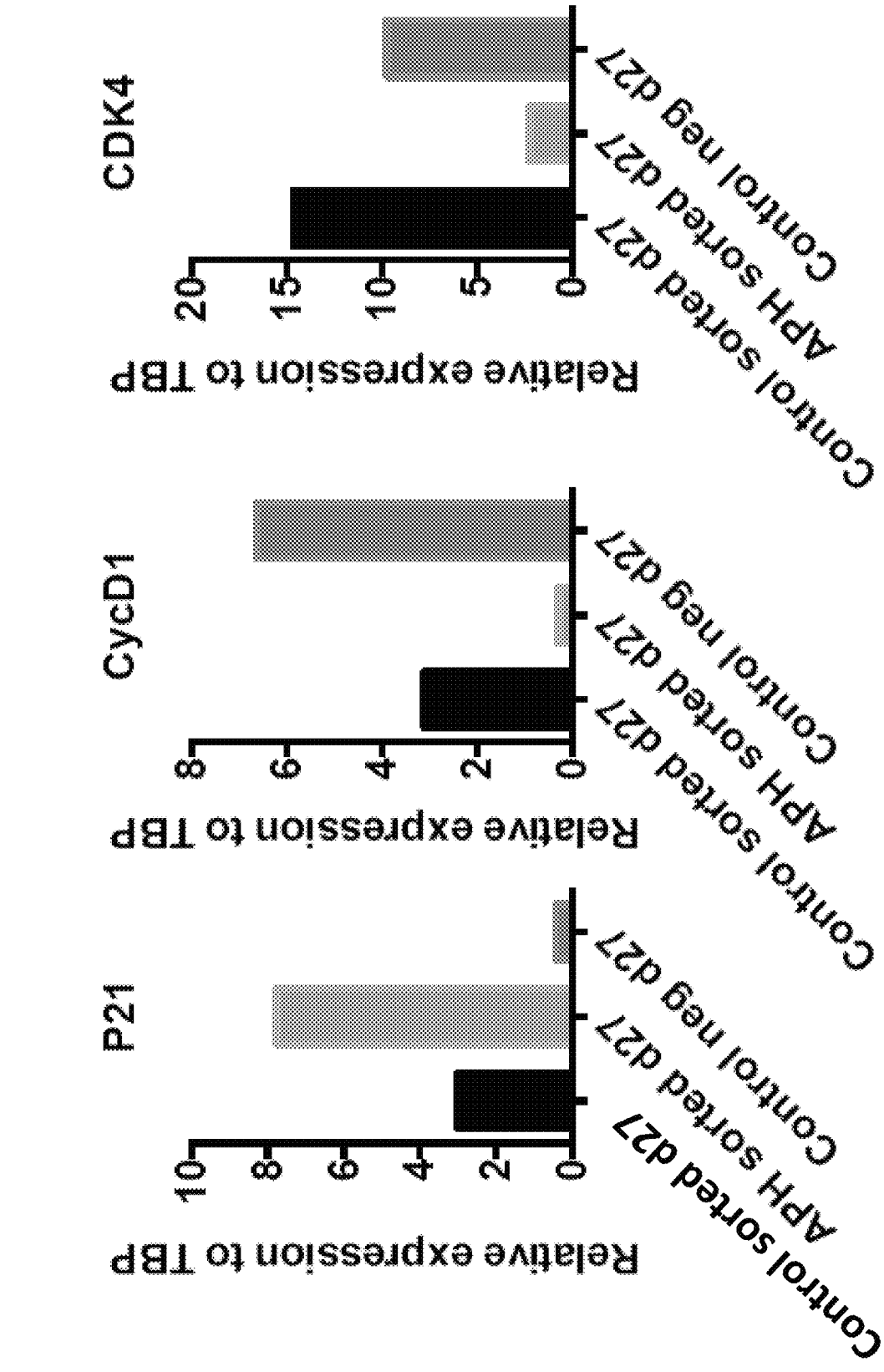
FIG. 3B show graphs of relative expression of cell cycle inhibitor (P21) and cell cycle activators (CycD1 and CDK4) in the GFP positive cells sorted from APH and control group and GFP negative cells sorted from control group.

By the end of day 27, 30% of control cells were in cell cycle through G1 to M phase indicated by the expression of KI67 (a proliferation marker expressed in the cells within cell cycle) and amount of DNA content (FIG. 3A). About 5% of APH-treated cells were in cell cycle and arrested in G1 phase (FIG. 3A). The cell cycle gene expression in insulin expressing cells was also examined. The expression of P21, a cell cycle progression inhibitor, was upregulated and the expressions of Cyclin D1 and CDK4, both involved in G1-phase progression, were downregulated in APH treated insulin positive cells (FIG. 3B). These results demonstrated that APH promotes the differentiation of pancreatic progenitors to endocrine cells by G1 arrest.

Example 6—Additional Agents Arrested the Cell Cycle and Increased Differentiation Efficiency To determine whether other compounds able to induce G1 arrest similarly promoted differentiation to beta cells, pancreatic progenitors were exposed to a panel of compounds with anti-proliferative properties: Pyridostatin (PDS) stabilizes G-quadruplexes and arrests cell cycle (Moruno-Manchon et al., 2017; Zimmer et al., 2016); Cisplatin (Cis) induces DNA damage via DNA cross link and low dose arrests cells at S phase (Qin and Ng, 2002; Wagner and Karnitz, 2009); E2F inhibitor (E2Fi) inhibits the master transcription factors involved in S phase entry (Ma et al., 2008; Pardee et al., 2004; Rouaud et al., 2018); Etoposide (Eto) is a topoisomerase inhibitor and stops the unwind of the DNA helix during replication (Cliby et al., 2002; Korwek et al., 2012; Nam et al., 2010; Smith et al., 1994); CDK4 inhibitor (Cdk4i) arrests cells at early G1 phase (Huang et al., 2012); Ciprofloxacin (Cipro) inhibits MCM2-7 replicative helicase at replication origin (Simon et al., 2013); A485 inhibits p300, a histone acetylase, and arrests the cell cycle and inhibits p300 dependent transcription (Lasko et al., 2017). RL5a arrests the cell cycle by inhibiting replication origin licensing (Gardner et al., 2017).

Figures 4, 4A:
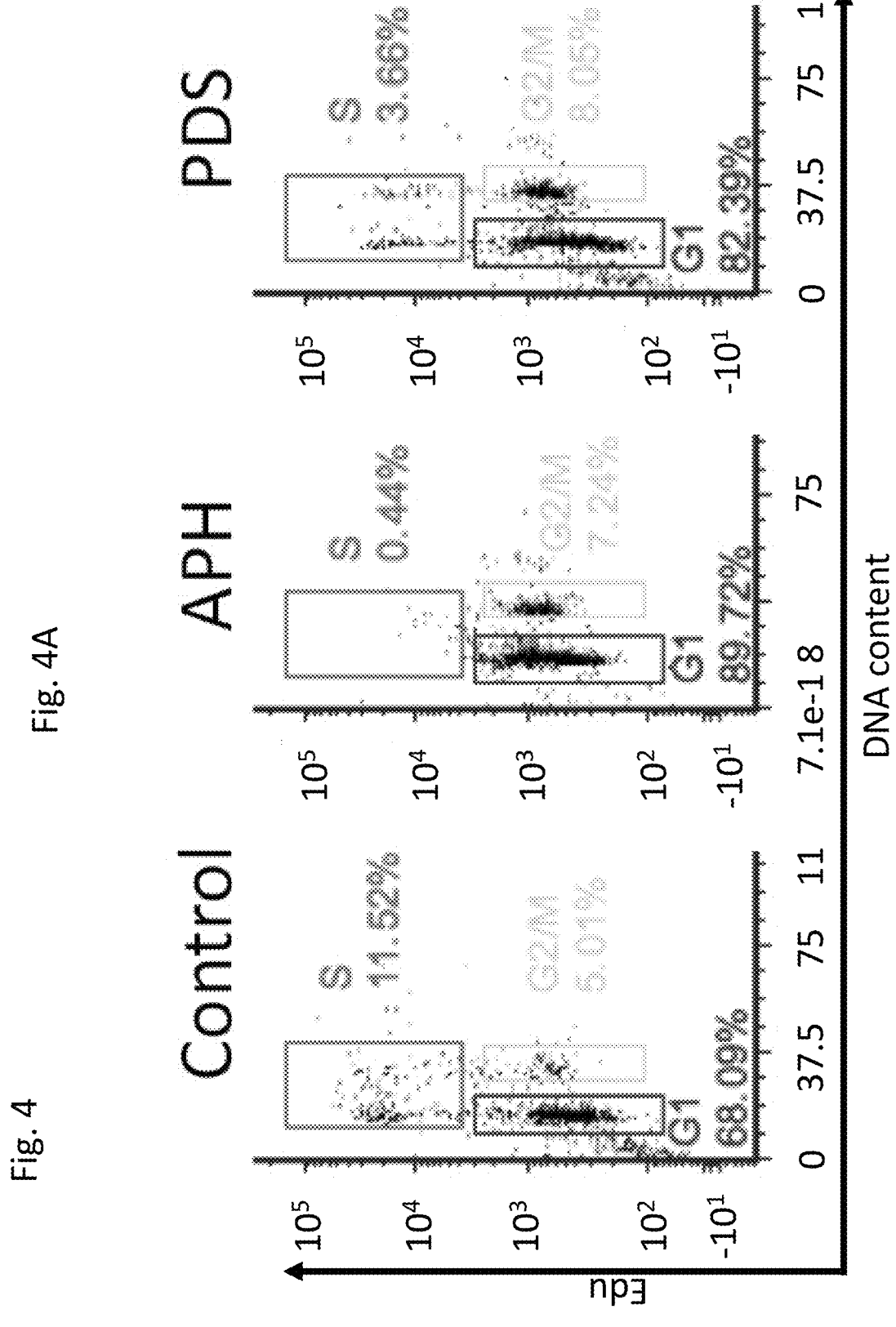
FIG. 4—Inhibition of DNA replication arrested the cell cycle and increased differentiation efficiency.
FIG. 4A shows the cell cycle profile of cells treated with indicated compounds.
Figure 4A:
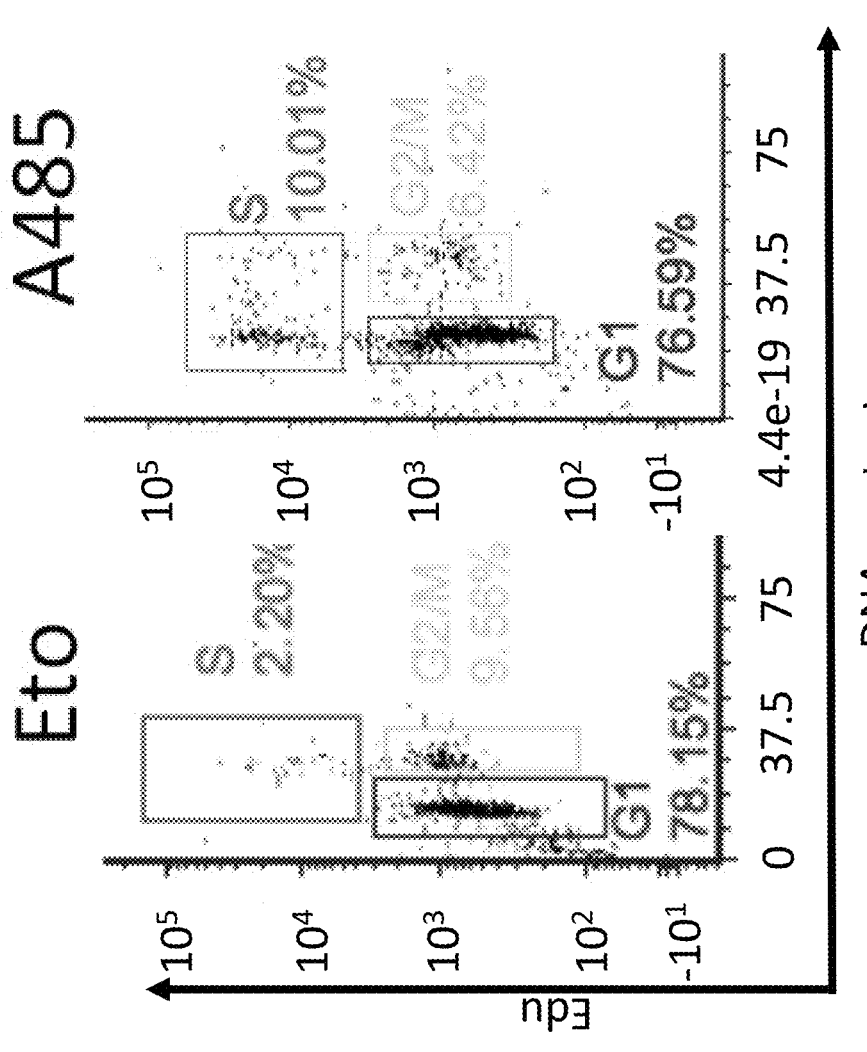
Figures 4, 4A:
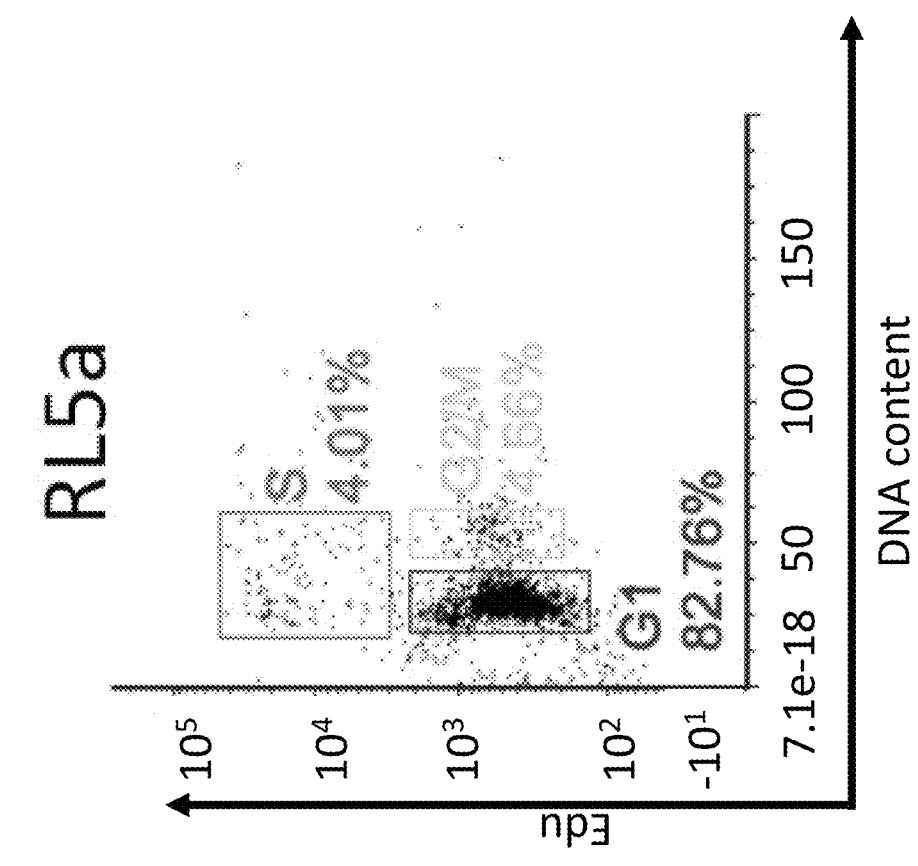
Figure 4B:
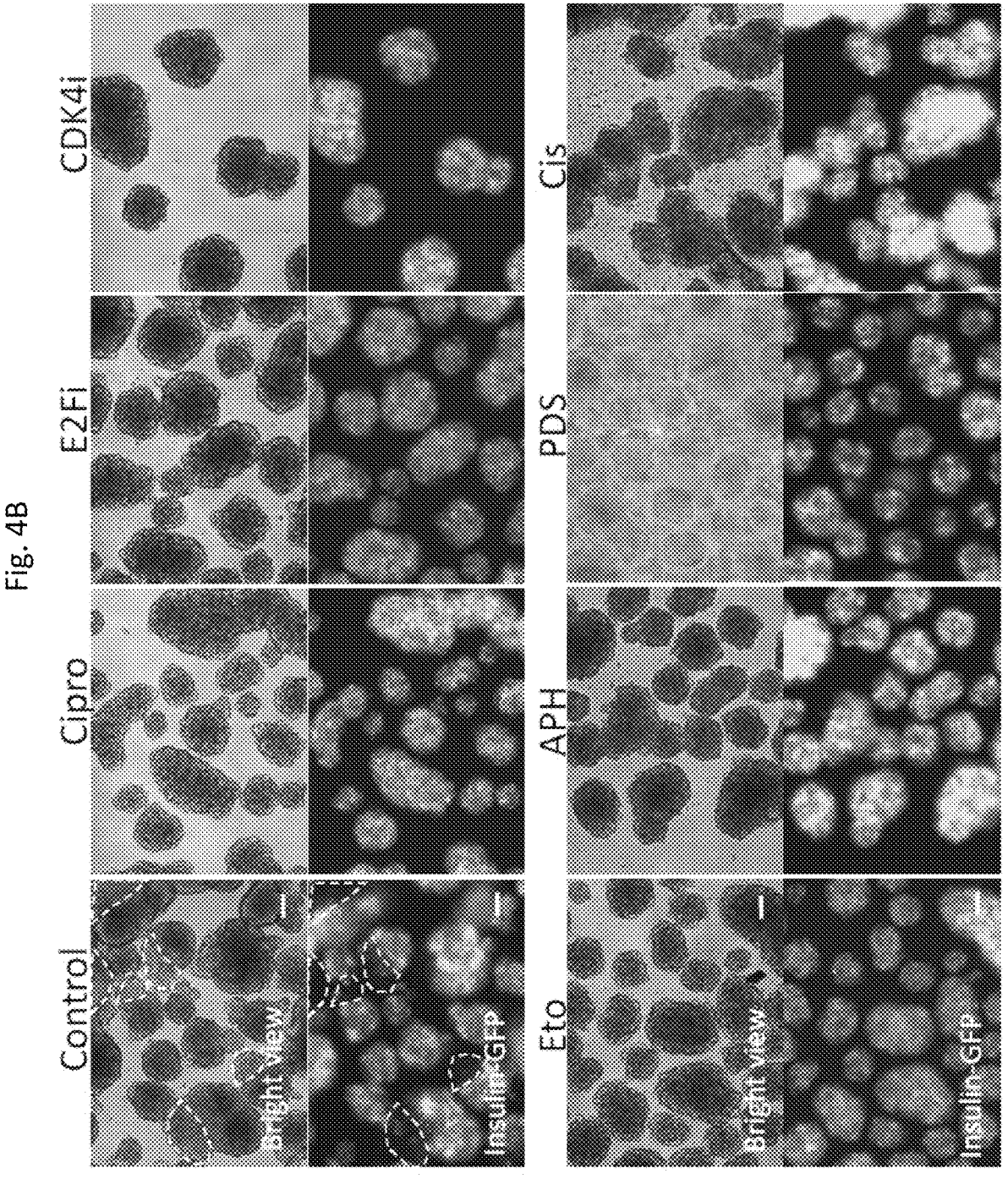
FIG. 4B are representative bright view and fluoresce microscopic images of clusters treated with indicated compounds. Scale bar: 100 μm.
Figure 4C:
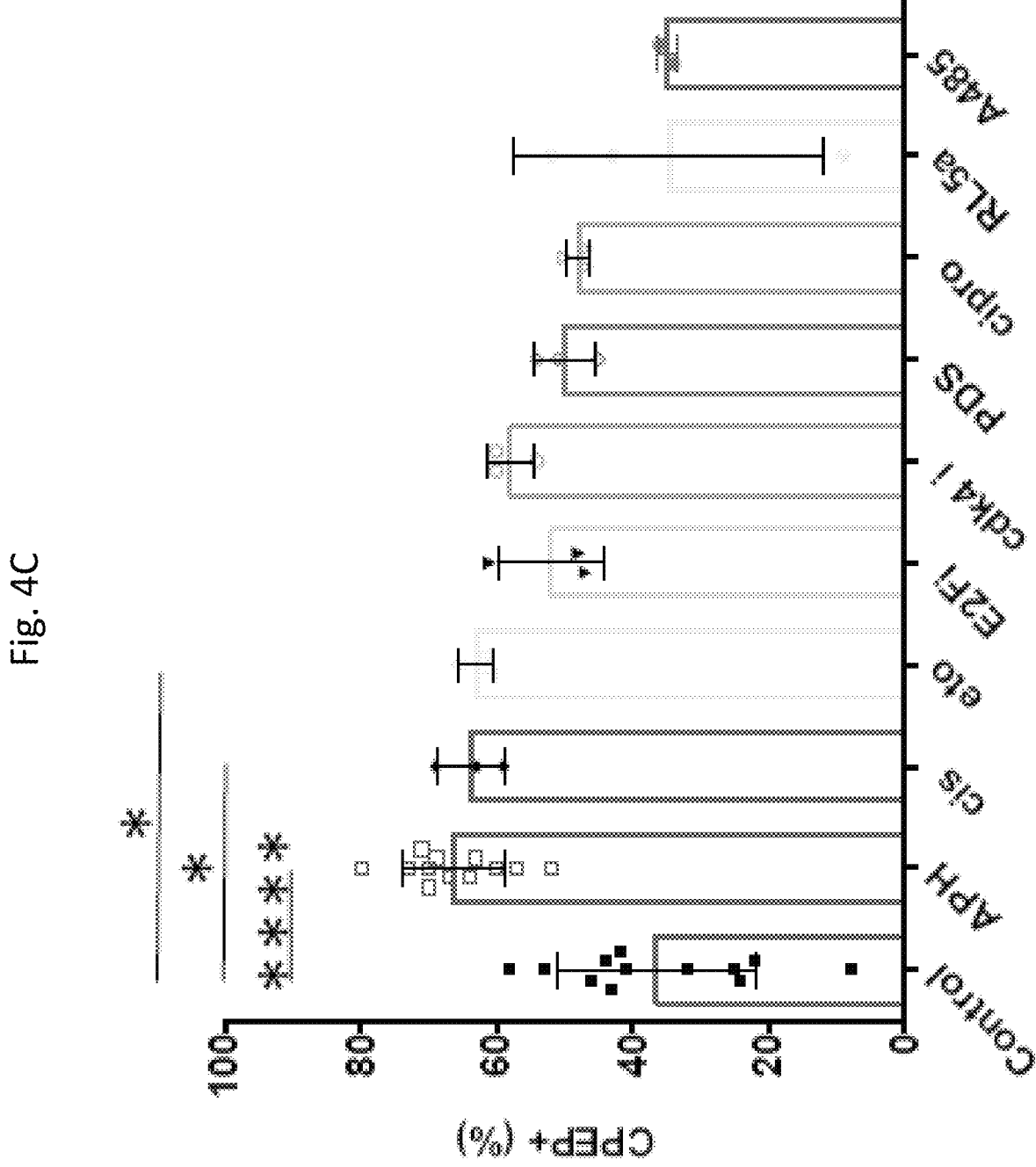
FIG. 4C shows a graph of the quantification of derived C-peptide positive cells using indicated compounds.

All of the tested inhibitors ceased the cell cycle progression by arresting cells at G1 phase (FIG. 4A). The majority of tested DNA replication inhibitors increased the percentage of C-peptide positive cells at the end of differentiation on day 27 (FIG. 4B). However, the increase was not equal for all. Etoposide, cisplatin and aphidicolin were the most effective compounds to induce differentiation of pancreatic progenitors to C-peptide positive cells (FIG. 4C). RL5a failed to increase the number of C-peptide positive compared to control and P300 inhibitor also showed no significant increase, possibly because the inhibition of transcriptional activity impairs insulin expression. Therefore, compounds that inhibit cell cycle progression in late G1, and inhibit entry into S-phase were the most effective in promoting beta cell differentiation, while compounds that affect early G1-phase (CDK4, RL5a) were less effective.

Example 7—G1 Arrest Stabilized Beta Cell Identity

Figures 5, 5A:
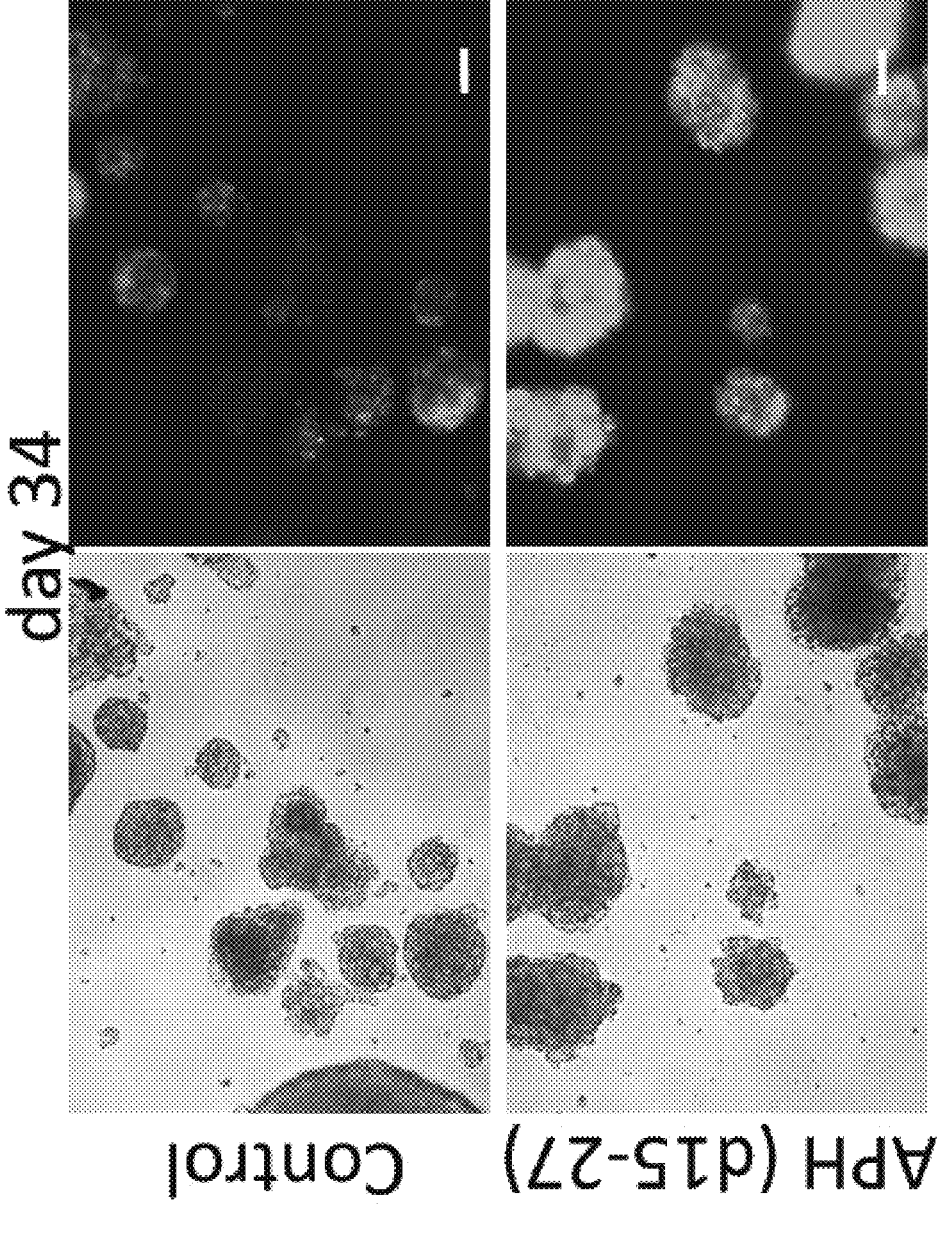
FIG. 5—Inhibition of DNA replication stabilized beta cell identity.
FIG. 5A shows representative microscopic images of cells at day 34 after releasing cells from APH from day 27 to day 34. Scale bar: 100 μm.

With APH, a high proportion of cells in the islet-like clusters were positive for C-peptide and NKX6.1, a transcription factor for maintaining the beta cell identity and functional maturation (Schaffer et al., 2013). It was further investigated if APH had an effect on the preservation of beta cell identity after long-term culture. Aphidicolin was removed on day 27 to determine if the treatment had an effect on the stability of beta cells, and whether beta cell identity would be stable in the absence of the compound. Beta cells were cultured for additional 7 days until about day 34 and 30 days until about day 60 upon removal of these compounds at day 27. In untreated control cells, the insulin-GFP expression was gradually decreased (FIG. 5A). In contrast, in APH treated cells, there was no decrease in C-peptide or NKX6.1 on day 34 (FIG. 5A). After 7 days of releasing cells from APH, the percentage of C-peptide positive cells, and C-peptide and NKX6.1 double positive cells was comparable to that of day 27 before releasing, whereas the percentage of C-peptide positive cells was significantly reduced in control group from day 27 to day 34

Figure 5B:
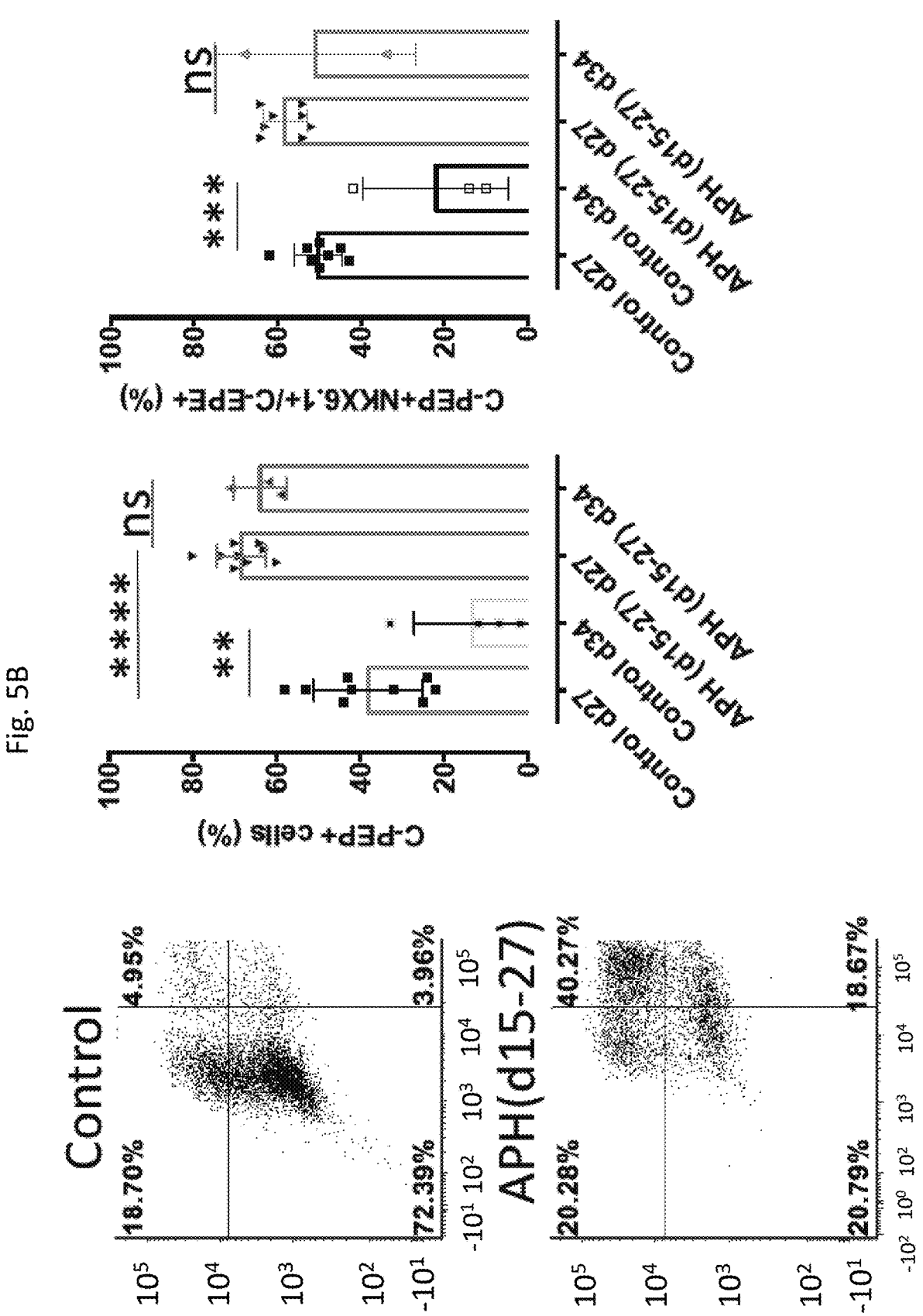
FIG. 5B shows the percentage of C-peptide and NKX6.1 positive cells at day 34 with and without APH treated from about days 15-27 determined by flow cytometry. Both representative flow cytometry analysis and graphs quantifying the analysis are shown.
Figure 5C:
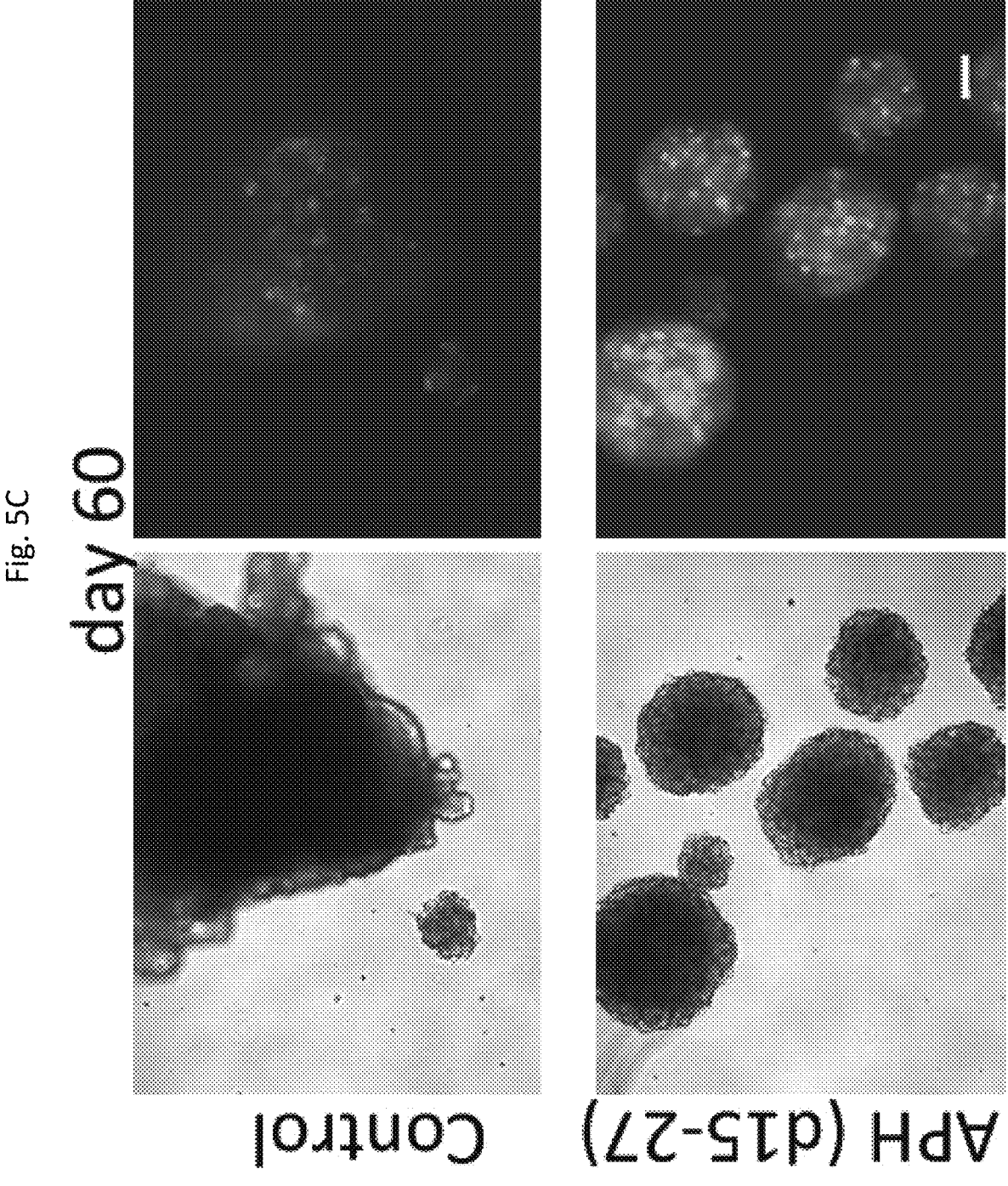
FIG. 5C are representative images of the GFP expression in clusters cultured until day 60 with and without APH treatment from about days 15-27. Scale bar: 100 μm.
Figure 5D:
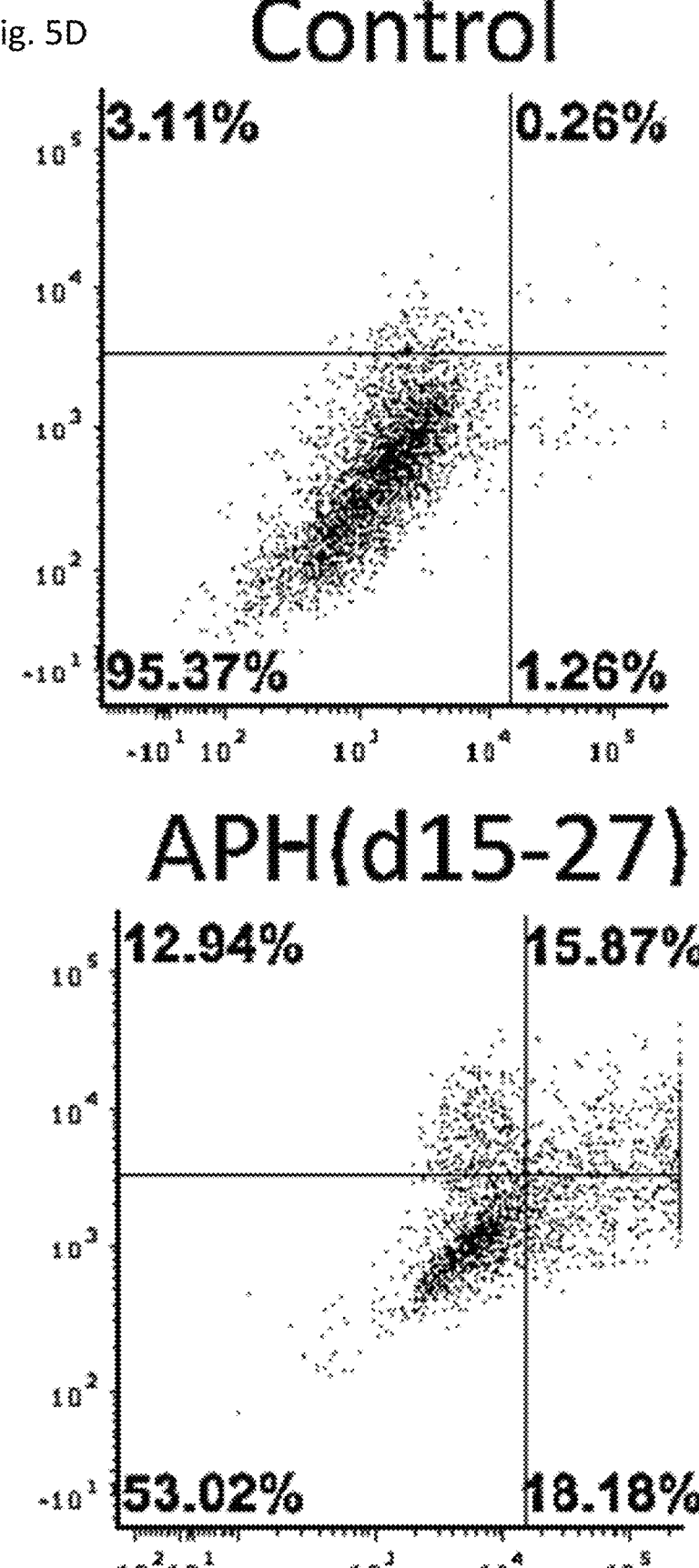
FIG. 5D shows the percentage of C-peptide and NKX6.1 positive cells at day 60 cultured until day 60 with and without APH treatment from about days 15-27, determined by flow cytometry.

(FIG. 5B). After further culturing of the cells for extra 30 days, very few of cells in control group remained GFP expression and were positive for C-peptide. The number of GFP and C-peptide positive cells in APH treated condition was also decreased at day 60 compared to day 27 before removal of APH, but the percentage compared to control remained high, at about 34% versus about 2% in controls (FIG. 5C, FIG. 5D). This indicates that transient APH treatment was able to stabilize the beta cell identity in the in vitro culture condition even after release from the compound.

Figure 5E:
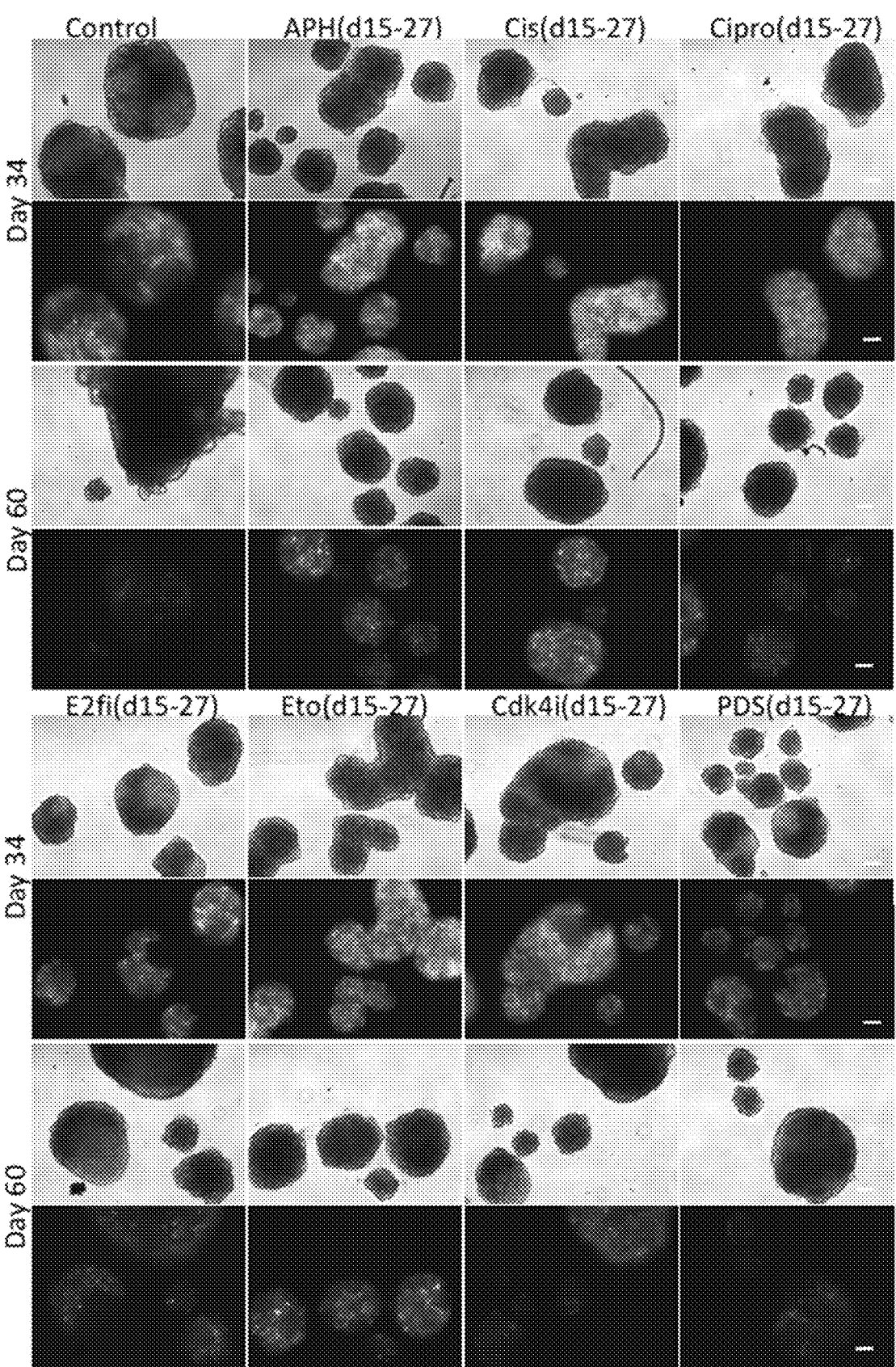
FIG. 5E are representative images showing insulin expression in beta cell cultures indicated by GFP at day 34 and day 60 when cells were treated with indicated compounds at indicated time point. Scale bar: 100 µm.
Figure 5F:
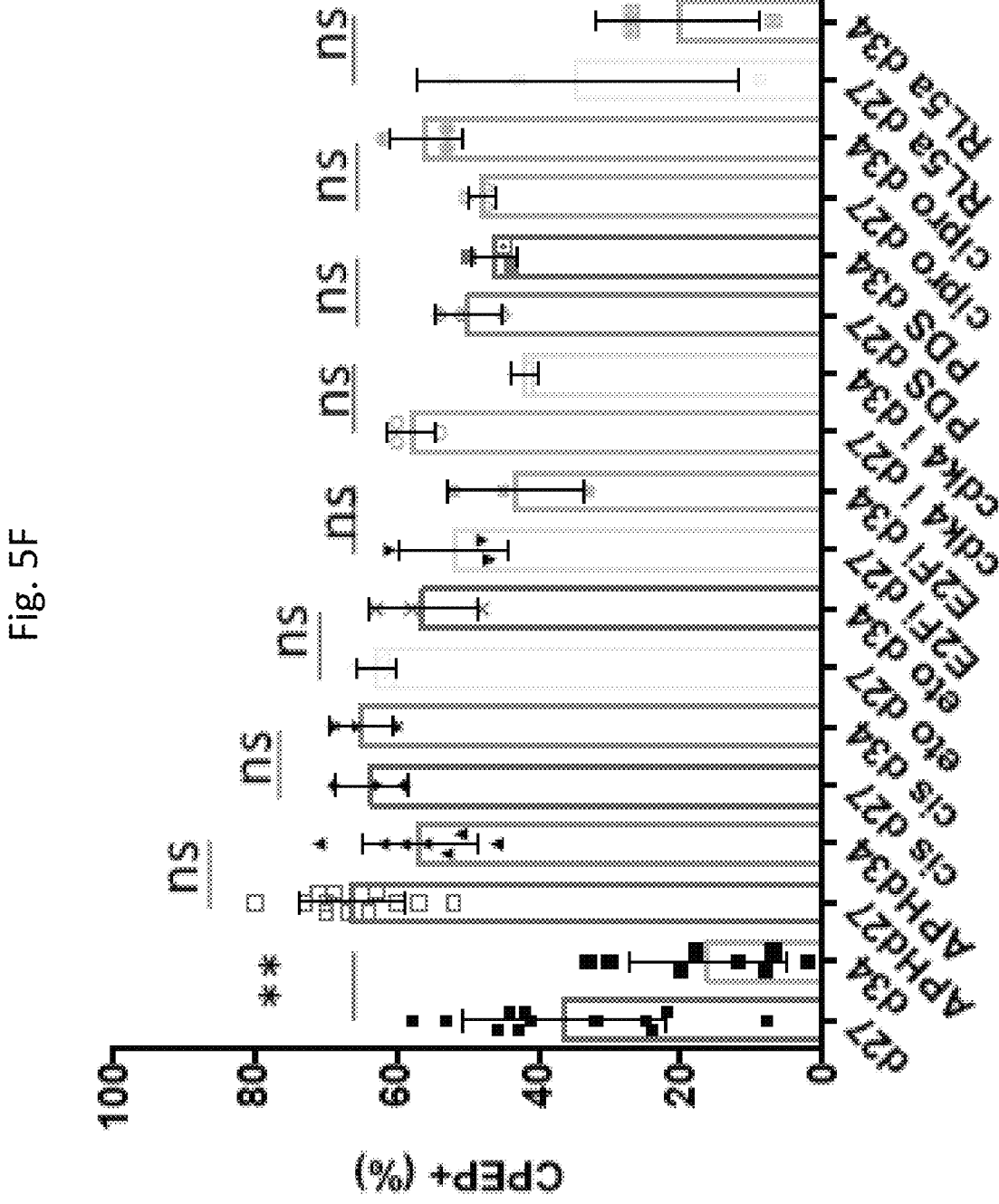
FIG. 5F are graphs showing the quantification of C-peptide positive cells in beta cell clusters at day 27 and day 34 for each indicated compound.

The ability of other DNA replication inhibitors to stabilize the beta cell identity was investigated. The expressions of GFP were maintained after releasing cells from these inhibitors for 7 days until day 34. With additional 30 days of culture, the expressions of GFP were reduced in all conditions at certain levels, but the cells treated with Cis and Eto expressed higher GFP than the cells treated with APH compared to the other conditions (FIG. 5E, FIG. 5F).

Example 8—Inhibition of DNA Replication Improved the Maturity of Stem Cell Derived Beta Cells In Vitro APH increased the differentiation efficiency of stem cell derived beta cells. The next question was if the maturity and function of stem cell derived beta cells were improved after APH treatment.

Figures 6, 6A:
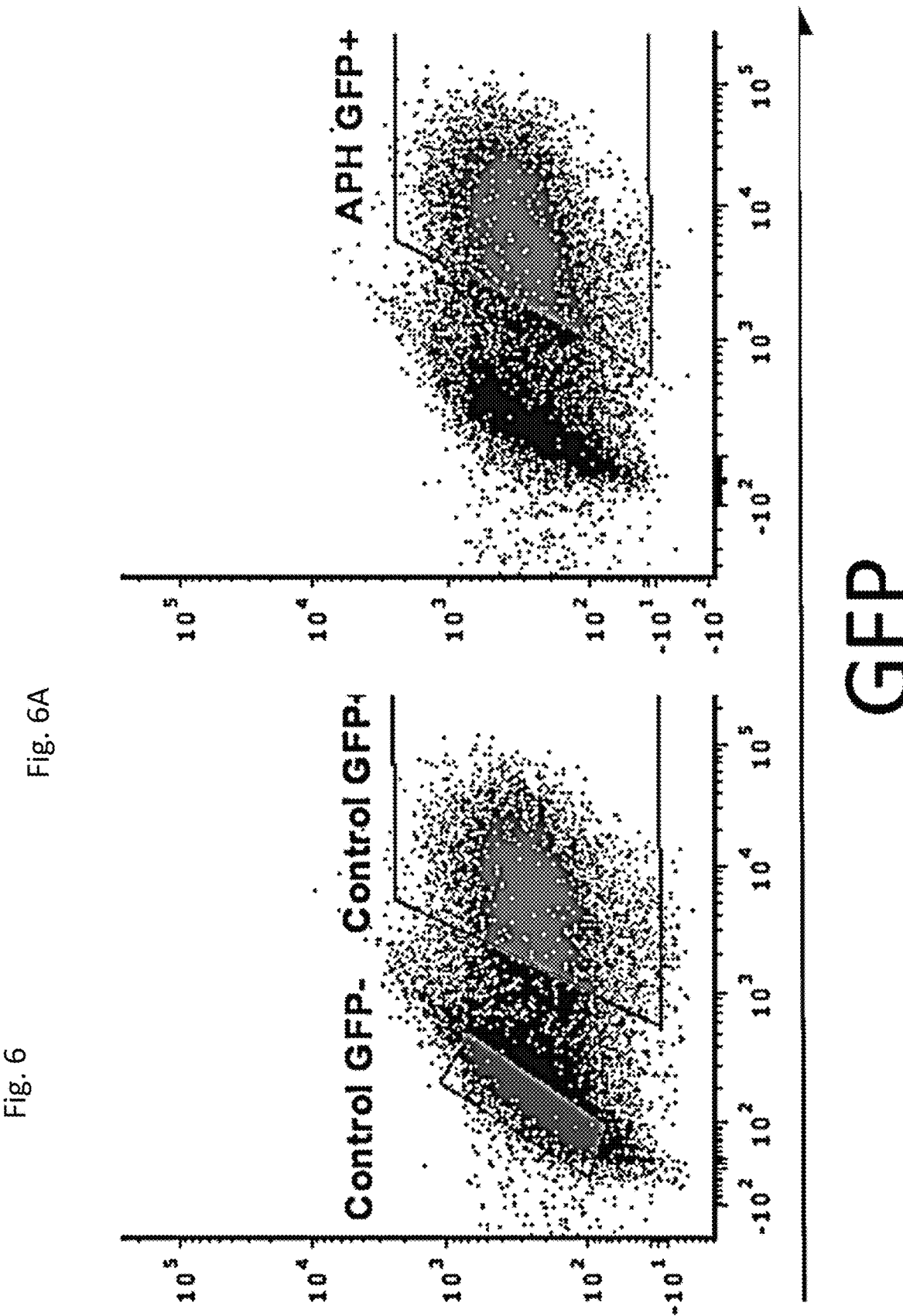
FIG. 6—Inhibition of DNA replication improved the maturation of stem cell derived beta cells.
FIG. 6A shows the insulin-GFP positive and negative cells sorted from control and APH treated group for downstream analysis.
Figure 6B:
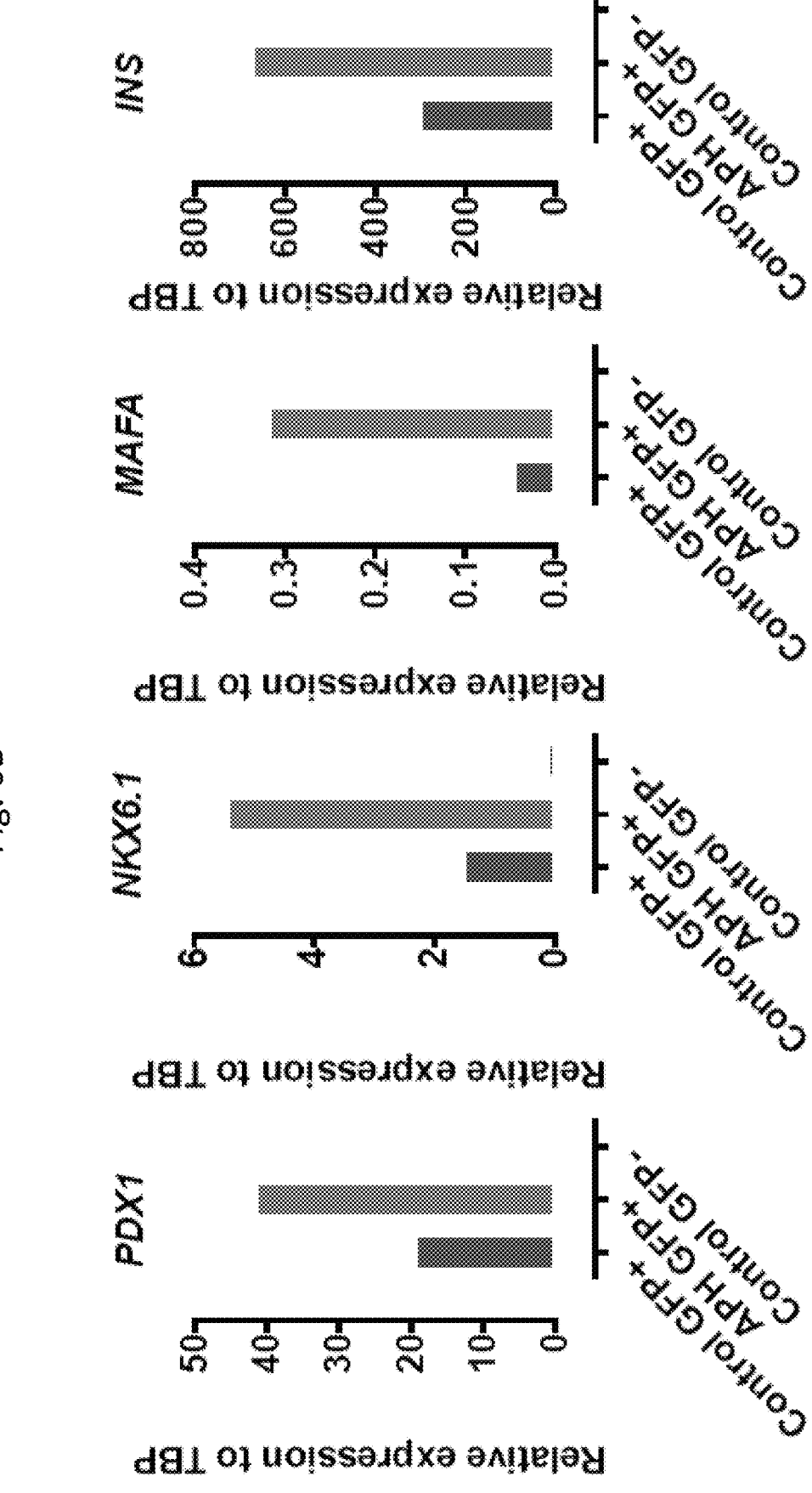
FIG. 6B show graphs quantifying the gene expression of the indicated genes in the indicated sorted cells by RT-PCR.
Figure 6D:
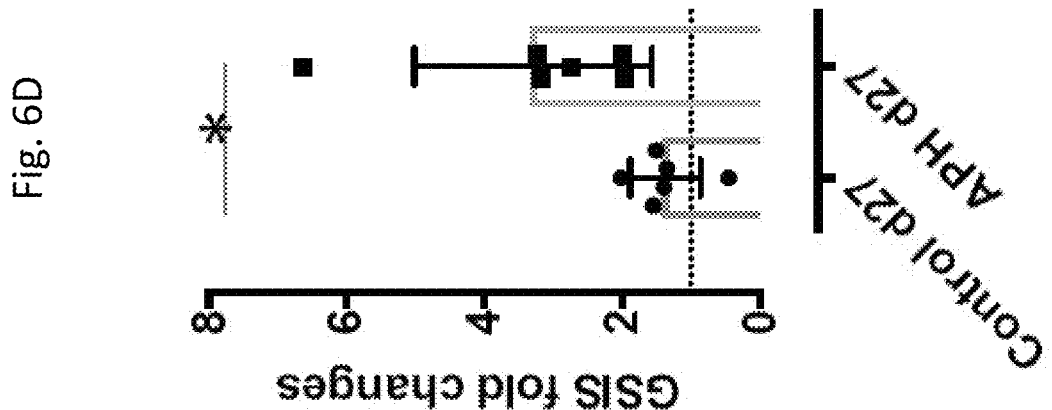
FIG. 6D is a graph of the glucose stimulation index determined by the fold changes of C-peptide secretions when control cells and APH treated cells incubated in the 2 mM and 20 mM glucose.
Figure 6C:
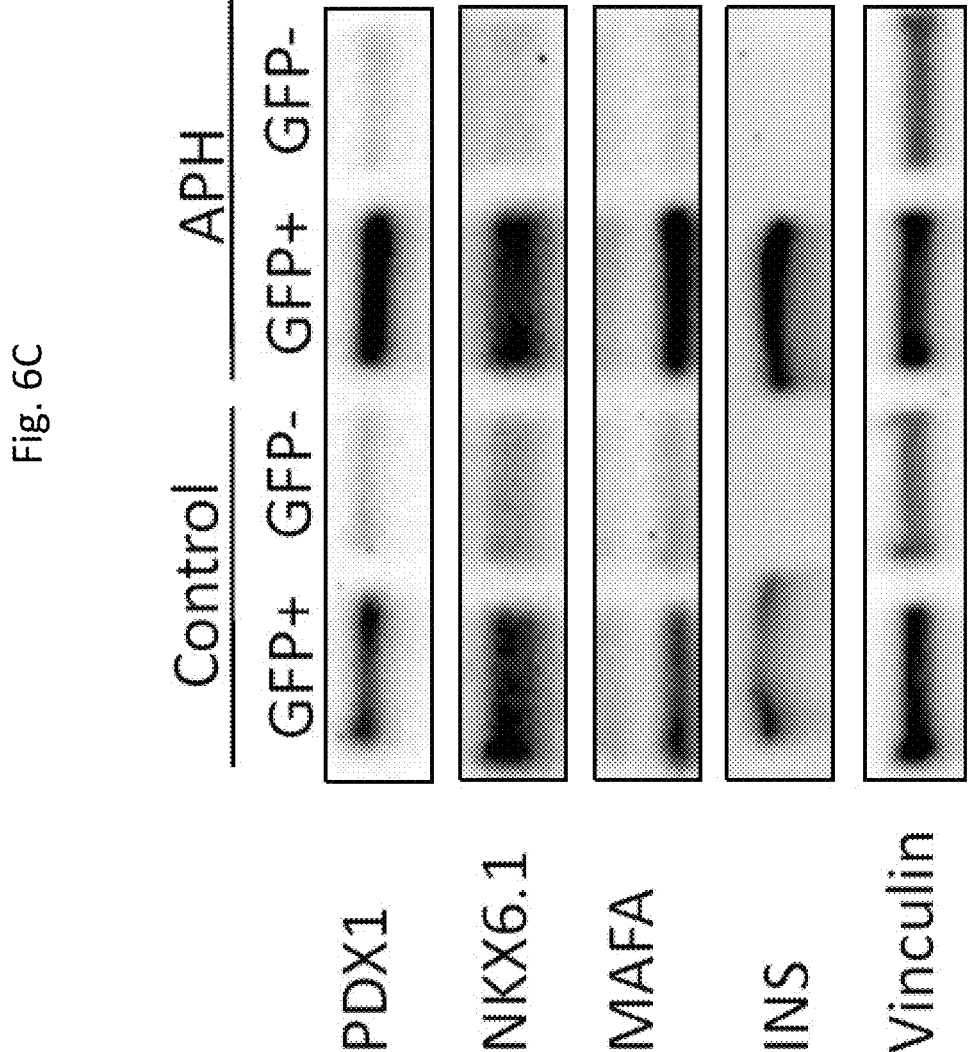
FIG. 6C shows a representative western blot of the protein expression of indicated proteins in the indicated sorted cells.

Insulin positive cells were isolated based on GFP expression and the expressions of genes related to the maturation of beta cells including PDX1, NKX6.1, MAFA and insulin were evaluated (FIG. 6A). The expressions of PDX1, NKX6.1, MAFA and insulin were significantly upregulated in GFP positive cells isolated from APH treated clusters at transcription level compared to GFP positive cells in control clusters and no expression of beta cell markers was detected in GFP negative cells (FIG. 6B). The increased expression of PDX1, NKX6.1, MAFA and insulin was further confirmed at the translational level by Western Blot (FIG. 6C). In addition, the C-peptide secretion was increased 2-6-fold, with an average of 3-fold, in response to high levels of glucose (FIG. 6D).

Figure 7D:
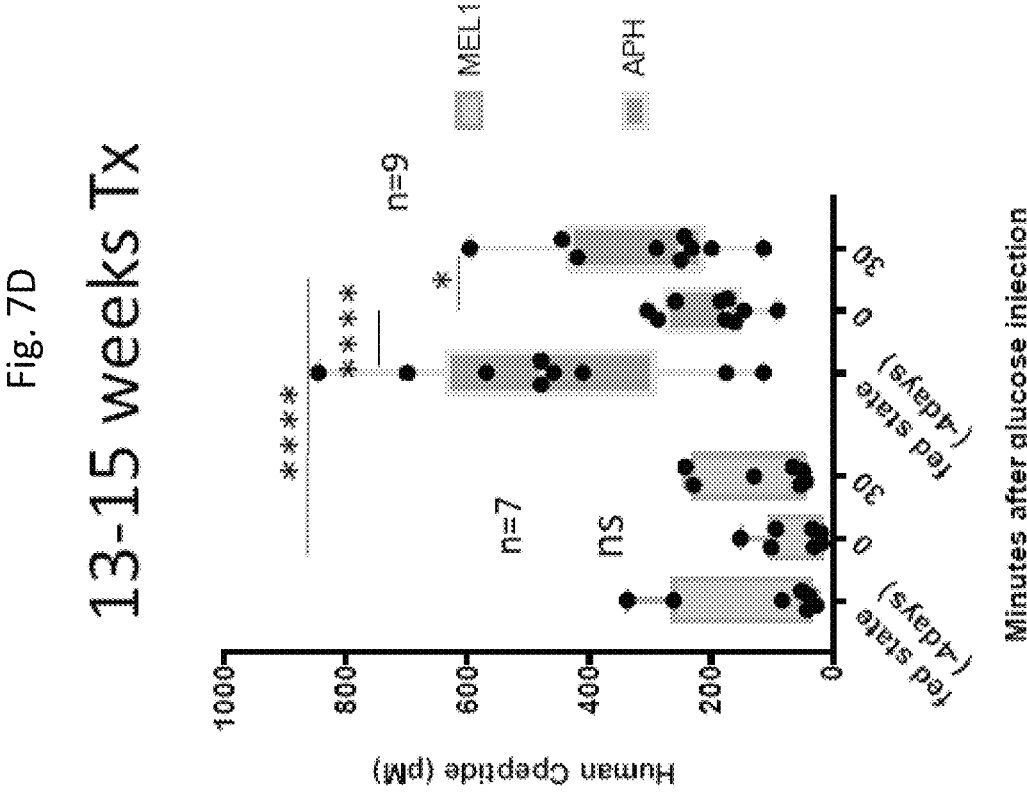
FIG. 7D shows a graph of human C-peptide serum concentration in mice at 13-15 weeks after transplantation with cells treated with APH (APH) and control cells (MEL1) at fed state, fasting and 30 minutes after glucose injection.
Figure 7C:
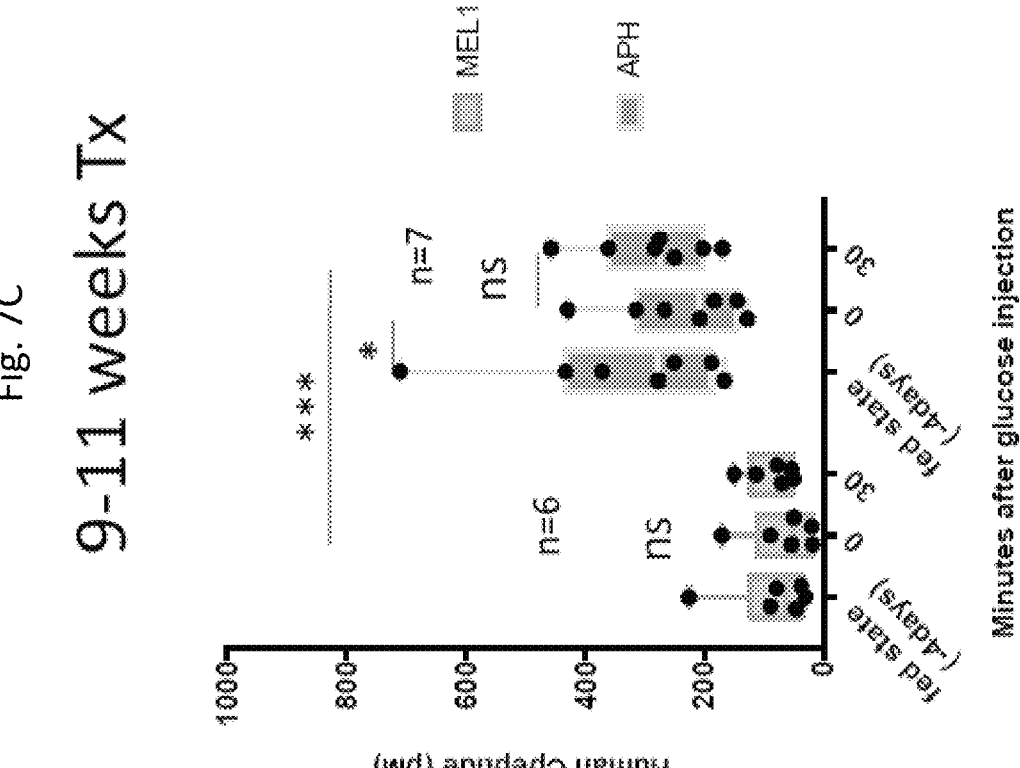
FIG. 7C shows a graph of human C-peptide serum concentration in mice at 9-11 weeks after transplantation with cells treated with APH (APH) and control cells (MEL1) at fed state, fasting and 30 minutes after glucose injection.

Example 9—APH Treated Stem Cell Derived Beta Cells Protected Mice from Diabetes To test the ability of aphidicolin treated islet-like clusters to regulate blood glucose levels, treated and untreated cells were grafted into NSG mice on day 27 of differentiation. After transplantation in the immunodeficient mice, the mice transplanted with APH treated cells developed higher human C-peptide starting from 2 weeks after engraftment compared to that of control mice (FIG. 7A). The increase became significant from 6 weeks after transplantation (FIG. 7B). In addition, the secretion of human C-peptide in mice was downregulated when mice were fasted (FIG. 7B, FIG. 7C, FIG. 7D) and increased after glucose injection (FIG. 7D), indicating the engrafted beta cells were able to respond to changes in blood glucose levels.

Figures 7E, 7F:
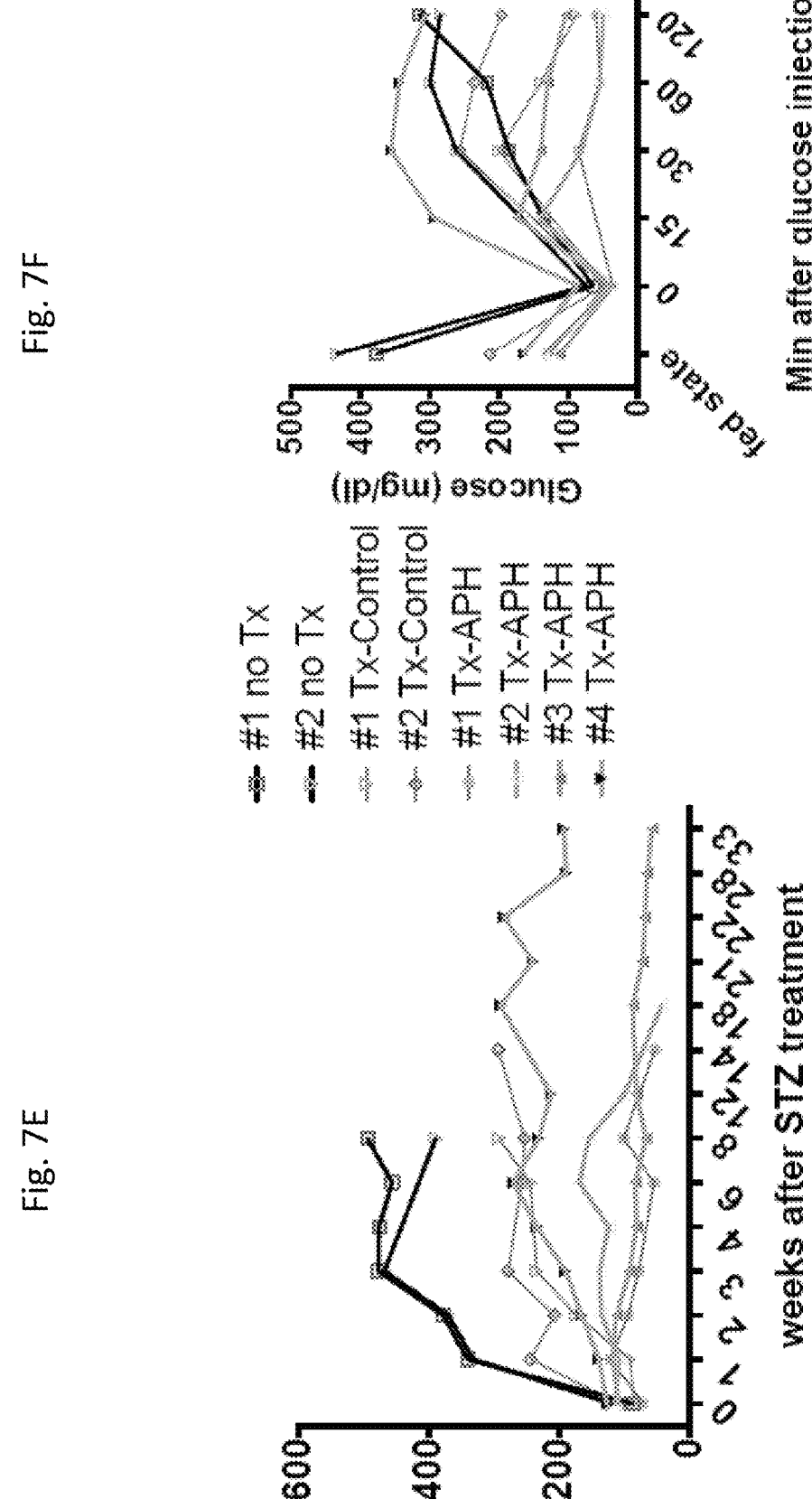
FIG. 7E shows a graph of blood glucose levels of STZ-treated mice without transplantation (no Tx) (n=2), transplanted with control cells (Tx-Control) (n=2) and with APH treated cells (Tx-APH) (n=4).
FIG. 7F shows a graph of glucose tolerance test of STZ-treated mice in fed state, fasting state and 15-120 min after glucose injection.
Figure 7G:
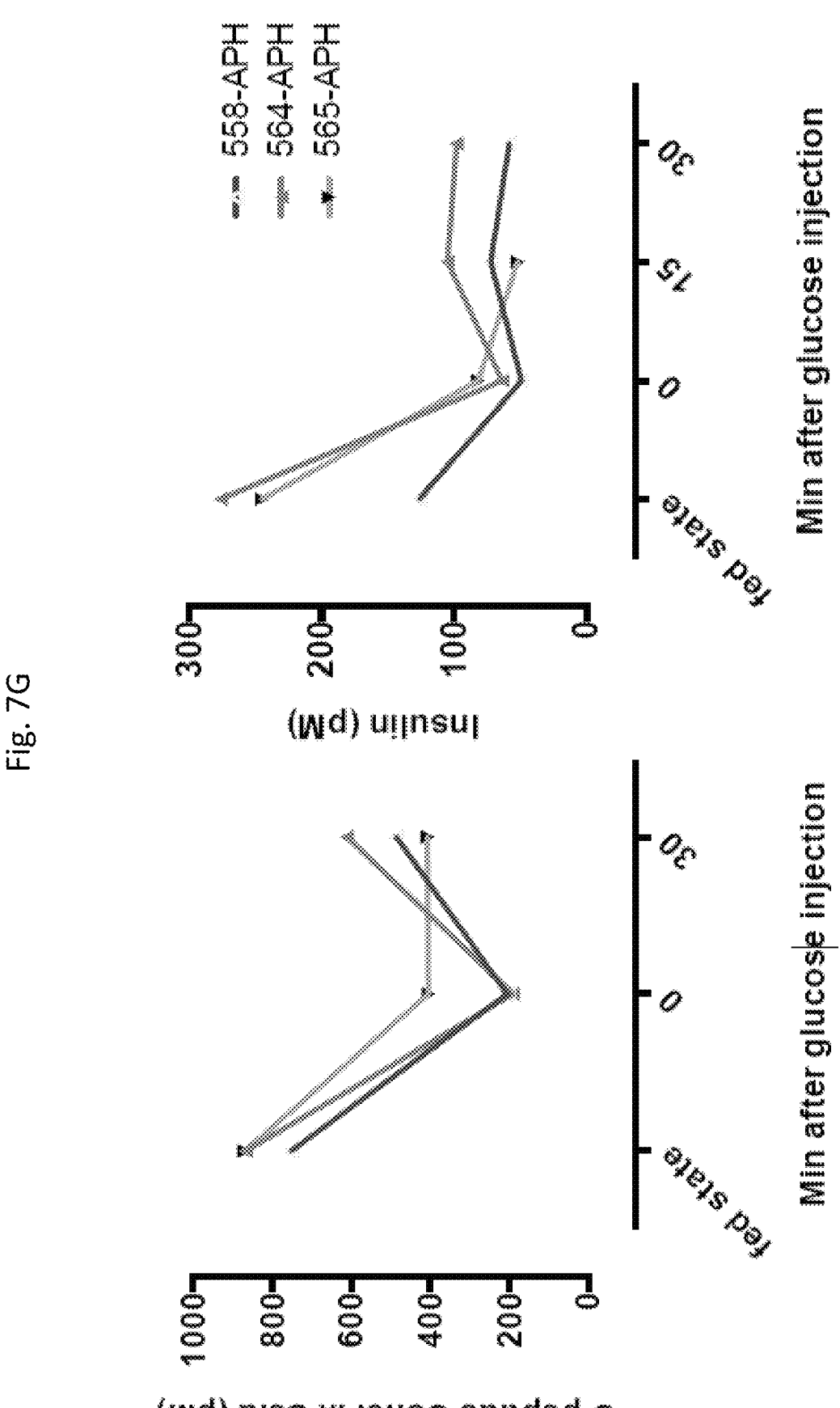
FIG. 7G shows graphs of serum human C-peptide concentrations of STZ-treated mice transplanted with APH treated cells at fed state, at fasting and indicated time point after glucose injection.

The ability of APH treated cells to protect mice from diabetes was determined after eliminating endogenous mouse beta cells by streptozotocin (STZ). STZ ablates mouse beta cells but is not toxic to human beta cells at the concentrations used. After STZ treatment, the blood glucose levels were monitored and grafted beta cells were challenged with high glucose to check their function. The blood glucose levels remained in the normal range over time in 3 out of 4 mice (FIG. 7E). Mice were tolerant to glucose and normalized blood glucose levels within 15 min of glucose injection (FIG. 7F). The secretion of human C-peptide and insulin decreased after fasting and increased after glucose injection (FIG. 7G).

Example 10—Aphidicolin Treatment Prevents Formation of Teratomas and Cysts

Figures 8, 8A, 8B:
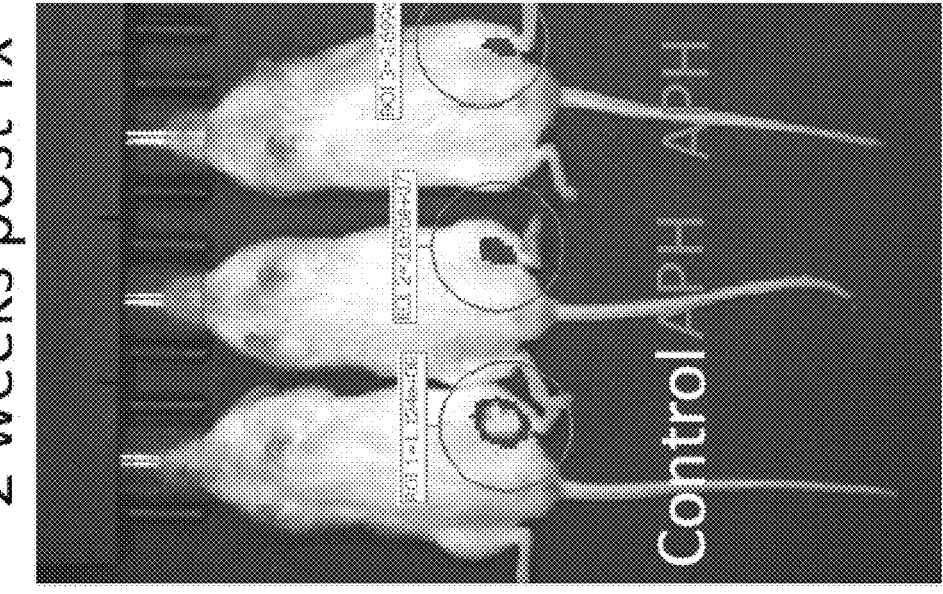
FIG. 8—APH treatment prevented formation of teratomas and cysts.
FIG. 8A are representative in vivo imaging of mice transplanted with control cells and APH treated cells at 2 weeks post-transplantation.
FIG. 8B are representative in vivo imaging of mice transplanted with control cells and APH treated cells at 13 weeks post transplantation.
Figures 8C, 8D:
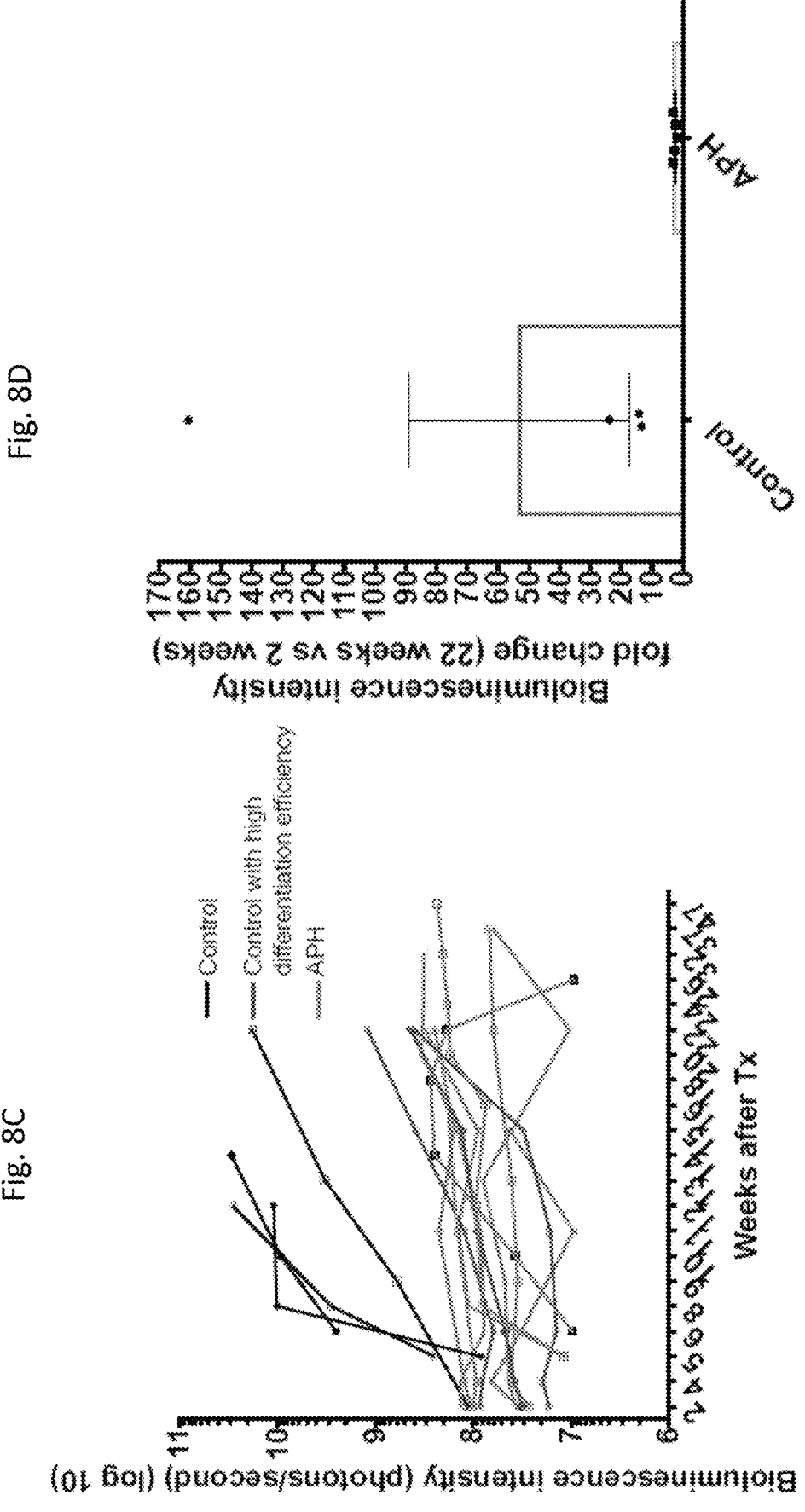
FIG. 8C is a graph showing the growth of grafted cells in mice after transplantation indicated by the bioluminescence intensity.
FIG. 8D is a graph showing fold changes of grafted cell growth in control mice and APH mice at 22 weeks of engraftment compared to 2 weeks of transplantation.
Figures 8E, 8F:
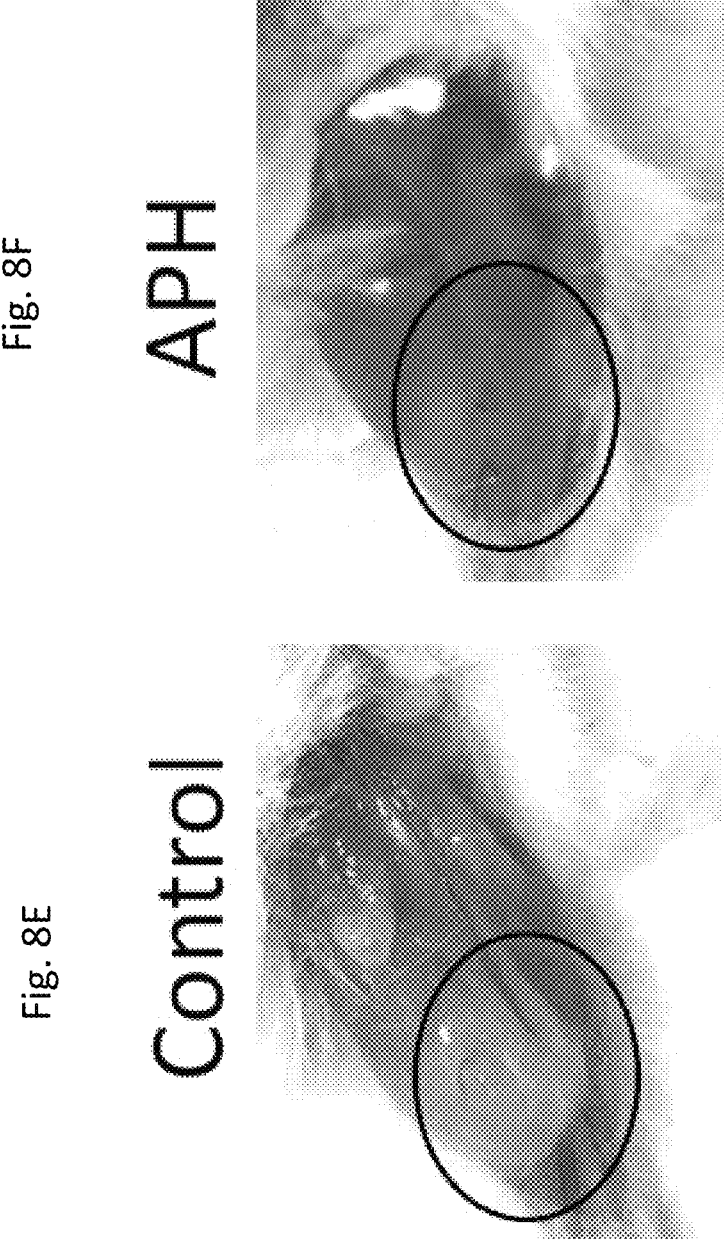
FIG. 8E is a representative image of grafted cells with equal high differentiation efficiency in control group at 36 weeks of transplantation.
FIG. 8F is a representative image of grafted cells with equal high differentiation efficiency in APH group at 36 weeks of transplantation.

A major obstacle for the therapeutic translation of stem cell products is the formation of growths, in the form of a teratoma or of a cyst. To determine growth potential of the grafted cells, growth was evaluated by monitoring the graft with a luciferase reporter using in vivo imaging. Mice were transplanted with 1-2 million APH treated cells or untreated cells. After 2 weeks of transplantation, the graft size of APH mice was small, while controls were modestly larger (FIG. 8A). Eleven weeks later, the grafted cells in control mice displayed large growths, whereas the mice transplanted with APH treated cells remained the similar size as graft at 2 weeks of grafting (FIG. 8B). The different growth trend of grafted cells between control and APH treated cells was evident in the bioluminescence intensity (FIG. 8C). At 22 weeks of engraftment, the size of graft in APH group was an average of 2.6-fold larger than that of 2 weeks compare to the control group which had 53.1-fold increase (FIG. 8D). Graft growth occurred in controls even in cultures with very high differentiation efficiency (greater than 60%). The increase of graft size was slower in the 3 mice transplanted with control cells with high differentiation efficiency but cystic structure still formed in three out of the three (3/3) mice (FIG. 8C, FIG. 8E). No cysts were observed in mice grafted with APH treated cells in four out of the four (4/4) mice (FIG. 8F).

Figure 8G:
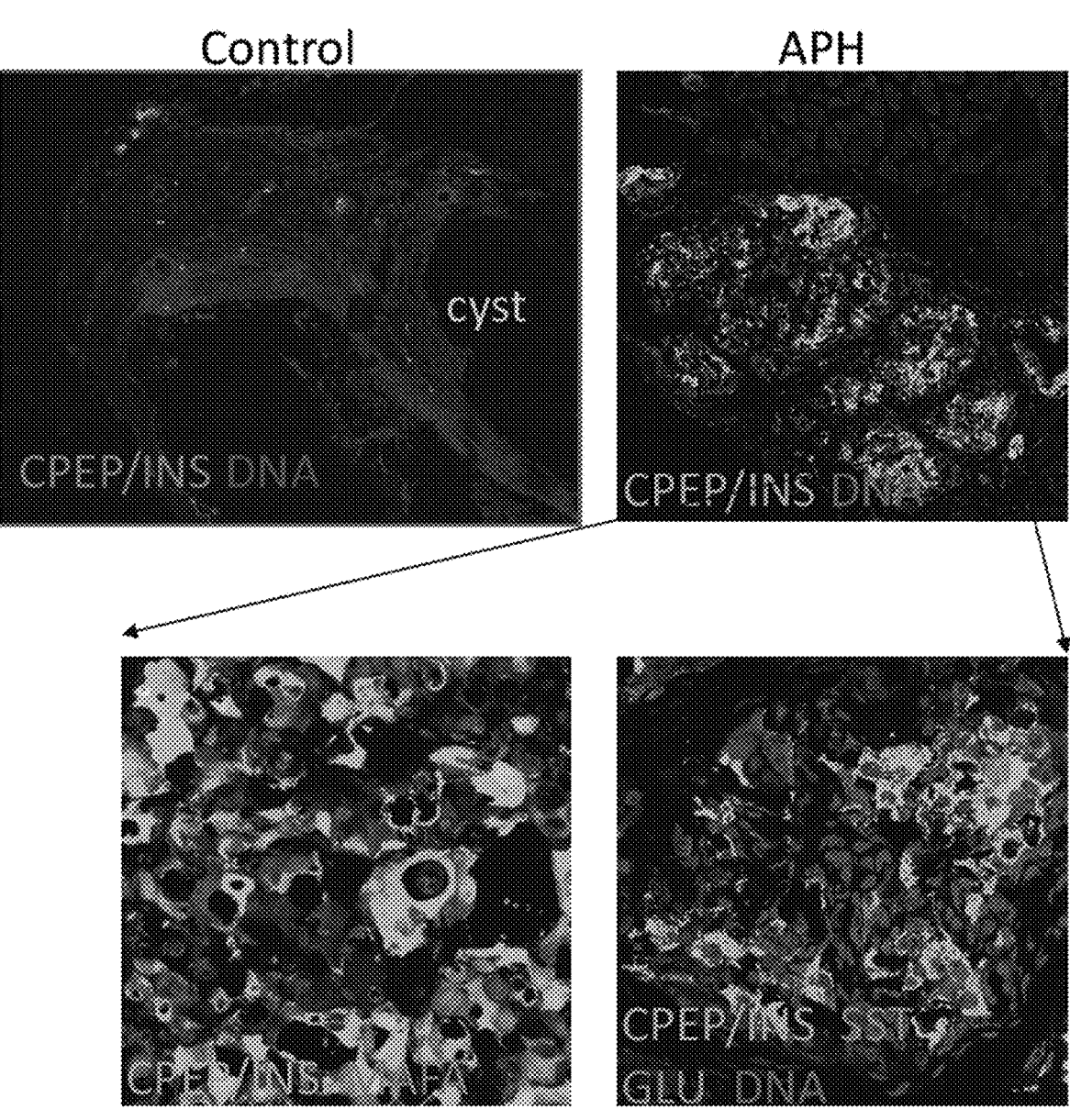
FIG. 8G are representative images of the cell composition in mice transplanted with control cells and APH treated cells.

The grafts were isolated from mice and frozen sectioned for examination. The APH grafts were composed of islet like structures, and monohormonal cells positive for insulin, glucagon or somatostatin were detected within each islet. Insulin expressing beta cells stained positive for MAFA, a master regulator for beta cell maturation. In control mice, the graft developed several large cystic structures and contained fewer C-peptide positive cells (FIG. 8G).

REFERENCES

Ameri et al. (2017). Efficient Generation of Glucose-Responsive Beta Cells from Isolated GP2(+) Human Pancreatic Progenitors. *Cell Rep* 19, 36-49.

Cliby et al. (2002). S phase and G2 arrests induced by topoisomerase I poisons are dependent on ATR kinase function. *J Biol Chem* 277, 1599-1606.

D'Amour et al. (2005). Efficient differentiation of human embryonic stem cells to definitive endoderm *Nature Biotechnology* 23, 1534-41.

D'Amour et al. (2006). Production of pancreatic hormone-expressing endocrine cells from human embryonic stem cells. *Nature Biotechnology* 24, 1392-1401.

Gardner et al. (2017). The High-Affinity Interaction between ORC and DNA that Is Required for Replication Licensing Is Inhibited by 2-Arylquinolin-4-Amines. *Cell Chem Biol* 24, 981-992 e984.

Georgieva and Egli (2017). Tying Genetic Stability to Cell Identity, *Cell Cycle* 16(12), 1139-40.

Hardwick and Philpott (2014). Nervous decision-making: to divide or differentiate. *Trends Genet* 30, 254-261.

Huang et al. (2012). Prolonged early G(1) arrest by selective CDK4/CDK6 inhibition sensitizes myeloma cells to cytotoxic killing through cell cycle-coupled loss of IRF4. *Blood* 120, 1095-1106.

Jennings et al. (2015). Human pancreas development. *Development* 142, 3126-3137.

Koundrioukoff et al. (2013). Stepwise activation of the ATR signaling pathway upon increasing replication stress impacts fragile site integrity. PLoS Genet 9, e1003643.

Korwek et al. (2012). Inhibition of ATM blocks the etoposide-induced DNA damage response and apoptosis of resting human T cells. *DNA Repair* (Amst) 11, 864-873.

Kulkarni et al. (2012). Human beta-cell proliferation and intracellular signaling: driving in the dark without a road map. *Diabetes* 61, 2205-2213.

Lasko et al. (2017). Discovery of a selective catalytic p300/CBP inhibitor that targets lineage-specific tumours. *Nature* 550, 128-132.

Ma et al. (2008). A small-molecule E2F inhibitor blocks growth in a melanoma culture model. *Cancer Res* 68, 6292-6299.

Mfopou and Bouwens (2008). Hedge-hog signals in pancreatic differentiation from embryonic stem cells: revisiting the neglected. *Differentiation* 76, 107-17.

Mfopou et al (2010). Noggin. Retinoids, and fibroblast growth factor regulate hepatic or pancreatic fate of human embryonic stem cells. *Gastroenterology* 138, 2233-45.

Moruno-Manchon et al. (2017). The G-quadruplex DNA stabilizing drug pyridostatin promotes DNA damage and downregulates transcription of Brcal in neurons. *Aging* (Albany NY) 9, 1957-1970.

Nam et al. (2010). Etoposide induces G2/M arrest and apoptosis in neural progenitor cells via DNA damage and an ATM/p53-related pathway. *Histol Histopathol* 25, 485-493.

Nostro et al. (2015). Efficient generation of NKX-1+ pancreatic progenitors from multiple human pluripotent stem cell lines. *Stem Cell Reports* 4, 591-604.

Pardee et al. (2004). Regulation in S phase by E2F. *Cell Cycle* 3, 1091-1094.

Qin and Ng (2002). Induction of apoptosis by cisplatin and its effect on cell cycle-related proteins and cell cycle changes in hepatoma cells. *Cancer Lett* 175, 27-38.

Shih et al. (2014) A Notch-dependent molecular circuitry initiates pancreatic endocrine and ductal cell differentiation. Development 139, 2488-99

Rouaud et al. (2018). E2F1 inhibition mediates cell death of metastatic melanoma. *Cell Death Dis* 9, 527.

Schaffer et al. (2013). Nkx6.1 controls a gene regulatory network required for establishing and maintaining pancreatic Beta cell identity. *PLoS Genet* 9, e1003274.

Sclafani and Holzen (2007). Cell cycle regulation of DNA replication. *Annu Rev Genet* 41, 237-280.

Simon et al. (2013). Ciprofloxacin is an inhibitor of the Mcm2-7 replicative helicase. *Biosci Rep* 33.

Smith et al. (1994). Etoposide-induced cell cycle delay and arrest-dependent modulation of DNA topoisomerase II in small-cell lung cancer cells. *Br J Cancer* 70, 914-921.

Sui et al. (2018a). beta-Cell Replacement in Mice Using Human Type 1 *Diabetes* Nuclear Transfer Embryonic Stem Cells. *Diabetes* 67, 26-35.

Sui et al. (2018b). Pancreatic Beta Cell Differentiation From Human Pluripotent Stem Cells. *Curr Protoc Hum Genet* 99, e68.

Sui et al. 2013 Role of BMP Signaling in pancreatic progenitor differentiation from human embryonic stem cell. *Stem Cell Reviews* 9, 569-77.

Wagner and Karnitz (2009). Cisplatin-induced DNA damage activates replication checkpoint signaling components that differentially affect tumor cell survival. Mol Pharmacol 76, 208-214.

Walsh and Perlman (1997). Cell cycle exit upon myogenic differentiation. *Curr Opin Genet Dev* 7, 597-602.

Zimmer et al. (2016). Targeting BRCA1 and BRCA2 Deficiencies with G-Quadruplex-Interacting Compounds. Mol Cell 61, 449-460.

The invention claimed is:

1. A method of inducing cell cycle exit and terminal differentiation of cells undergoing differentiation from pluripotent stem cells into mature differentiated cells, comprising the steps of:
   a. sequentially differentiating the pluripotent stem cells to obtain pancreatic progenitor cells; and
   b. contacting or incubating the pancreatic progenitor cells with an agent which interferes with DNA replication to induce cell cycle exit;
   wherein the mature differentiated cells are beta cells differentiated from the pluripotent stem cells.

2. The method of claim 1, wherein the pluripotent stem cells are embryonic stem cells or induced pluripotent stem cells.

3. The method of claim 1, wherein the agent interferes with DNA replication in the G1 phase of the cell cycle.

4. The method of claim 1, wherein the agent is chosen from the group consisting of inhibitors of DNA polymerase, compounds which stabilize G4 structures and arrest cell cycle, DNA helicase inhibitors, inhibitors of MCM 2-7 replicative helicase, inhibitors of MCM 4/6/7 replicative helicase, inhibitors of RecQ helicases, topoisomerase inhibitors, inhibitors of histone acetylases, inhibitors of master transcription factors involved in S phase entry, inhibitors of replication origin licensing, DNA damaging agents, and PNA oligonucleotides.

5. The method of claim 4, wherein the inhibitor of DNA polymerase is chosen from the group consisting of aphidicolin and gemcitabine.

6. The method of claim 4, wherein the compound which stabilizes G4 structures is chosen from the group consisting of pyridostatin and TMPyP4.

7. The method of claim 4, wherein the DNA helicase inhibitor is chosen from the group consisting of WRN, BLM, and DNA2.

8. The method of claim 4, wherein the topoisomerase inhibitor is chosen from the group consisting of etoposide, doxorubicin, topotecan, and irinotecan.

9. The method of claim 4, wherein the inhibitor of histone acetylases is chosen from the group consisting of A485 and C646 (inhibitor of p300 and Creb-binding protein (CBP)), curcumin, garcinol, and 5-chloro-2-(4-nitrophenyl)-3 (2H)-isothiazolone.

10. The method of claim 4, wherein the inhibitor of master transcription factors involved in the S phase entry is an E2F inhibitor.

11. The method of claim 4, wherein the DNA damaging agent is chosen from the group consisting of cisplatin, derivatives of cisplatin, chlorambucil, cyclophosphamide, alkylating agents, 5-fluorouracil, and irradiation.

12. The method of claim 1, wherein the agent is chosen from the group consisting of aphidicolin, cisplatin, ciprofloxacin, pyridostatin, E2Fi, A485, RL5a and etoposide.

13. The method of claim 1, wherein the progenitor cells are contacted or incubated with the agents from about day 15 to about day 20 of the entire differentiation protocol for about five days to about two weeks.

14. The method of claim 1, wherein the progenitor cells are contacted or incubated with the agent at a stage in the differentiation protocol selected from the group consisting of: the early stage of the differentiation of progenitor cells to mature differentiated cells; the late stage of the differentiation of progenitor cells to mature differentiated cells; and the entire stage of the differentiation of progenitor cells to mature differentiated cells.

15. The method of claim 1, wherein the progenitor cells are contacted or incubated with the agent for at least about 1-2 weeks.

* * * * *